United States Patent
Renner et al.

(10) Patent No.: US 11,118,179 B2
(45) Date of Patent: Sep. 14, 2021

(54) MIXED TRICYCLO-DNA, 2'-MODIFIED RNA OLIGONUCLEOTIDE COMPOSITIONS AND USES THEREOF

(71) Applicant: Synthena AG, Bern (CH)

(72) Inventors: Wolfgang Andreas Renner, Zurich (CH); Branislav Dugovic, Bern (CH)

(73) Assignee: Synthena AG, Bern (CH)

( * ) Notice: Subject to any disclaimer, the term of this patent is extended or adjusted under 35 U.S.C. 154(b) by 65 days.

(21) Appl. No.: 16/335,748

(22) PCT Filed: Sep. 22, 2017

(86) PCT No.: PCT/IB2017/055782
§ 371 (c)(1),
(2) Date: Mar. 22, 2019

(87) PCT Pub. No.: WO2018/055577
PCT Pub. Date: Mar. 29, 2018

(65) Prior Publication Data
US 2019/0218554 A1    Jul. 18, 2019

Related U.S. Application Data

(60) Provisional application No. 62/399,328, filed on Sep. 23, 2016.

(30) Foreign Application Priority Data

Apr. 20, 2017 (EP) ..................................... 17167426

(51) Int. Cl.
*C12N 15/113*    (2010.01)
*A61P 21/00*    (2006.01)
*A61K 31/7088*    (2006.01)

(52) U.S. Cl.
CPC ........ *C12N 15/113* (2013.01); *A61K 31/7088* (2013.01); *A61P 21/00* (2018.01); *C12N 2310/313* (2013.01); *C12N 2310/314* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/533* (2013.01); *C12N 2320/33* (2013.01); *C12N 2320/52* (2013.01); *C12N 2320/53* (2013.01)

(58) Field of Classification Search
None
See application file for complete search history.

(56) References Cited

FOREIGN PATENT DOCUMENTS

| EP | 2581448 A1 | 4/2013 |
| WO | 2008049085 A1 | 4/2008 |
| WO | 2009039173 A2 | 3/2009 |
| WO | 2016089433 A1 | 6/2016 |

OTHER PUBLICATIONS

Aurelie Goyenvalle et al.; Therapeutic Potential of Trycylo-DNA antisense oligonucleotides:, Journal of Neuromuscula Diseases, Sep. 22, 2014, vol. 3, No. 2, May 27, 2016, pp. 157-167.
D. Renneberg et al.; "Antisense Porperties of Tricyclo-DNA", Nucleic Acids Research, vol. 30, No. 13, Jul. 1, 2002, pp. 2751-2757.
S. Murray et al.; "TricycloDNA-modified oligo-2'-deosyribonuecleotides reduce scavenger receptor B1 mRNA in Hepatic and Extra-Hepatic tissues—a comparative study of oligonucleotide length, design and chemistry"; Nucleic Acids Research, vol. 40, No. 13, Jul. 1, 2012, pp. 6135-6143.
Ittig, Damian et al.; "Nuclear Antisense Effects in Cyclophilin a pre-mRNA splicing by oligonucleotides: a comparison of trycyclo-DNA with LNA".
Damian Ittig et al.: "Position-dependent Effects on Stability in Trycyclo-DNA modified oligonucleotide duplexes", Nucleic Acids Research, Oxford University Press, GB, vol. 39, No. 1, Jan. 1, 2011, pp. 373-380.
ntemational Search Report dated Nov. 13, 2017 for International Patent Application PCT/IB2017/055782, 6 pages.

*Primary Examiner* — Tracy Vivlemore
(74) *Attorney, Agent, or Firm* — Morgan, Lewis & Bockius LLP

(57) ABSTRACT

In some embodiments, disclosed herein are oligomeric compounds which include one or more tricyclo-deoxyribonucleic acid (tc-DNA) nucleosides and one or more 2'-modified ribonucleic acid (2'-modified-RNA) nucleosides, and which optionally also include one or more non-nucleotides, each of which is joined by a plurality of internucleoside linkages, including pharmaceutical compositions and methods of using the pharmaceutical compositions for the treatment of diseases including Duchenne muscular dystrophy treatment of familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease).

22 Claims, 26 Drawing Sheets
Specification includes a Sequence Listing.

Sequence:           5'-AAGATGGCATTTCTA-3'

Homodimerization:   5'    AAGATGGCATTTCTA     | = Watson-Crick
                          |:|||   |||:|
                    3'    ATCTTTACGGTAGAA     : = Wobble

FIG. 1

Melting curves tc/2'-MeO-mixed Sequneces, 01.06.2016
Carried out according to SOP A025_02. All medium salt concentration (75 mM NaCl, 10 mM NaH2PO4, pH 7.0). The first ramp was not used for the calculation.

Duplex against RNA

| | MK352 | TT348 | TT349 | TT350 | TT351 | TT352 | TT353 | TT354 | TT355 | TT356 | TT357 | TT358 | TT359 |
|---|---|---|---|---|---|---|---|---|---|---|---|---|---|
| | Full tc | 1x MeO | 1x MeO | 1x MeO | 1x MeO | 2x MeO | 2x MeO | 2x MeO | 3x MeO | 3x MeO | 3x MeO | 4x MeO | 4x MeO |
| | AAG ATG GCA TTT CTA | AAG aTG GCA TTT CTA | AAG AuG GCA TTT CTA | AAG Atg GCA TTT CTA | AAG ATG GcA TTT CTA | AAG auG GCA TTT CTA | AAG aTg GCA TTT CTA | AAG aTG GcA TTT CTA | AAG aug GCA TTT CTA | AAG auG GcA TTT CTA | AAG AuG GcA uTT CTA | AaG aug GCA TTT CTA | AAG ATG Gcu uTu CTA |
| 1 | 80.02 | 75.97 | 75.92 | 72.97 | 75.87 | 73.82 | 68.72 | 69.02 | 71.02 | 70.02 | 64.92 | 68.98 | 64.91 |
| 2 | 81.07 | 76.07 | 76.07 | 73.99 | 75.12 | 74.17 | 68.22 | 70.07 | 72.07 | 68.12 | 65.07 | 68.07 | 63.12 |
| 3 | 78.97 | 74.92 | 75.87 | 72.97 | 74.87 | 74.77 | 69.72 | 70.07 | 71.97 | 69.02 | 65.92 | n/a | 62.90 |
| 4 | 79.07 | 76.07 | 76.07 | 74.97 | 74.12 | 74.16 | 68.22 | 71.07 | 71.12 | 69.07 | 64.07 | 69.07 | 64.12 |
| 5 | 79.02 | 75.92 | 74.87 | 72.97 | 74.87 | 74.77 | 69.76 | 69.02 | 71.02 | 70.02 | 64.97 | 68.97 | 63.92 |
| 6 | 80.07 | 76.07 | 76.07 | 74.97 | 75.11 | 75.17 | 69.22 | 70.07 | 73.07 | 69.12 | 66.12 | 70.07 | 65.12 |
| Mean | 79.6 | 75.8 | 75.8 | 74.0 | 74.8 | 74.6 | 69.0 | 70.1 | 71.9 | 69.1 | 65.2 | 69.0 | 63.8 |
| SD | 0.92 | 0.50 | 0.52 | 1.00 | 0.41 | 0.44 | 0.77 | 0.72 | 0.83 | 0.67 | 0.82 | 0.82 | 0.88 |
| RSD | 1.16 | 0.66 | 0.69 | 1.35 | 0.55 | 0.58 | 1.11 | 1.03 | 1.16 | 0.97 | 1.26 | 1.18 | 1.38 |
| ΔTm | 0.0 | -3.8 | -3.8 | -5.6 | -4.8 | -5.0 | -10.6 | -9.5 | -7.8 | -10.5 | -14.4 | -10.6 | -15.8 |
| Modifications | 0 | 1 | 1 | 1 | 1 | 2 | 2 | 2 | 3 | 3 | 3 | 4 | 4 |
| ΔTm/mod | n/a | -3.8 | -3.8 | -5.6 | -4.8 | -2.5 | -5.3 | -4.8 | -2.6 | -3.5 | -4.8 | -2.6 | -3.9 |

Single strand

| | MK352 | TT348 | TT349 | TT350 | TT351 | TT352 | TT353 | TT354 | TT355 | TT356 | TT357 | TT358 | TT359 |
|---|---|---|---|---|---|---|---|---|---|---|---|---|---|
| | Full tc | 1x MeO | 1x MeO | 1x MeO | 1x MeO | 2x MeO | 2x MeO | 2x MeO | 3x MeO | 3x MeO | 3x MeO | 4x MeO | 4x MeO |
| | AAG ATG GCA TTT CTA | AAG aTG GCA TTT CTA | AAG AuG GCA TTT CTA | AAG Atg GCA TTT CTA | AAG ATG GcA TTT CTA | AAG auG GCA TTT CTA | AAG aTg GCA TTT CTA | AAG aTG GcA TTT CTA | AAG aug GCA TTT CTA | AAG auG GcA TTT CTA | AAG AuG GcA uTT CTA | AaG aug GCA TTT CTA | AAG ATG Gcu uTu CTA |
| 1 | 70.72 | 57.03 | 59.97 | 71.92 | 79.82 | 55.82 | 57.77 | 63.82 | 40.82 | 46.82 | 57.77 | 33.77 | 35.77 |
| 2 | 67.22 | 56.02 | 63.07 | 75.07 | 78.12 | 49.17 | 58.12 | 65.07 | 45.22 | 49.17 | 55.22 | 31.22 | 85.27 |
| 3 | 66.76 | 56.97 | 60.92 | 72.87 | 82.82 | 50.82 | 62.82 | 61.87 | 45.82 | 48.82 | 57.77 | 31.72 | 58.72 |
| 4 | 69.22 | 54.07 | 65.07 | 74.07 | 83.07 | 48.17 | 61.12 | 63.12 | 45.22 | 50.17 | 62.22 | 34.18 | 86.24 |
| 5 | 69.77 | 57.02 | 57.97 | 72.92 | 76.87 | 46.82 | 55.82 | 64.82 | 42.77 | 46.87 | 59.77 | 35.72 | 80.79 |
| 6 | 70.22 | 56.07 | 60.07 | 77.07 | 79.07 | 46.17 | 61.12 | 63.17 | 42.22 | 46.17 | 60.22 | 34.22 | 85.27 |
| Mean | 68.6 | 56.0 | 61.4 | 74.4 | 80.0 | 48.2 | 59.8 | 63.6 | 44.3 | 48.2 | 59.0 | 33.4 | |
| SD | 1.55 | 1.19 | 2.74 | 1.75 | 2.81 | 1.86 | 2.80 | 1.33 | 1.63 | 1.66 | 2.66 | 1.89 | |
| RSD | 2.26 | 2.13 | 4.46 | 2.35 | 3.51 | 3.85 | 4.68 | 2.09 | 3.69 | 3.45 | 4.50 | 5.65 | |
| ΔTm | 0.0 | -12.6 | -7.2 | 5.8 | 11.4 | -20.4 | -8.8 | -5.0 | -24.4 | -20.4 | -9.6 | -35.2 | |
| Modifications | 0 | 1 | 1 | 1 | 1 | 2 | 2 | 2 | 3 | 3 | 3 | 4 | 4 |
| ΔTm/mod | n/a | -12.6 | -7.2 | 5.8 | 11.4 | -10.2 | -4.4 | -2.5 | -8.1 | -6.8 | -3.2 | -8.8 | |
| Comments | Ok | OK | RSD>4.0 | Ok | Ok | Ok | RSD>4.0 | Ok | Ok | OK | RSD>4.0 | RSD>4.0 | No transition |

FIG. 21

Melting curves tc/2'-MeO-PO/PS-mixed Sequneces (Project Detox Phase 2), 08.08.2016
Carried out according to SOP A025_02. All medium salt concentration (75 mM NaCl, 10 mM NaH2PO4, pH 7.0).
The first ramp was not used for the calculation.

Duplex against RNA

|  | SY-0340-TT477 | SY-0371-TT474 | SY-0372-TT488 | SY-0373-TT478 | SY-0374-TT476 | SY-0375-TT487 | SY-0382-TT489 | SY-0383-TT479 | SY-0386-TT490 |
|---|---|---|---|---|---|---|---|---|---|
| Length | 15 | 15 | 15 | 15 | 18 | 18 | 15 | 18 | 15 |
| PS | 14 | 6 | 6 | 5 | 6 | 17 | 5 | 6 | 4 |
| 2'-OMe | 4 | 4 | 3 | 4 | 5 | 5 | 4 | 5 | 3 |
| 1 | 69.02 | 63.97 | 58.92 | 70.07 | 79.87 | 83.82 | 83.77 | 84.97 | 81.92 |
| 2 | 70.17 | 65.17 | 60.17 | 68.07 | 79.22 | 84.22 | 82.29 | 85.07 | 83.12 |
| 3 | 68.97 | 64.92 | 60.87 | 68.02 | 78.82 | 82.77 | 82.72 | 84.92 | 82.87 |
| 4 | 70.17 | 65.16 | 60.17 | 69.12 | 80.17 | 84.27 | 82.32 | 86.11 | 83.17 |
| 5 | 67.97 | 63.92 | 60.87 | 68.97 | 78.87 | 83.77 | 81.72 | 85.96 | 82.87 |
| 6 | 70.12 | 65.12 | 60.12 | 69.07 | 80.22 | 83.24 | 82.32 | 85.12 | 84.07 |
| Mean | 69.5 | 64.9 | 60.4 | 68.7 | 79.5 | 83.7 | 82.3 | 85.4 | 83.2 |
| SD | 0.99 | 0.53 | 0.39 | 0.56 | 0.69 | 0.65 | 0.36 | 0.55 | 0.49 |
| RSD | 1.42 | 0.82 | 0.65 | 0.81 | 0.87 | 0.77 | 0.43 | 0.65 | 0.59 |
| $\Delta$Tm* | -10.1 | -14.7 | -19.2 | n/a | n/a | n/a | n/a | n/a | n/a |
| $\Delta$Tm/mod | -2.5 | -3.7 | -6.4 |  |  |  |  |  |  |

* Calculated with the value from 01.06.2016

FIG. 22

Melting curves 18-mer-tc/2'-MeO-PO/PS-mixed sequneces (Project detox phase 3), 25.08.2016

Carried out according to SOP A025_02. All medium salt concentration (75 mM NaCl, 10 mM NaH2PO4, pH 7.0).
The first ramp was not used for the calculation.

Duplex against 21-mer-RNA

|  | SY-0388-MK581 | SY-0389-MK582 | SY-0390-MK587 | SY-0391-MK588 | SY-0392-MK589 | SY-0393-MK590 | SY-0394-MK601 | SY-0395-MK585 | SY-0396-MK586 | SY-0397-MK592 | SY-0398-MK593 |
|---|---|---|---|---|---|---|---|---|---|---|---|
| Length | 18 | 18 | 18 | 18 | 18 | 18 | 18 | 17 | 16 | 18 | 18 |
| PS | 6 | 8 | 6 | 6 | 5 | 4 | 6 | 6 | 6 | 6 | 7 |
| 2'-OMe | 5 | 7 | 4 | 5 | 4 | 3 | 5 | 5 | 5 | 5 | 6 |
| 1 | 77.02 | 76.97 | 71.02 | 72.82 | 72.77 | 78.72 | 75.97 | 75.92 | 73.90 | 76.82 | 75.77 |
| 2 | 77.12 | 76.12 | 72.02 | 73.17 | 72.22 | 78.27 | 76.07 | 75.17 | 74.17 | 77.17 | 76.27 |
| 3 | 76.97 | 76.92 | 71.97 | 72.87 | 72.77 | 77.72 | 76.02 | 75.97 | 73.87 | 76.85 | 75.77 |
| 4 | 77.17 | 77.12 | 73.02 | 73.22 | 73.21 | 77.27 | 76.17 | 75.17 | 74.22 | 77.27 | 75.32 |
| 5 | 77.02 | 76.97 | 71.97 | 72.82 | 72.77 | 78.72 | 75.97 | 74.92 | 73.87 | 76.82 | 75.72 |
| 6 | 77.12 | 77.17 | 73.02 | 73.17 | 73.22 | 78.32 | 76.17 | 76.17 | 74.22 | 77.22 | 75.27 |
| Mean | 77.1 | 76.9 | 72.4 | 73.1 | 72.8 | 78.1 | 76.1 | 75.5 | 74.1 | 77.1 | 75.7 |
| SD | 0.08 | 0.43 | 0.57 | 0.19 | 0.41 | 0.57 | 0.09 | 0.55 | 0.18 | 0.21 | 0.40 |
| RSD | 0.11 | 0.55 | 0.78 | 0.26 | 0.56 | 0.73 | 0.12 | 0.73 | 0.25 | 0.28 | 0.53 |

FIG. 23

SEQUENCE LISTING

```
<160> NUMBER OF SEQ ID NOS: 135

<210> SEQ ID NO 1
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(4)
<220> FEATURE:
<221> NAME/KEY: tc-DNA
<222> LOCATION: (5)..(15)

<400> SEQUENCE: 1
aagatggcat ttcta                                                    15
```

```
<210> SEQ ID NO 2
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(4)
<220> FEATURE:
<221> NAME/KEY: 2'-modified-RNA
<222> LOCATION: (5)..(5)
<220> FEATURE:
<221> NAME/KEY: tc-DNA
<222> LOCATION: (6)..(15)

<400> SEQUENCE: 2
aagauggcat ttcta                                                  15

<210> SEQ ID NO 3
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(5)
<220> FEATURE:
<221> NAME/KEY: 2'-modified-RNA
<222> LOCATION: (6)..(6)
<220> FEATURE:
<221> NAME/KEY: tc-DNA
<222> LOCATION: (7)..(15)

<400> SEQUENCE: 3
aagatggcat ttcta                                                  15

<210> SEQ ID NO 4
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(15)

<400> SEQUENCE: 4
aagatggcat ttcta                                                  15

<210> SEQ ID NO 5
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
```

```
<222> LOCATION: (4)..(5)
<220> FEATURE:
<221> NAME/KEY: tc-DNA
<222> LOCATION: (6)..(15)

<400> SEQUENCE: 5
aagauggcat ttcta                                                    15

<210> SEQ ID NO 6
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(4)
<220> FEATURE:
<221> NAME/KEY: tc-DNA
<222> LOCATION: (5)..(5)
<220> FEATURE:
<221> NAME/KEY: 2'-modified-RNA
<222> LOCATION: (6)..(6)
<220> FEATURE:
<221> NAME/KEY: tc-DNA
<222> LOCATION: (7)..(15)

<400> SEQUENCE: 6
aagatggcat ttcta                                                    15

<210> SEQ ID NO 7
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(4)
<220> FEATURE:
<221> NAME/KEY: tc-DNA
<222> LOCATION: (5)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(15)

<400> SEQUENCE: 7
aagatggcat ttcta                                                    15

<210> SEQ ID NO 8
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(6)
```

```
<220> FEATURE:
<221> NAME/KEY: tc-DNA
<222> LOCATION: (7)..(15)

<400> SEQUENCE: 8
aagauggcat ttcta                                                        15

<210> SEQ ID NO 9
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(5)
<220> FEATURE:
<221> NAME/KEY: tc-DNA
<222> LOCATION: (6)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(15)

<400> SEQUENCE: 9
aagauggcat ttcta                                                        15

<210> SEQ ID NO 10
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(4)
<220> FEATURE:
<221> NAME/KEY: 2'-modified-RNA
<222> LOCATION: (5)..(5)
<220> FEATURE:
<221> NAME/KEY: tc-DNA
<222> LOCATION: (6)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(9)
<220> FEATURE:
<221> NAME/KEY: 2'-modified-RNA
<222> LOCATION: (10)..(10)
<220> FEATURE:
<221> NAME/KEY: tc-DNA
<222> LOCATION: (11)..(15)

<400> SEQUENCE: 10
aagauggcau ttcta                                                        15

<210> SEQ ID NO 11
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
```

```
<221> NAME/KEY: tc-DNA
<222> LOCATION: (1)..(1)
<220> FEATURE:
<221> NAME/KEY: 2'-modified-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-modified-RNA
<222> LOCATION: (4)..(6)
<220> FEATURE:
<221> NAME/KEY: tc-DNA
<222> LOCATION: (5)..(15)

<400> SEQUENCE: 11
aagauggcat ttcta                                               15

<210> SEQ ID NO 12
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(7)
<220> FEATURE:
<221> NAME/KEY: 2'-modified-RNA
<222> LOCATION: (8)..(10)
<220> FEATURE:
<221> NAME/KEY: tc-DNA
<222> LOCATION: (11)..(11)
<220> FEATURE:
<221> NAME/KEY: 2'-modified-RNA
<222> LOCATION: (12)..(12)
<220> FEATURE:
<221> NAME/KEY: tc-DNA
<222> LOCATION: (13)..(15)

<400> SEQUENCE: 12
aagatggcau tucta                                               15

<210> SEQ ID NO 13
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(1)
<220> FEATURE:
<221> NAME/KEY: 2'-modified-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-modified-RNA
<222> LOCATION: (4)..(6)
<220> FEATURE:
<221> NAME/KEY: tc-DNA
<222> LOCATION: (7)..(15)

<400> SEQUENCE: 13
aagauggcat ttcta                                               15

<210> SEQ ID NO 14
<211> LENGTH: 15
<212> TYPE: DNA
```

<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(9)
<220> FEATURE:
<221> NAME/KEY: 2'-modified-RNA
<222> LOCATION: (10)..(10)
<220> FEATURE:
<221> NAME/KEY: tc-DNA
<222> LOCATION: (11)..(11)
<220> FEATURE:
<221> NAME/KEY: 2'-modified-RNA
<222> LOCATION: (12)..(12)
<220> FEATURE:
<221> NAME/KEY: tc-DNA
<222> LOCATION: (13)..(13)
<220> FEATURE:
<221> NAME/KEY: 2'-modified-RNA
<222> LOCATION: (14)..(14)
<220> FEATURE:
<221> NAME/KEY: tc-DNA
<222> LOCATION: (15)..(15)

<400> SEQUENCE: 14
aagatggcau tucua                                                    15

<210> SEQ ID NO 15
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(10)
<220> FEATURE:
<221> NAME/KEY: 2'-modified-RNA
<222> LOCATION: (11)..(14)
<220> FEATURE:
<221> NAME/KEY: tc-DNA
<222> LOCATION: (15)..(15)

<400> SEQUENCE: 15
gaagatggca uuuct                                                    15

<210> SEQ ID NO 16
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(9)
<220> FEATURE:
<221> NAME/KEY: 2'-modified-RNA
<222> LOCATION: (10)..(10)
<220> FEATURE:
<221> NAME/KEY: tc-DNA
<222> LOCATION: (11)..(15)

<400> SEQUENCE: 16
aagatggcau ttcta                                                    15

<210> SEQ ID NO 17
<211> LENGTH: 15
<212> TYPE: DNA
<213> ORGANISM: Artificial Sequence

```
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(8)
<220> FEATURE:
<221> NAME/KEY: 2'-modified-RNA
<222> LOCATION: (9)..(9)
<220> FEATURE:
<221> NAME/KEY: tc-DNA
<222> LOCATION: (10)..(15)

<400> SEQUENCE: 17
aagatggcat ttcta                                                   15

<210> SEQ ID NO 18
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(4)
<220> FEATURE:
<221> NAME/KEY: 2'-modified-RNA
<222> LOCATION: (5)..(6)
<220> FEATURE:
<221> NAME/KEY: tc-DNA
<222> LOCATION: (7)..(15)

<400> SEQUENCE: 18
aagauggcat ttcta                                                   15

<210> SEQ ID NO 19
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(8)
<220> FEATURE:
<221> NAME/KEY: 2'-modified-RNA
<222> LOCATION: (9)..(10)
<220> FEATURE:
<221> NAME/KEY: tc-DNA
<222> LOCATION: (11)..(15)

<400> SEQUENCE: 19
aagatggcau ttcta                                                   15

<210> SEQ ID NO 20
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(9)
<220> FEATURE:
```

```
<221> NAME/KEY: 2'-modified-RNA
<222> LOCATION: (10)..(10)
<220> FEATURE:
<221> NAME/KEY: tc-DNA
<222> LOCATION: (11)..(15)

<400> SEQUENCE: 20
aagatggcau ttcta                                                          15

<210> SEQ ID NO 21
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(7)
<220> FEATURE:
<221> NAME/KEY: 2'-modified-RNA
<222> LOCATION: (8)..(9)
<220> FEATURE:
<221> NAME/KEY: tc-DNA
<222> LOCATION: (10)..(15)

<400> SEQUENCE: 21
aagatggcat ttcta                                                          15

<210> SEQ ID NO 22
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(4)
<220> FEATURE:
<221> NAME/KEY: tc-DNA
<222> LOCATION: (5)..(8)
<220> FEATURE:
<221> NAME/KEY: 2'-modified-RNA
<222> LOCATION: (9)..(9)
<220> FEATURE:
<221> NAME/KEY: tc-DNA
<222> LOCATION: (10)..(15)

<400> SEQUENCE: 22
aagatggcat ttcta                                                          15

<210> SEQ ID NO 23
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(4)
<220> FEATURE:
<221> NAME/KEY: 2'-modified-RNA
<222> LOCATION: (5)..(5)
<220> FEATURE:
<221> NAME/KEY: tc-DNA
<222> LOCATION: (6)..(9)
<220> FEATURE:
<221> NAME/KEY: 2'-modified-RNA
```

```
<222> LOCATION: (10)..(10)
<220> FEATURE:
<221> NAME/KEY: tc-DNA
<222> LOCATION: (11)..(15)

<400> SEQUENCE: 23
aagauggcau ttcta                                                      15

<210> SEQ ID NO 24
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(4)
<220> FEATURE:
<221> NAME/KEY: 2'-modified-RNA
<222> LOCATION: (5)..(5)
<220> FEATURE:
<221> NAME/KEY: tc-DNA
<222> LOCATION: (6)..(7)
<220> FEATURE:
<221> NAME/KEY: 2'-modified-RNA
<222> LOCATION: (8)..(8)
<220> FEATURE:
<221> NAME/KEY: tc-DNA
<222> LOCATION: (9)..(15)

<400> SEQUENCE: 24
aagauggcat ttcta                                                      15

<210> SEQ ID NO 25
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(5)
<220> FEATURE:
<221> NAME/KEY: 2'-modified-RNA
<222> LOCATION: (6)..(6)
<220> FEATURE:
<221> NAME/KEY: tc-DNA
<222> LOCATION: (7)..(9)
<220> FEATURE:
<221> NAME/KEY: 2'-modified-RNA
<222> LOCATION: (10)..(10)
<220> FEATURE:
<221> NAME/KEY: tc-DNA
<222> LOCATION: (11)..(15)

<400> SEQUENCE: 25
aagatggcau ttcta                                                      15

<210> SEQ ID NO 26
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(5)
<220> FEATURE:
<221> NAME/KEY: 2'-modified-RNA
<222> LOCATION: (6)..(6)
```

```
<220> FEATURE:
<221> NAME/KEY: tc-DNA
<222> LOCATION: (7)..(8)
<220> FEATURE:
<221> NAME/KEY: 2'-modified-RNA
<222> LOCATION: (9)..(9)
<220> FEATURE:
<221> NAME/KEY: tc-DNA
<222> LOCATION: (10)..(15)

<400> SEQUENCE: 26
aagatggcat ttcta                                                          15

<210> SEQ ID NO 27
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(7)
<220> FEATURE:
<221> NAME/KEY: 2'-modified-RNA
<222> LOCATION: (8)..(10)
<220> FEATURE:
<221> NAME/KEY: tc-DNA
<222> LOCATION: (11)..(15)

<400> SEQUENCE: 27
aagatggcau ttcta                                                          15

<210> SEQ ID NO 28
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(3)
<220> FEATURE:
<221> NAME/KEY: 2'-modified-RNA
<222> LOCATION: (4)..(4)
<220> FEATURE:
<221> NAME/KEY: tc-DNA
<222> LOCATION: (5)..(5)
<220> FEATURE:
<221> NAME/KEY: 2'-modified-RNA
<222> LOCATION: (6)..(6)
<220> FEATURE:
<221> NAME/KEY: tc-DNA
<222> LOCATION: (7)..(8)
<220> FEATURE:
<221> NAME/KEY: 2'-modified-RNA
<222> LOCATION: (9)..(9)
<220> FEATURE:
<221> NAME/KEY: tc-DNA
<222> LOCATION: (10)..(15)

<400> SEQUENCE: 28
aagatggcat ttcta                                                          15

<210> SEQ ID NO 29
<211> LENGTH: 15
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
```

```
<221> NAME/KEY: tc-DNA
<222> LOCATION: (1)..(4)
<220> FEATURE:
<221> NAME/KEY: 2'-modified-RNA
<222> LOCATION: (5)..(6)
<220> FEATURE:
<221> NAME/KEY: tc-DNA
<222> LOCATION: (7)..(9)
<220> FEATURE:
<221> NAME/KEY: 2'-modified-RNA
<222> LOCATION: (10)..(10)
<220> FEATURE:
<221> NAME/KEY: tc-DNA
<222> LOCATION: (11)..(15)

<400> SEQUENCE: 29
aagauggcau ttcta                                              15

<210> SEQ ID NO 30
<211> LENGTH: 18
<212> TYPE: DNA
<213> ORGANISM: Artificial Sequence
<220> FEATURE:
<223> OTHER INFORMATION: mixed tc-DNA and 2'-modified-RNA
      oligonucleotide
<220> FEATURE:
<221> NAME/KEY: tc-DNA
<222> LOCATION: (1)..(12)
<220> FEATURE:
<221> NAME/KEY: 2'-modified-RNA
<222> LOCATION: (13)..(17)
<220> FEATURE:
<221> NAME/KEY: tc-DNA
<222> LOCATION: (18)..(18)

<400> SEQUENCE: 30
aggaagatgg cauuucua                                           18

<210> SEQ ID NO 31
<211> LENGTH: 15
<212> TYPE: DNA
<213> ORGANISM: Artificial Sequence
<220> FEATURE:
<223> OTHER INFORMATION: SY-0329; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(4)
<220> FEATURE:
<221> NAME/KEY: tc-DNA
<222> LOCATION: (5)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 31
aagatggcat ttcta                                              15

<210> SEQ ID NO 32
<211> LENGTH: 15
<212> TYPE: DNA
<213> ORGANISM: Artificial Sequence
<220> FEATURE:
<223> OTHER INFORMATION: SY-0330; mixed tc-DNA and 2'-modified-RNA
      oligonucleotide; full phosphorothioate substitution
```

```
<220> FEATURE:
<221> NAME/KEY: tc-DNA
<222> LOCATION: (1)..(4)
<220> FEATURE:
<221> NAME/KEY: 2'-O-Me-RNA
<222> LOCATION: (5)..(5)
<220> FEATURE:
<221> NAME/KEY: tc-DNA
<222> LOCATION: (6)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 32
aagauggcat ttcta                                                    15

<210> SEQ ID NO 33
<211> LENGTH: 15
<212> TYPE: DNA
<213> ORGANISM: Artificial Sequence
<220> FEATURE:
<223> OTHER INFORMATION: SY-0331; mixed tc-DNA and 2'-modified-RNA
      oligonucleotide; full phosphorothioate substitution
<220> FEATURE:
<221> NAME/KEY: tc-DNA
<222> LOCATION: (1)..(5)
<220> FEATURE:
<221> NAME/KEY: 2'-O-Me-RNA
<222> LOCATION: (6)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 33
aagatggcat ttcta                                                    15

<210> SEQ ID NO 34
<211> LENGTH: 15
<212> TYPE: DNA
<213> ORGANISM: Artificial Sequence
<220> FEATURE:
<223> OTHER INFORMATION: SY-0332; mixed tc-DNA and 2'-modified-RNA
      oligonucleotide; full phosphorothioate substitution
<220> FEATURE:
<221> NAME/KEY: tc-DNA
<222> LOCATION: (1)..(7)
<220> FEATURE:
<221> NAME/KEY: 2'-O-Me-RNA
<222> LOCATION: (8)..(8)
<220> FEATURE:
<221> NAME/KEY: tc-DNA
<222> LOCATION: (9)..(15)
<220> FEATURE:
<221> NAME/KEY: modified_base
<222> LOCATION: (13)..(13)
<223> OTHER INFORMATION: m5c

<400> SEQUENCE: 34
aagatggcat ttcta                                                    15
```

```
<210> SEQ ID NO 35
<211> LENGTH: 15
<212> TYPE: DNA
<213> ORGANISM: Artificial Sequence
<220> FEATURE:
<223> OTHER INFORMATION: SY-0333; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(5)
<220> FEATURE:
<221> NAME/KEY: tc-DNA
<222> LOCATION: (6)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 35
aagauggcat ttcta                                                   15

<210> SEQ ID NO 36
<211> LENGTH: 15
<212> TYPE: DNA
<213> ORGANISM: Artificial Sequence
<220> FEATURE:
<223> OTHER INFORMATION: SY-0334; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(4)
<220> FEATURE:
<221> NAME/KEY: tc-DNA
<222> LOCATION: (5)..(5)
<220> FEATURE:
<221> NAME/KEY: 2'-O-Me-RNA
<222> LOCATION: (6)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 36
aagatggcat ttcta                                                   15

<210> SEQ ID NO 37
<211> LENGTH: 15
<212> TYPE: DNA
<213> ORGANISM: Artificial Sequence
<220> FEATURE:
<223> OTHER INFORMATION: SY-0335; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(4)
```

```
<220> FEATURE:
<221> NAME/KEY: tc-DNA
<222> LOCATION: (5)..(7)
<220> FEATURE:
<221> NAME/KEY: 2'-O-Me-RNA
<222> LOCATION: (8)..(8)
<220> FEATURE:
<221> NAME/KEY: tc-DNA
<222> LOCATION: (9)..(15)
<220> FEATURE:
<221> NAME/KEY: modified_base
<222> LOCATION: (13)..(13)
<223> OTHER INFORMATION: m5c

<400> SEQUENCE: 37
aagatggcat ttcta                                                      15

<210> SEQ ID NO 38
<211> LENGTH: 15
<212> TYPE: DNA
<213> ORGANISM: Artificial Sequence
<220> FEATURE:
<223> OTHER INFORMATION: SY-0337; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 38
aagauggcat ttcta                                                      15

<210> SEQ ID NO 39
<211> LENGTH: 15
<212> TYPE: DNA
<213> ORGANISM: Artificial Sequence
<220> FEATURE:
<223> OTHER INFORMATION: SY-0338; mixed tc-DNA and 2'-modified-RNA
      oligonucleotide; full phosphorothioate substitution
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(5)
<220> FEATURE:
<221> NAME/KEY: tc-DNA
<222> LOCATION: (6)..(7)
<220> FEATURE:
<221> NAME/KEY: 2'-O-Me-RNA
<222> LOCATION: (8)..(8)
<220> FEATURE:
<221> NAME/KEY: tc-DNA
<222> LOCATION: (9)..(15)
<220> FEATURE:
<221> NAME/KEY: modified_base
<222> LOCATION: (13)..(13)
<223> OTHER INFORMATION: m5c

<400> SEQUENCE: 39
aagauggcat ttcta                                                      15
```

```
<210> SEQ ID NO 40
<211> LENGTH: 15
<212> TYPE: DNA
<213> ORGANISM: Artificial Sequence
<220> FEATURE:
<223> OTHER INFORMATION: SY-0339; mixed tc-DNA and 2'-modified-RNA
      oligonucleotide; full phosphorothioate substitution
<220> FEATURE:
<221> NAME/KEY: tc-DNA
<222> LOCATION: (1)..(4)
<220> FEATURE:
<221> NAME/KEY: 2'-O-Me-RNA
<222> LOCATION: (5)..(5)
<220> FEATURE:
<221> NAME/KEY: tc-DNA
<222> LOCATION: (6)..(7)
<220> FEATURE:
<221> NAME/KEY: 2'-O-Me-RNA
<222> LOCATION: (8)..(8)
<220> FEATURE:
<221> NAME/KEY: tc-DNA
<222> LOCATION: (9)..(9)
<220> FEATURE:
<221> NAME/KEY: 2'-O-Me-RNA
<222> LOCATION: (10)..(10)
<220> FEATURE:
<221> NAME/KEY: tc-DNA
<222> LOCATION: (11)..(15)
<220> FEATURE:
<221> NAME/KEY: modified_base
<222> LOCATION: (13)..(13)
<223> OTHER INFORMATION: m5c

<400> SEQUENCE: 40
aagauggcau ttcta                                              15

<210> SEQ ID NO 41
<211> LENGTH: 15
<212> TYPE: DNA
<213> ORGANISM: Artificial Sequence
<220> FEATURE:
<223> OTHER INFORMATION: SY-0340; mixed tc-DNA and 2'-modified-RNA
      oligonucleotide; full phosphorothioate substitution
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-O-Me-RNA
<222> LOCATION: (4)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 41
aagauggcat ttcta                                              15

<210> SEQ ID NO 42
<211> LENGTH: 15
<212> TYPE: DNA
```

```
<213> ORGANISM: Artificial Sequence
<220> FEATURE:
<223> OTHER INFORMATION: SY-0341; mixed tc-DNA and 2'-modified-RNA
      oligonucleotide; full phosphorothioate substitution
<220> FEATURE:
<221> NAME/KEY: tc-DNA
<222> LOCATION: (1)..(7)
<220> FEATURE:
<221> NAME/KEY: 2'-O-Me-RNA
<222> LOCATION: (8)..(10)
<220> FEATURE:
<221> NAME/KEY: tc-DNA
<222> LOCATION: (11)..(11)
<220> FEATURE:
<221> NAME/KEY: 2'-O-Me-RNA
<222> LOCATION: (12)..(12)
<220> FEATURE:
<221> NAME/KEY: modified_base
<222> LOCATION: (13)..(13)
<223> OTHER INFORMATION: m5c
<220> FEATURE:
<221> NAME/KEY: tc-DNA
<222> LOCATION: (13)..(15)

<400> SEQUENCE: 42
aagatggcau tucta                                                      15

<210> SEQ ID NO 43
<211> LENGTH: 15
<212> TYPE: DNA
<213> ORGANISM: Artificial Sequence
<220> FEATURE:
<223> OTHER INFORMATION: SY-0371; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-O-Me-RNA
<222> LOCATION: (4)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 43
aagauggcat ttcta                                                      15

<210> SEQ ID NO 44
<211> LENGTH: 15
<212> TYPE: DNA
<213> ORGANISM: Artificial Sequence
<220> FEATURE:
<223> OTHER INFORMATION: SY-0372; mixed tc-DNA and 2'-modified-RNA
      oligonucleotide; mixed phosphorothioate and phosphorodiester
      linkages
<220> FEATURE:
<221> NAME/KEY: modified_base
<222> LOCATION: (8)..(8)
<223> OTHER INFORMATION: m5c
<220> FEATURE:
```

```
<221> NAME/KEY: 2'-O-Me-RNA
<222> LOCATION: (10)..(10)
<220> FEATURE:
<221> NAME/KEY: tc-DNA
<222> LOCATION: (11)..(11)
<220> FEATURE:
<221> NAME/KEY: 2'-O-Me-RNA
<222> LOCATION: (12)..(12)
<220> FEATURE:
<221> NAME/KEY: modified_base
<222> LOCATION: (13)..(13)
<223> OTHER INFORMATION: m5c
<220> FEATURE:
<221> NAME/KEY: tc-DNA
<222> LOCATION: (13)..(13)
<220> FEATURE:
<221> NAME/KEY: 2'-O-Me-RNA
<222> LOCATION: (14)..(14)
<220> FEATURE:
<221> NAME/KEY: tc-DNA
<222> LOCATION: (15)..(15)

<400> SEQUENCE: 44
aagatggcau tucua                                                    15

<210> SEQ ID NO 45
<211> LENGTH: 15
<212> TYPE: DNA
<213> ORGANISM: Artificial Sequence
<220> FEATURE:
<223> OTHER INFORMATION: SY-0373; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(10)
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (11)..(14)
<220> FEATURE:
<221> NAME/KEY: tc-DNA
<222> LOCATION: (15)..(15)

<400> SEQUENCE: 45
gaagatggca uuuct                                                    15

<210> SEQ ID NO 46
<211> LENGTH: 18
<212> TYPE: DNA
<213> ORGANISM: Artificial Sequence
<220> FEATURE:
<223> OTHER INFORMATION: SY-0374; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(12)
<220> FEATURE:
<221> NAME/KEY: modified_base
<222> LOCATION: (11)..(11)
<223> OTHER INFORMATION: m5c
<220> FEATURE:
<221> NAME/KEY: 2'-O-Me-RNA
<222> LOCATION: (13)..(17)
<220> FEATURE:
<221> NAME/KEY: tc-DNA
<222> LOCATION: (18)..(18)

<400> SEQUENCE: 46
aggaagatgg cauuucua                                                 18
```

```
<210> SEQ ID NO 47
<211> LENGTH: 18
<212> TYPE: DNA
<213> ORGANISM: Artificial Sequence
<220> FEATURE:
<223> OTHER INFORMATION: SY-0388; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(10)
<220> FEATURE:
<221> NAME/KEY: 2'-O-Me-RNA
<222> LOCATION: (11)..(15)
<220> FEATURE:
<221> NAME/KEY: modified_base
<222> LOCATION: (16)..(16)
<223> OTHER INFORMATION: m5c
<220> FEATURE:
<221> NAME/KEY: tc-DNA
<222> LOCATION: (16)..(18)

<400> SEQUENCE: 47
aggaagatgg cauuucta                                                 18

<210> SEQ ID NO 48
<211> LENGTH: 18
<212> TYPE: DNA
<213> ORGANISM: Artificial Sequence
<220> FEATURE:
<223> OTHER INFORMATION: SY-0389; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(10)
<220> FEATURE:
<221> NAME/KEY: 2'-O-Me-RNA
<222> LOCATION: (11)..(17)
<220> FEATURE:
<221> NAME/KEY: tc-DNA
<222> LOCATION: (18)..(18)

<400> SEQUENCE: 48
aggaagatgg cauuucua                                                 18

<210> SEQ ID NO 49
<211> LENGTH: 18
<212> TYPE: DNA
<213> ORGANISM: Artificial Sequence
<220> FEATURE:
<223> OTHER INFORMATION: SY-0390; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-O-Me-RNA
<222> LOCATION: (4)..(6)
<220> FEATURE:
<221> NAME/KEY: tc-DNA
<222> LOCATION: (7)..(18)
<220> FEATURE:
<221> NAME/KEY: modified_base
<222> LOCATION: (8)..(8)
<223> OTHER INFORMATION: m5c
```

```
<220> FEATURE:
<221> NAME/KEY: modified_base
<222> LOCATION: (13)..(13)
<223> OTHER INFORMATION: m5c

<400> SEQUENCE: 49
aagauggcat ttctagtt                                                  18

<210> SEQ ID NO 50
<211> LENGTH: 18
<212> TYPE: DNA
<213> ORGANISM: Artificial Sequence
<220> FEATURE:
<223> OTHER INFORMATION: SY-0391; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(6)
<220> FEATURE:
<221> NAME/KEY: tc-DNA
<222> LOCATION: (7)..(18)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 50
aagauggcat ttctagtt                                                  18

<210> SEQ ID NO 51
<211> LENGTH: 18
<212> TYPE: DNA
<213> ORGANISM: Artificial Sequence
<220> FEATURE:
<223> OTHER INFORMATION: SY-0392; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(2)
<220> FEATURE:
<221> NAME/KEY: 2'-O-Me-RNA
<222> LOCATION: (3)..(6)
<220> FEATURE:
<221> NAME/KEY: tc-DNA
<222> LOCATION: (7)..(18)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 51
aagauggcat ttctagtt                                                  18

<210> SEQ ID NO 52
<211> LENGTH: 18
<212> TYPE: DNA
<213> ORGANISM: Artificial Sequence
<220> FEATURE:
<223> OTHER INFORMATION: SY-0393; mixed tc-DNA and 2'-modified-RNA
      oligonucleotide; mixed phosphorothioate and phosphorodiester
```

```
            linkages
<220> FEATURE:
<221> NAME/KEY: tc-DNA
<222> LOCATION: (1)..(6)
<220> FEATURE:
<221> NAME/KEY: 2'-O-Me-RNA
<222> LOCATION: (7)..(9)
<220> FEATURE:
<221> NAME/KEY: tc-DNA
<222> LOCATION: (10)..(18)
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(16)
<223> OTHER INFORMATION: m5c

<400> SEQUENCE: 52
aggaagaugg catttcta                                                   18

<210> SEQ ID NO 53
<211> LENGTH: 18
<212> TYPE: DNA
<213> ORGANISM: Artificial Sequence
<220> FEATURE:
<223> OTHER INFORMATION: SY-0394; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(4)
<220> FEATURE:
<221> NAME/KEY: 2'-O-Me-RNA
<222> LOCATION: (5)..(9)
<220> FEATURE:
<221> NAME/KEY: tc-DNA
<222> LOCATION: (10)..(18)
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (16)..(16)
<223> OTHER INFORMATION: m5c

<400> SEQUENCE: 53
aggaagaugg catttcta                                                   18

<210> SEQ ID NO 54
<211> LENGTH: 17
<212> TYPE: DNA
<213> ORGANISM: Artificial Sequence
<220> FEATURE:
<223> OTHER INFORMATION: SY-0395; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(8)
<220> FEATURE:
<221> NAME/KEY: tc-DNA
<222> LOCATION: (9)..(17)
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (15)..(15)
```

-continued

```
<223> OTHER INFORMATION: m5c

<400> SEQUENCE: 54
ggaagauggc atttcta                                                    17

<210> SEQ ID NO 55
<211> LENGTH: 16
<212> TYPE: DNA
<213> ORGANISM: Artificial Sequence
<220> FEATURE:
<223> OTHER INFORMATION: SY-0396; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(3)
<220> FEATURE:
<221> NAME/KEY: 2'-O-Me-RNA
<222> LOCATION: (4)..(8)
<220> FEATURE:
<221> NAME/KEY: tc-DNA
<222> LOCATION: (9)..(16)
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (15)..(15)
<223> OTHER INFORMATION: m5c

<400> SEQUENCE: 55
ggaagauggc atttct                                                     16

<210> SEQ ID NO 56
<211> LENGTH: 18
<212> TYPE: DNA
<213> ORGANISM: Artificial Sequence
<220> FEATURE:
<223> OTHER INFORMATION: SY-0397; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(5)
<220> FEATURE:
<221> NAME/KEY: 2'-O-Me-RNA
<222> LOCATION: (6)..(10)
<220> FEATURE:
<221> NAME/KEY: modified_base
<222> LOCATION: (11)..(11)
<223> OTHER INFORMATION: m5c
<220> FEATURE:
<221> NAME/KEY: tc-DNA
<222> LOCATION: (11)..(18)
<220> FEATURE:
<221> NAME/KEY: modified_base
<222> LOCATION: (16)..(16)
<223> OTHER INFORMATION: m5c

<400> SEQUENCE: 56
aggaagaugg catttcta                                                   18

<210> SEQ ID NO 57
<211> LENGTH: 18
<212> TYPE: DNA
<213> ORGANISM: Artificial Sequence
<220> FEATURE:
<223> OTHER INFORMATION: SY-0398; mixed tc-DNA and 2'-modified-RNA
      oligonucleotide; mixed phosphorothioate and phosphorodiester
      linkages
<220> FEATURE:
<221> NAME/KEY: tc-DNA
```

```
<222> LOCATION: (1)..(4)
<220> FEATURE:
<221> NAME/KEY: 2'-O-Me-RNA
<222> LOCATION: (5)..(10)
<220> FEATURE:
<221> NAME/KEY: modified_base
<222> LOCATION: (11)..(11)
<223> OTHER INFORMATION: m5c
<220> FEATURE:
<221> NAME/KEY: tc-DNA
<222> LOCATION: (11)..(18)
<220> FEATURE:
<221> NAME/KEY: modified_base
<222> LOCATION: (16)..(16)
<223> OTHER INFORMATION: m5c

<400> SEQUENCE: 57
aggaagaugg catttcta                                                 18

<210> SEQ ID NO 58
<211> LENGTH: 17
<212> TYPE: DNA
<213> ORGANISM: Artificial Sequence
<220> FEATURE:
<223> OTHER INFORMATION: SY-0406; mixed tc-DNA and 2'-modified-RNA
      oligonucleotide; mixed phosphorothioate and phosphorodiester
      linkages
<220> FEATURE:
<221> NAME/KEY: tc-DNA
<222> LOCATION: (1)..(10)
<220> FEATURE:
<221> NAME/KEY: 2'-O-Me-RNA
<222> LOCATION: (11)..(17)

<400> SEQUENCE: 58
aggaagatgg cauuucu                                                  17

<210> SEQ ID NO 59
<211> LENGTH: 17
<212> TYPE: DNA
<213> ORGANISM: Artificial Sequence
<220> FEATURE:
<223> OTHER INFORMATION: SY-0405; mixed tc-DNA and 2'-modified-RNA
      oligonucleotide; mixed phosphorothioate and phosphorodiester
      linkages
<220> FEATURE:
<221> NAME/KEY: 2'-O-Me-RNA
<222> LOCATION: (1)..(5)
<223> OTHER INFORMATION: m5c
<220> FEATURE:
<221> NAME/KEY: tc-DNA
<222> LOCATION: (6)..(17)
<223> OTHER INFORMATION: m5c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 59
agauggcatt tctagtt                                                  17

<210> SEQ ID NO 60
<211> LENGTH: 15
<212> TYPE: DNA
<213> ORGANISM: Artificial Sequence
<220> FEATURE:
<223> OTHER INFORMATION: SY-0407; mixed tc-DNA and 2'-modified-RNA
      oligonucleotide; mixed phosphorothioate and phosphorodiester
      linkages
```

```
<220> FEATURE:
<221> NAME/KEY: 2'-O-Me-RNA
<222> LOCATION: (5)..(5)
<223> OTHER INFORMATION: m5c
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 60
aagauggcat ttcta                                                    15

<210> SEQ ID NO 61
<211> LENGTH: 15
<212> TYPE: DNA
<213> ORGANISM: Artificial Sequence
<220> FEATURE:
<223> OTHER INFORMATION: SY-0408; mixed tc-DNA and 2'-modified-RNA
      oligonucleotide; mixed phosphorothioate and phosphorodiester
      linkages
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 2'-O-Me-RNA
<222> LOCATION: (5)..(5)

<400> SEQUENCE: 61
aagauggcat ttcta                                                    15

<210> SEQ ID NO 62
<211> LENGTH: 15
<212> TYPE: DNA
<213> ORGANISM: Artificial Sequence
<220> FEATURE:
<223> OTHER INFORMATION: SY-0410; mixed tc-DNA and 2'-modified-RNA
      oligonucleotide; mixed phosphorothioate and phosphorodiester
      linkages
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 2'-O-Me-RNA
<222> LOCATION: (5)..(5)

<400> SEQUENCE: 62
aagauggcat ttcta                                                    15

<210> SEQ ID NO 63
<211> LENGTH: 15
<212> TYPE: DNA
<213> ORGANISM: Artificial Sequence
<220> FEATURE:
<223> OTHER INFORMATION: SY-0412; mixed tc-DNA and 2'-modified-RNA
      oligonucleotide; mixed phosphorothioate and phosphorodiester
      linkages
<220> FEATURE:
```

```
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 2'-O-Me-RNA
<222> LOCATION: (5)..(5)

<400> SEQUENCE: 63
aagauggcat ttcta                                              15

<210> SEQ ID NO 64
<211> LENGTH: 15
<212> TYPE: DNA
<213> ORGANISM: Artificial Sequence
<220> FEATURE:
<223> OTHER INFORMATION: SY-0414; mixed tc-DNA and 2'-modified-RNA
      oligonucleotide; mixed phosphorothioate and phosphorodiester
      linkages
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 2'-O-Me-RNA
<222> LOCATION: (5)..(5)

<400> SEQUENCE: 64
aagauggcat ttcta                                              15

<210> SEQ ID NO 65
<211> LENGTH: 15
<212> TYPE: DNA
<213> ORGANISM: Artificial Sequence
<220> FEATURE:
<223> OTHER INFORMATION: SY-0416; mixed tc-DNA and 2'-modified-RNA
      oligonucleotide; mixed phosphorothioate and phosphorodiester
      linkages
<220> FEATURE:
<221> NAME/KEY: 1,3-propanediol
<222> LOCATION: (1)..(1)
<220> FEATURE:
```

```
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 1,3-propanediol
<222> LOCATION: (1)..(1)
<220> FEATURE:
<221> NAME/KEY: 2'-O-Me-RNA
<222> LOCATION: (5)..(5)

<400> SEQUENCE: 65
aagauggcat ttcta                                                    15

<210> SEQ ID NO 66
<211> LENGTH: 15
<212> TYPE: DNA
<213> ORGANISM: Artificial Sequence
<220> FEATURE:
<223> OTHER INFORMATION: SY-0417; mixed tc-DNA and 2'-modified-RNA
      oligonucleotide; mixed phosphorothioate and phosphorodiester
      linkages
<220> FEATURE:
<221> NAME/KEY: modified_base
<222> LOCATION: (8)..(8)
<223> OTHER INFORMATION: m5c
<220> FEATURE:
<221> NAME/KEY: 2'-O-Me-RNA
<222> LOCATION: (10)..(10)
<220> FEATURE:
<221> NAME/KEY: modified_base
<222> LOCATION: (13)..(13)
<223> OTHER INFORMATION: m5c

<400> SEQUENCE: 66
aagatggcau ttcta                                                    15

<210> SEQ ID NO 67
<211> LENGTH: 15
<212> TYPE: DNA
<213> ORGANISM: Artificial Sequence
<220> FEATURE:
<223> OTHER INFORMATION: SY-0418; mixed tc-DNA and 2'-modified-RNA
      oligonucleotide; mixed phosphorothioate and phosphorodiester
      linkages
<220> FEATURE:
<221> NAME/KEY: modified_base
<222> LOCATION: (8)..(8)
<223> OTHER INFORMATION: m5c
<220> FEATURE:
<221> NAME/KEY: 2'-O-Me-RNA
<222> LOCATION: (9)..(9)
<220> FEATURE:
<221> NAME/KEY: modified_base
<222> LOCATION: (13)..(13)
<223> OTHER INFORMATION: m5c
```

```
<400> SEQUENCE: 67
aagatggcat ttcta                                          15

<210> SEQ ID NO 68
<211> LENGTH: 15
<212> TYPE: DNA
<213> ORGANISM: Artificial Sequence
<220> FEATURE:
<223> OTHER INFORMATION: SYN51 (Syn15-mer HEX51 (+67+81)
<220> FEATURE:
<221> NAME/KEY: tc-DNA
<222> LOCATION: (1)..(15)

<400> SEQUENCE: 68
aagatggcat ttcta                                          15

<210> SEQ ID NO 69
<211> LENGTH: 13
<212> TYPE: DNA
<213> ORGANISM: Artificial Sequence
<220> FEATURE:
<223> OTHER INFORMATION: Syn13-mer HEX51 (+68+80)
<220> FEATURE:
<221> NAME/KEY: tc-DNA
<222> LOCATION: (1)..(13)

<400> SEQUENCE: 69
agatggcatt tct                                            13

<210> SEQ ID NO 70
<211> LENGTH: 13
<212> TYPE: DNA
<213> ORGANISM: Artificial Sequence
<220> FEATURE:
<223> OTHER INFORMATION: SY-0206 SYN 13-mer
<220> FEATURE:
<221> NAME/KEY: tc-DNA
<222> LOCATION: (1)..(13)

<400> SEQUENCE: 70
agatggcatt tct                                            13

<210> SEQ ID NO 71
<211> LENGTH: 13
<212> TYPE: DNA
<213> ORGANISM: Artificial Sequence
<220> FEATURE:
<223> OTHER INFORMATION: M23D 13-mer
<220> FEATURE:
<221> NAME/KEY: tc-DNA
<222> LOCATION: (1)..(13)

<400> SEQUENCE: 71
cctcggctta cct                                            13

<210> SEQ ID NO 72
<211> LENGTH: 15
<212> TYPE: DNA
<213> ORGANISM: Artificial Sequence
<220> FEATURE:
<223> OTHER INFORMATION: SY-0208 SYN 15-mer
<220> FEATURE:
<221> NAME/KEY: tc-DNA
<222> LOCATION: (1)..(15)

<400> SEQUENCE: 72
aagatggcat ttcta                                          15
```

```
<210> SEQ ID NO 73
<211> LENGTH: 15
<212> TYPE: DNA
<213> ORGANISM: Artificial Sequence
<220> FEATURE:
<223> OTHER INFORMATION: SY-0336 complement to SYN 13-mer
<220> FEATURE:
<221> NAME/KEY: tc-DNA
<222> LOCATION: (1)..(15)

<400> SEQUENCE: 73
tagaaatgcc atctt                                                    15

<210> SEQ ID NO 74
<211> LENGTH: 15
<212> TYPE: DNA
<213> ORGANISM: Artificial Sequence
<220> FEATURE:
<223> OTHER INFORMATION: SY-0219 15-mer HEX51 (+97;+111)
<220> FEATURE:
<221> NAME/KEY: tc-DNA
<222> LOCATION: (1)..(15)

<400> SEQUENCE: 74
ctgccagagc aggta                                                    15

<210> SEQ ID NO 75
<211> LENGTH: 18
<212> TYPE: DNA
<213> ORGANISM: Artificial Sequence
<220> FEATURE:
<223> OTHER INFORMATION: SY-0375 Hex51 (+66;+83) 2-OMe 17
<220> FEATURE:
<221> NAME/KEY: tc-DNA
<222> LOCATION: (1)..(12)
<220> FEATURE:
<221> NAME/KEY: modified_base
<222> LOCATION: (11)..(11)
<223> OTHER INFORMATION: m5c
<220> FEATURE:
<221> NAME/KEY: 2'-O-Me-RNA
<222> LOCATION: (13)..(17)
<220> FEATURE:
<221> NAME/KEY: tc-DNA
<222> LOCATION: (18)..(18)

<400> SEQUENCE: 75
aggaagatgg cauuucua                                                 18

<210> SEQ ID NO 76
<211> LENGTH: 15
<212> TYPE: DNA
<213> ORGANISM: Artificial Sequence
<220> FEATURE:
<223> OTHER INFORMATION: SY-0376 Biot-Hex51 (+67;+81) 2-OMe 11; mixed
      tc-DNA and 2'-modified-RNA oligonucleotide; mixed phosphorothioate
      and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-O-Me-RNA
```

```
<222> LOCATION: (4)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 76
aagauggcat ttcta                                                          15

<210> SEQ ID NO 77
<211> LENGTH: 15
<212> TYPE: DNA
<213> ORGANISM: Artificial Sequence
<220> FEATURE:
<223> OTHER INFORMATION: SY-0377 Biot-Hex51 (+67;+81) 2-OMe 13 (6Sb5);
      mixed tc-DNA and 2'-modified-RNA oligonucleotide; mixed
      phosphorothioate and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(1)
<220> FEATURE:
<221> NAME/KEY: 2'-O-Me-RNA
<222> LOCATION: (2)..(2)
<220> FEATURE:
<221> NAME/KEY: tc-DNA
<222> LOCATION: (3)..(3)
<220> FEATURE:
<221> NAME/KEY: 2'-O-Me-RNA
<222> LOCATION: (4)..(6)
<220> FEATURE:
<221> NAME/KEY: tc-DNA
<222> LOCATION: (7)..(15)
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 77
aagauggcat ttcta                                                          15

<210> SEQ ID NO 78
<211> LENGTH: 15
<212> TYPE: DNA
<213> ORGANISM: Artificial Sequence
<220> FEATURE:
<223> OTHER INFORMATION: SY-0378 Biot-Hex51 (+67;+81) 2-OMe 14 (6Sb3);
      mixed tc-DNA and 2'-modified-RNA oligonucleotide; mixed
      phosphorothioate and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(9)
<220> FEATURE:
<221> NAME/KEY: modified_base
<222> LOCATION: (8)..(8)
<223> OTHER INFORMATION: m5c
<220> FEATURE:
<221> NAME/KEY: 2'-O-Me-RNA
<222> LOCATION: (10)..(10)
```

```
<220> FEATURE:
<221> NAME/KEY: tc-DNA
<222> LOCATION: (11)..(11)
<220> FEATURE:
<221> NAME/KEY: 2'-O-Me-RNA
<222> LOCATION: (12)..(12)
<220> FEATURE:
<221> NAME/KEY: modified_base
<222> LOCATION: (13)..(13)
<223> OTHER INFORMATION: m5c
<220> FEATURE:
<221> NAME/KEY: tc-DNA
<222> LOCATION: (13)..(13)
<220> FEATURE:
<221> NAME/KEY: 2'-O-Me-RNA
<222> LOCATION: (14)..(14)
<220> FEATURE:
<221> NAME/KEY: tc-DNA
<222> LOCATION: (15)..(15)

<400> SEQUENCE: 78
aagatggcau tucua                                                        15

<210> SEQ ID NO 79
<211> LENGTH: 15
<212> TYPE: DNA
<213> ORGANISM: Artificial Sequence
<220> FEATURE:
<223> OTHER INFORMATION: SY-0379 Biot-Hex51 (+67;+81) 2-OMe 15 (5Sb3);
      mixed tc-DNA and 2'-modified-RNA oligonucleotide; mixed
      phosphorothioate and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(10)
<220> FEATURE:
<221> NAME/KEY: modified_base
<222> LOCATION: (8)..(8)
<223> OTHER INFORMATION: m5c
<220> FEATURE:
<221> NAME/KEY: 2'-O-Me-RNA
<222> LOCATION: (11)..(14)
<220> FEATURE:
<221> NAME/KEY: tc-DNA
<222> LOCATION: (15)..(15)

<400> SEQUENCE: 79
gaagatggca uuuct                                                        15

<210> SEQ ID NO 80
<211> LENGTH: 18
<212> TYPE: DNA
<213> ORGANISM: Artificial Sequence
<220> FEATURE:
<223> OTHER INFORMATION: SY-0380 Biot-Hex51 (+66;+83) 2-OMe 16 (6Sb3);
      mixed tc-DNA and 2'-modified-RNA oligonucleotide; mixed
      phosphorothioate and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(12)
<220> FEATURE:
<221> NAME/KEY: modified_base
<222> LOCATION: (11)..(11)
<223> OTHER INFORMATION: m5c
<220> FEATURE:
<221> NAME/KEY: 2'-O-Me-RNA
<222> LOCATION: (13)..(17)
<223> OTHER INFORMATION: m5c
<220> FEATURE:
<221> NAME/KEY: tc-DNA
```

-continued

```
<222> LOCATION: (18)..(18)
<223> OTHER INFORMATION: m5c

<400> SEQUENCE: 80
aggaagatgg cauuucua                                                 18

<210> SEQ ID NO 81
<211> LENGTH: 18
<212> TYPE: DNA
<213> ORGANISM: Artificial Sequence
<220> FEATURE:
<223> OTHER INFORMATION: SY-0381 Biot-Hex51 (+66;+83) 2-OMe 17; mixed
      tc-DNA and 2'-modified-RNA oligonucleotide; mixed phosphorothioate
      and phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(12)
<220> FEATURE:
<221> NAME/KEY: modified_base
<222> LOCATION: (11)..(11)
<223> OTHER INFORMATION: m5c
<220> FEATURE:
<221> NAME/KEY: 2'-O-Me-RNA
<222> LOCATION: (13)..(17)
<220> FEATURE:
<221> NAME/KEY: tc-DNA
<222> LOCATION: (18)..(18)

<400> SEQUENCE: 81
aggaagatgg cauuucua                                                 18

<210> SEQ ID NO 82
<211> LENGTH: 15
<212> TYPE: DNA
<213> ORGANISM: Artificial Sequence
<220> FEATURE:
<223> OTHER INFORMATION: SY-0382 M23D-15m (2OMe 5Sb3); mixed tc-DNA and
      2'-modified-RNA oligonucleotide; mixed phosphorothioate and
      phosphorodiester linkages
<220> FEATURE:
<221> NAME/KEY: tc-DNA
<222> LOCATION: (1)..(10)
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (11)..(14)
<220> FEATURE:
<221> NAME/KEY: tc-DNA
<222> LOCATION: (15)..(15)

<400> SEQUENCE: 82
aacctcggct uacct                                                    15

<210> SEQ ID NO 83
<211> LENGTH: 15
<212> TYPE: DNA
<213> ORGANISM: Artificial Sequence
<220> FEATURE:
<223> OTHER INFORMATION: SY-0383 M23D-15m (2OMe 4Sb3); mixed tc-DNA and
```

2'-modified-RNA oligonucleotide; mixed phosphorothioate and
        phosphorodiester linkages
<220> FEATURE:
<221> NAME/KEY: tc-DNA
<222> LOCATION: (1)..(11)
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (12)..(14)
<220> FEATURE:
<221> NAME/KEY: tc-DNA
<222> LOCATION: (15)..(15)

<400> SEQUENCE: 83
aacctcggct tacct                                                        15

<210> SEQ ID NO 84
<211> LENGTH: 15
<212> TYPE: DNA
<213> ORGANISM: Artificial Sequence
<220> FEATURE:
<223> OTHER INFORMATION: SY-0384 M23D-15m (2OMe 3Sb3); mixed tc-DNA and
        2'-modified-RNA oligonucleotide; mixed phosphorothioate and
        phosphorodiester linkages
<220> FEATURE:
<221> NAME/KEY: tc-DNA
<222> LOCATION: (1)..(12)
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (13)..(14)
<220> FEATURE:
<221> NAME/KEY: tc-DNA
<222> LOCATION: (15)..(15)

<400> SEQUENCE: 84
aacctcggct tacct                                                        15

<210> SEQ ID NO 85
<211> LENGTH: 15
<212> TYPE: DNA
<213> ORGANISM: Artificial Sequence
<220> FEATURE:
<223> OTHER INFORMATION: SY-0385 Biot-M23D-15m (2OMe 5Sb3); mixed tc-DNA
        and 2'-modified-RNA oligonucleotide; mixed phosphorothioate and
        phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(10)
<220> FEATURE:

```
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (11)..(14)
<220> FEATURE:
<221> NAME/KEY: tc-DNA
<222> LOCATION: (15)..(15)

<400> SEQUENCE: 85
aacctcggct uacct                                                     15

<210> SEQ ID NO 86
<211> LENGTH: 15
<212> TYPE: DNA
<213> ORGANISM: Artificial Sequence
<220> FEATURE:
<223> OTHER INFORMATION: SY-0386 Biot-M23D-15m (2OMe 4Sb3); mixed tc-DNA
      and 2'-modified-RNA oligonucleotide; mixed phosphorothioate and
      phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(11)
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (12)..(14)
<220> FEATURE:
<221> NAME/KEY: tc-DNA
<222> LOCATION: (15)..(15)

<400> SEQUENCE: 86
aacctcggct tacct                                                     15

<210> SEQ ID NO 87
<211> LENGTH: 15
<212> TYPE: DNA
<213> ORGANISM: Artificial Sequence
<220> FEATURE:
<223> OTHER INFORMATION: SY-0387 Biot-M23D-15m (2OMe 3Sb3); mixed tc-DNA
      and 2'-modified-RNA oligonucleotide; mixed phosphorothioate and
      phosphorodiester linkages
<220> FEATURE:
<221> NAME/KEY: biotin
<222> LOCATION: (1)..(1)
<220> FEATURE:
<221> NAME/KEY: tc-DNA
<222> LOCATION: (1)..(12)
<220> FEATURE:
<221> NAME/KEY: modified_base
<222> LOCATION: (3)..(4)
<223> OTHER INFORMATION: m5c
```

-continued

```
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: 2'-O-Me-RNA
<222> LOCATION: (13)..(14)
<220> FEATURE:
<221> NAME/KEY: tc-DNA
<222> LOCATION: (15)..(15)

<400> SEQUENCE: 87
aacctcggct tacct                                                         15

<210> SEQ ID NO 88
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (4)..(5)
<223> OTHER INFORMATION: m5c
<220> FEATURE:
<221> NAME/KEY: modified_base
<222> LOCATION: (13)..(14)
<223> OTHER INFORMATION: m5c

<400> SEQUENCE: 88
catcctggag ttcct                                                         15

<210> SEQ ID NO 89
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(7)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (8)..(8)
<223> OTHER INFORMATION: 2'-O-methyl-RNA nucleoside (2'-O-Me-RNA)
<220> FEATURE:
<221> NAME/KEY: misc_feature
```

```
<222> LOCATION: (9)..(15)
<223> OTHER INFORMATION: tricyclic DNA nucleoside (tc-DNA)
<220> FEATURE:
<221> NAME/KEY: modified_base
<222> LOCATION: (13)..(14)
<223> OTHER INFORMATION: m5c

<400> SEQUENCE: 89
catcctggag ttcct                                                    15

<210> SEQ ID NO 90
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (6)..(7)
<223> OTHER INFORMATION: m5c
<220> FEATURE:
<221> NAME/KEY: modified_base
<222> LOCATION: (15)..(15)
<223> OTHER INFORMATION: m5c

<400> SEQUENCE: 90
gccatcctgg agttc                                                    15

<210> SEQ ID NO 91
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (6)..(7)
<223> OTHER INFORMATION: m5c
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)
<220> FEATURE:
<221> NAME/KEY: modified_base
<222> LOCATION: (15)..(15)
<223> OTHER INFORMATION: m5c
```

```
<400> SEQUENCE: 91
gccatcctgg agttc                                                        15

<210> SEQ ID NO 92
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(2)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(9)
<223> OTHER INFORMATION: m5c
<220> FEATURE:
<221> NAME/KEY: modified_base
<222> LOCATION: (14)..(15)
<223> OTHER INFORMATION: m5c

<400> SEQUENCE: 92
ccgctgccca atgcc                                                        15

<210> SEQ ID NO 93
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (9)..(11)
<223> OTHER INFORMATION: m5c

<400> SEQUENCE: 93
tgccgctgcc caatg                                                        15

<210> SEQ ID NO 94
<211> LENGTH: 15
<212> TYPE: DNA
<213> ORGANISM: Artificial Sequence
<220> FEATURE:
<223> OTHER INFORMATION: Synthetic
```

```
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (9)..(10)
<223> OTHER INFORMATION: m5c

<400> SEQUENCE: 94
ctggagttcc tgtaa                                                     15

<210> SEQ ID NO 95
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(3)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: misc_feature
<222> LOCATION: (4)..(4)
<223> OTHER INFORMATION: 2'-O-methyl-RNA nucleoside (2'-O-Me-RNA)
<220> FEATURE:
<221> NAME/KEY: misc_feature
<222> LOCATION: (5)..(15)
<223> OTHER INFORMATION: tricyclic DNA nucleoside (tc-DNA)
<220> FEATURE:
<221> NAME/KEY: modified_base
<222> LOCATION: (9)..(10)
<223> OTHER INFORMATION: m5c

<400> SEQUENCE: 95
ctggagttcc tgtaa                                                     15

<210> SEQ ID NO 96
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (11)..(12)
```

<223> OTHER INFORMATION: m5c

<400> SEQUENCE: 96
tcctggagtt cctgt                                                          15

<210> SEQ ID NO 97
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(3)
<223> OTHER INFORMATION: m5c
<220> FEATURE:
<221> NAME/KEY: misc_feature
<222> LOCATION: (6)..(6)
<223> OTHER INFORMATION: 2'-O-methyl-RNA nucleoside (2'-O-Me-RNA)
<220> FEATURE:
<221> NAME/KEY: misc_feature
<222> LOCATION: (7)..(15)
<223> OTHER INFORMATION: tricyclic DNA nucleoside (tc-DNA)
<220> FEATURE:
<221> NAME/KEY: modified_base
<222> LOCATION: (10)..(11)
<223> OTHER INFORMATION: m5c

<400> SEQUENCE: 97
tcctggagtt cctgt                                                          15

<210> SEQ ID NO 98
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(2)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (8)..(10)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 98
acttcatccc actga                                                          15

-continued

```
<210> SEQ ID NO 99
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (5)..(5)
<223> OTHER INFORMATION: 2'-O-methyl-RNA nucleoside (2'-O-Me-RNA)
<220> FEATURE:
<221> NAME/KEY: misc_feature
<222> LOCATION: (6)..(15)
<223> OTHER INFORMATION: tricyclic DNA nucleoside (tc-DNA)
<220> FEATURE:
<221> NAME/KEY: modified_base
<222> LOCATION: (8)..(10)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 99
acttcatccc actga                                                   15

<210> SEQ ID NO 100
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 100
atttcattca actgt                                                   15

<210> SEQ ID NO 101
<211> LENGTH: 15
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<222> LOCATION: (1)..(15)
<223> OTHER INFORMATION: 2'-O-methyl-RNA nucleoside (2'-O-Me-RNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (6)..(6)
<223> OTHER INFORMATION: m5c
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (15)..(15)
<223> OTHER INFORMATION: m5c

<400> SEQUENCE: 101
gtgttcttgt acttc                                                    15

<210> SEQ ID NO 102
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (11)..(11)
<223> OTHER INFORMATION: 2'-O-methyl-RNA nucleoside (2'-O-Me-RNA)
<220> FEATURE:
<221> NAME/KEY: modified_base
<222> LOCATION: (12)..(12)
<223> OTHER INFORMATION: m5c
<220> FEATURE:
<221> NAME/KEY: misc_feature
<222> LOCATION: (12)..(15)
<223> OTHER INFORMATION: tricyclic DNA nucleoside (tc-DNA)
<220> FEATURE:
<221> NAME/KEY: modified_base
<222> LOCATION: (15)..(15)
<223> OTHER INFORMATION: m5c

<400> SEQUENCE: 102
gtgttcttgt acttc                                                    15

<210> SEQ ID NO 103
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)

```
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (12)..(12)
<223> OTHER INFORMATION: m5c

<400> SEQUENCE: 103
ctgaaggtgt tcttg                                                    15

<210> SEQ ID NO 104
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(4)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: misc_feature
<222> LOCATION: (5)..(5)
<223> OTHER INFORMATION: 2'-O-methyl-RNA nucleoside (2'-O-Me-RNA)
<220> FEATURE:
<221> NAME/KEY: misc_feature
<222> LOCATION: (6)..(15)
<223> OTHER INFORMATION: tricyclic DNA nucleoside (tc-DNA)
<220> FEATURE:
<221> NAME/KEY: modified_base
<222> LOCATION: (12)..(12)
<223> OTHER INFORMATION: m5c

<400> SEQUENCE: 104
ctgaaggtgt tcttg                                                    15

<210> SEQ ID NO 105
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (3)..(4)
<223> OTHER INFORMATION: m5c
<220> FEATURE:
<221> NAME/KEY: modified_base
<222> LOCATION: (9)..(9)
<223> OTHER INFORMATION: m5c

<400> SEQUENCE: 105
```
ctccggttct gaagg                                              15

<210> SEQ ID NO 106
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(8)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (3)..(4)
<223> OTHER INFORMATION: m5c
<220> FEATURE:
<221> NAME/KEY: misc_feature
<222> LOCATION: (9)..(9)
<223> OTHER INFORMATION: 2'-O-methyl-RNA nucleoside (2'-O-Me-RNA)
<220> FEATURE:
<221> NAME/KEY: misc_feature
<222> LOCATION: (10)..(15)
<223> OTHER INFORMATION: tricyclic DNA nucleoside (tc-DNA)

<400> SEQUENCE: 106
ctccggttct gaagg                                              15

<210> SEQ ID NO 107
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (7)..(8)
<223> OTHER INFORMATION: m5c
<220> FEATURE:
<221> NAME/KEY: modified_base
<222> LOCATION: (14)..(14)
<223> OTHER INFORMATION: m5c

<400> SEQUENCE: 107
ttgaatcctt taaca                                              15

<210> SEQ ID NO 108
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature

```
<222> LOCATION: (1)..(15)
<223> OTHER INFORMATION: phosphorothioate linkages
<220> FEATURE:
<221> NAME/KEY: modified_base
<222> LOCATION: (7)..(8)
<223> OTHER INFORMATION: m5c
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)
<220> FEATURE:
<221> NAME/KEY: modified_base
<222> LOCATION: (14)..(14)
<223> OTHER INFORMATION: m5c

<400> SEQUENCE: 108
ttgaatcctu taaca                                                    15

<210> SEQ ID NO 109
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(15)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 109
ctttcataat gctgg                                                    15

<210> SEQ ID NO 110
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(5)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (5)..(5)
<223> OTHER INFORMATION: m5c
<220> FEATURE:
```

```
<221> NAME/KEY: misc_feature
<222> LOCATION: (6)..(6)
<223> OTHER INFORMATION: 2'-O-methyl-RNA nucleoside (2'-O-Me-RNA)
<220> FEATURE:
<221> NAME/KEY: misc_feature
<222> LOCATION: (7)..(15)
<223> OTHER INFORMATION: tricyclic DNA nucleoside (tc-DNA)
<220> FEATURE:
<221> NAME/KEY: modified_base
<222> LOCATION: (12)..(12)
<223> OTHER INFORMATION: m5c

<400> SEQUENCE: 110
ctttcataat gctgg                                                    15

<210> SEQ ID NO 111
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature
<222> LOCATION: (1)..(15)
<223> OTHER INFORMATION: phosphorothioate linkages
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)
<220> FEATURE:
<221> NAME/KEY: modified_base
<222> LOCATION: (12)..(12)
<223> OTHER INFORMATION: m5c

<400> SEQUENCE: 111
ctttcataau gctgg                                                    15

<210> SEQ ID NO 112
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 112
catcctggag ttcct                                                    15

<210> SEQ ID NO 113
<211> LENGTH: 15
<212> TYPE: DNA
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (1)..(7)
<223> OTHER INFORMATION: tricyclic DNA nucleoside (tc-DNA)
<220> FEATURE:
<221> NAME/KEY: misc_feature
<222> LOCATION: (8)..(8)
<223> OTHER INFORMATION: 2'-O-methyl-RNA nucleoside (2'-O-Me-RNA)
<220> FEATURE:
<221> NAME/KEY: misc_feature
<222> LOCATION: (9)..(15)
<223> OTHER INFORMATION: tricyclic DNA nucleoside (tc-DNA)

<400> SEQUENCE: 113
catcctggag ttcct                                                          15

<210> SEQ ID NO 114
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 114
gccatcctgg agttc                                                          15

<210> SEQ ID NO 115
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)

<400> SEQUENCE: 115
gccatcctgg agttc                                                          15

<210> SEQ ID NO 116
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 116
ccgctgccca atgcc                                                          15

<210> SEQ ID NO 117
<211> LENGTH: 15
<212> TYPE: DNA
<213> ORGANISM: Artificial Sequence
<220> FEATURE:
```

```
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 117
tgccgctgcc caatg                                                          15

<210> SEQ ID NO 118
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 118
ctggagttcc tgtaa                                                          15

<210> SEQ ID NO 119
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: tricyclic DNA nucleoside (tc-DNA)
<220> FEATURE:
<221> NAME/KEY: misc_feature
<222> LOCATION: (4)..(4)
<223> OTHER INFORMATION: 2'-O-methyl-RNA nucleoside (2'-O-Me-RNA)
<220> FEATURE:
<221> NAME/KEY: misc_feature
<222> LOCATION: (5)..(15)
<223> OTHER INFORMATION: tricyclic DNA nucleoside (tc-DNA)

<400> SEQUENCE: 119
ctggagttcc tgtaa                                                          15

<210> SEQ ID NO 120
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 120
tcctggagtt cctgt                                                          15

<210> SEQ ID NO 121
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: tricyclic DNA nucleoside (tc-DNA)
<220> FEATURE:
<221> NAME/KEY: misc_feature
```

```
<222> LOCATION: (6)..(6)
<223> OTHER INFORMATION: 2'-O-methyl-RNA nucleoside (2'-O-Me-RNA)
<220> FEATURE:
<221> NAME/KEY: misc_feature
<222> LOCATION: (7)..(15)
<223> OTHER INFORMATION: tricyclic DNA nucleoside (tc-DNA)

<400> SEQUENCE: 121
tcctggagtt cctgt                                                15

<210> SEQ ID NO 122
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 122
acttcatccc actga                                                15

<210> SEQ ID NO 123
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: tricyclic DNA nucleoside (tc-DNA)
<220> FEATURE:
<221> NAME/KEY: misc_feature
<222> LOCATION: (5)..(5)
<223> OTHER INFORMATION: 2'-O-methyl-RNA nucleoside (2'-O-Me-RNA)
<220> FEATURE:
<221> NAME/KEY: misc_feature
<222> LOCATION: (6)..(15)
<223> OTHER INFORMATION: tricyclic DNA nucleoside (tc-DNA)

<400> SEQUENCE: 123
acttcatccc actga                                                15

<210> SEQ ID NO 124
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 124
atttcattca actgt                                                15

<210> SEQ ID NO 125
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)
```

<400> SEQUENCE: 125
gtgttcttgt acttc                                                    15

<210> SEQ ID NO 126
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: tricyclic DNA nucleoside (tc-DNA)
<220> FEATURE:
<221> NAME/KEY: misc_feature
<222> LOCATION: (11)..(11)
<223> OTHER INFORMATION: 2'-O-methyl-RNA nucleoside (2'-O-Me-RNA)
<220> FEATURE:
<221> NAME/KEY: misc_feature
<222> LOCATION: (12)..(15)
<223> OTHER INFORMATION: tricyclic DNA nucleoside (tc-DNA)

<400> SEQUENCE: 126
gtgttcttgt acttc                                                    15

<210> SEQ ID NO 127
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 127
ctgaaggtgt tcttg                                                    15

<210> SEQ ID NO 128
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: tricyclic DNA nucleoside (tc-DNA)
<220> FEATURE:
<221> NAME/KEY: misc_feature
<222> LOCATION: (5)..(5)
<223> OTHER INFORMATION: 2'-O-methyl-RNA nucleoside (2'-O-Me-RNA)
<220> FEATURE:
<221> NAME/KEY: misc_feature
<222> LOCATION: (6)..(15)
<223> OTHER INFORMATION: tricyclic DNA nucleoside (tc-DNA)

<400> SEQUENCE: 128
ctgaaggtgt tcttg                                                    15

<210> SEQ ID NO 129
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 129
ctccggttct gaagg                                                    15

<210> SEQ ID NO 130
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: tricyclic DNA nucleoside (tc-DNA)
<220> FEATURE:
<221> NAME/KEY: misc_feature
<222> LOCATION: (9)..(9)
<223> OTHER INFORMATION: 2'-O-methyl-RNA nucleoside (2'-O-Me-RNA)
<220> FEATURE:
<221> NAME/KEY: misc_feature
<222> LOCATION: (10)..(15)
<223> OTHER INFORMATION: tricyclic DNA nucleoside (tc-DNA)

<400> SEQUENCE: 130
ctccggttct gaagg                                                    15

<210> SEQ ID NO 131
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: tricyclic DNA nucleoside (tc-DNA)

<400> SEQUENCE: 131
ttgaatcctt taaca                                                    15

<210> SEQ ID NO 132
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)

<400> SEQUENCE: 132
ttgaatcctu taaca                                                    15

<210> SEQ ID NO 133
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)

```
<223> OTHER INFORMATION: tricyclic DNA nucleoside (tc-DNA)

<400> SEQUENCE: 133
ctttcataat gctgg                                                    15

<210> SEQ ID NO 134
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: tricyclic DNA nucleoside (tc-DNA)
<220> FEATURE:
<221> NAME/KEY: misc_feature
<222> LOCATION: (6)..(6)
<223> OTHER INFORMATION: 2'-O-methyl-RNA nucleoside (2'-O-Me-RNA)
<220> FEATURE:
<221> NAME/KEY: misc_feature
<222> LOCATION: (7)..(15)
<223> OTHER INFORMATION: tricyclic DNA nucleoside (tc-DNA)

<400> SEQUENCE: 134
ctttcataat gctgg                                                    15

<210> SEQ ID NO 135
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: tricyclic DNA nucleoside (tc-DNA)
<220> FEATURE:
<221> NAME/KEY: misc_feature
<222> LOCATION: (10)..(10)
<223> OTHER INFORMATION: 2'-O-methyl-RNA nucleoside (2'-O-Me-RNA)
<220> FEATURE:
<221> NAME/KEY: misc_feature
<222> LOCATION: (11)..(15)
<223> OTHER INFORMATION: tricyclic DNA nucleoside (tc-DNA)

<400> SEQUENCE: 135
ctttcataau gctgg                                                    15
```

MIXED TRICYCLO-DNA, 2'-MODIFIED RNA OLIGONUCLEOTIDE COMPOSITIONS AND USES THEREOF

CROSS-REFERENCE TO RELATED APPLICATIONS

This application is a 371 U.S. National Stage application of International Patent Application No. PCT/IB2017/055782, filed Sep. 22, 2017, which claims the benefit of U.S. Provisional Application No. 62/399,328, filed Sep. 23, 2016 and European Patent Application No. 17167426.0, filed Apr. 20, 2017, each of which is herein incorporated by reference in its entirety.

FIELD OF THE INVENTION

Therapeutic compositions and uses of mixed tricyclo-DNA, 2'-modified RNA oligonucleotides are disclosed.

BACKGROUND OF THE INVENTION

Exons of primary deoxyribonucleic acid (DNA) transcripts can be spliced in alternative arrangements that can result in structurally and functionally different messenger deoxyribonucleic acid (mRNA). Mutations in splice sites, where introns are enzymatically removed from mRNA, can lead to failed splicing wherein exons are incorrectly removed or introns incorrectly remain. For example, particular mutations in exon regions can disrupt the open reading frame and result in certain diseases. Siva, et al., *Nucleic Acid Therapeutics* 2014, 24, 69-86.

Antisense oligonucleotides, which hybridize to a target nucleic acid, represent a general strategy towards modulation of such disease-causing genes. Antisense oligonucleotides include single-stranded RNA (ssRNA), including chemical modifications to naturally-occurring sugars and bases, which is complementary to an mRNA strand transcribed in a cell. When inserted into a cell, antisense ssRNA binds to complementary mRNA and inhibits its translation, or promotes its degradation, allowing for therapeutic applications. Bennett and Swayze, *Annu. Rev. Pharmacol. Toxicol.* 2010, 50, 259-293. The FDA-approved antiviral fomivirsen (for cytomegalovirus retinitis) and cholesterol-reducing mipomersen (for familial hypercholesterolemia) are examples of antisense ssRNA approaches. Modulation of gene expression can be also achieved by a eukaryotic method of RNA-mediated gene silencing known as RNA interference. Fire, et al., *Nature* 1998, 391, 806-11. RNA interference generally involves small interfering RNA (siRNA) sequences that are double-stranded (dsRNA). Many siRNAs are 21-mer dsRNA molecules with a 2-nucleotide overhang at the 3' end of each single strand. Inside the cell, the strand with the lower hybridization energy is identified by the RNA-induced silencing complex (RISC) as the antisense strand, while the second (sense) strand is removed by an endonuclease. The antisense strand can then interfere with and silence its target in a sequence-specific manner, allowing for therapeutic applications. Kurreck, *Angew. Chem., Int. Ed.* 2009, 48, 1378-1398. Finally, the anti-microRNA approach involves targeting micro-RNA, which regulates mRNA, potentially controlling the latter and providing alternative therapeutic approaches. Ha, *Immune Netw.* 2011, 11, 227-44.

While promising, oligonucleotide therapies for diseases based on the antisense ssRNA, siRNA (dsRNA), or anti-micro-RNA approaches have encountered hurdles to development because of poor delivery to cells, insufficient cellular half-life, lack of resistance to nuclease degradation, undesired immunostimulation, lack of affinity for target RNA sequences, and off-target effects. Watts, et al., *Drug. Disc. Today,* 2008, 13, 842-55. Various chemical modification approaches have been developed in order to overcome these challenges. These include 2'O-methyl-RNA (2'O-Me-RNA), 2'-O-MOE-RNA, 2'-deoxy-2'fluoro-RNA, 2'-deoxy-2'-fluoro-β-D-arabino-NA, 4'-thio-RNA, locked nucleic acids, and tricyclo-DNA (tc-DNA). Ittig, et al., *Artificial DNA: PNA & XNA,* 2010, 1, 9-16. In particular, tc-DNA, which resembles RNA, binds selectively and with high affinity to target complementary RNA in antisense and RNA interference roles (to redirecting splicing and to block transcription), is highly stable in human serum, and does not elicit ribonuclease H activity. Another chemical modification strategy involves phosphorothioate substitution of the phosphodiester backbone linkages, which produces highly water soluble oligonucleotides that are resistant to nucleolytic degradation. Eckstein, Antisense *Nucleic Acid Drug Dev.* 2000, 10, 117. Phosphorothioate substitution is thought to be necessary for enhanced biodistribution of tc-DNA-based oligonucleotides as well as other modified oligonucleotides. To this end, phosphorothioate linkages have been introduced into tc-DNA oligonucleotides, as described in European Patent EP 2581448 B1. However, acute toxicity may be triggered upon bolus administration of some phosphorothioate tc-DNA oligonucleotides through activation of the complement cascade, possibly as the result of multimer formation. Iannitti, et al., *Curr. Drug Targets* 2014, 15, 663-73. When incorporated into an oligonucleotide, 2'-modified RNA nucleosides also generally increase stability and ribonuclease resistance of the oligonucleotide molecule, but are not associated with reduced toxicity.

Duchenne muscular dystrophy (DMD) is an X-linked, recessive disease and is the most common hereditary myopathy, afflicting about one in 3,000 males. DMD results from a mutation that affects cellular production of dystrophin, which is necessary for structural stability in muscle cell membranes. Progressive DMD causes fragility of muscle fibers, and activity results in muscle damage and recurrent necrosis. As the disease advances, skeletal muscles progressively weaken, and muscle is replaced by adipofibrotic tissue. Clinical symptoms first appear at 3 years of age, and loss of ambulation and wheelchair dependence normally occurs at 10-12 years of age. Premature death is often caused by respiratory failure or cardiac abnormalities (e.g., cardiomyopathy). Cognitive difficulties also frequently occur, possibly because of the lack of dystrophin in neuronal cells.

At a genetic level, human DMD is caused by a heterogeneous group of mutations that occur across 79 exons, although two regions of highest incidence are observed in the exon 3-7 and exon 45-55 regions. Muntoni, *Neuromuscul. Disord.* 2009, 20, 355-362. DMD results from out-of-frame deletions in the dystrophin mRNA reading frame caused by an improper stop codon. This results in an out-of-frame truncated mRNA, unstable and incomplete dystrophin, and ultimately the clinical appearance of DMD. In-frame truncated mRNA is known to result from a different mutation that leads to semifunctional dystrophin and a much milder form myopathy known as Becker muscular dystrophy (BMD). The goal of oligonucleotide therapies against DMD is generally to cause exon skipping (e.g., of exon 23, exon 51, or other any other exon), restore dystrophin production, and transform DMD into BMD, resulting in reduced mortality and potentially cognitive improvement. Besides DMD, numerous other diseases can also be potentially treated by oligonucleotide-mediated exon skipping approaches, including those diseases described hereinafter.

Spinal muscular atrophy (SMA) is a class of inherited diseases that arise from a defect in a survival motor neuron gene (SMN1) mapped to chromosome 5q11.2-13.3. Overall, SMA is characterized by a loss of spinal cord and brainstem motor neurons, resulting in muscular atrophy from the loss of neural contact. The various SMAs have an incidence of about 1 in 6,000. Type I SMA, which is also known as Werdnig-Hoffman disease or severe infantile SMA, affects babies in their first year of life, and is generally fatal. Type II SMA, also known as intermediate SMA, affects children and causes muscle weakness such that the patients are never able to stand and walk, but may be able to sit, although weakness increases with age. Type III SMA patients are able to walk at some point in their development.

SMA is caused by the loss of a functional SMN1 gene, and a mutation in exon 7 of the SMN2 paralog that causes substantial skipping of this exon and production of only low levels of functional protein, such that SMN2 protein cannot compensate for the loss of SMN1. Cartegni, et al., *Am. J. Hum. Genet.* 2006, 78, 63-77. Oligonucleotide-mediated exon-inclusion methods for the treatment of SMA are being explored, including methods of compensating for the deleterious mutation in SMN2 by masking an intronic silencing sequence and/or a terminal stem-loop sequence within an SMN2 gene to yield a modified functional SMN2 protein, including an amino acid sequence encoded by exon 7, which is capable of at least partially complementing a non-functional SMN1 protein. See, e.g., International Patent Application Publication No. WO 2010/115993 A1, the disclosure of which is incorporated herein by reference. Besides SMA, numerous other diseases can also be potentially treated by the exon inclusion approach, including those diseases described hereinafter.

The present invention provides the unexpected finding that particular mixtures of tc-DNA and 2'-modified RNA nucleosides with combinations of phosphorothioate and phosphorodiester linkages within an oligomeric molecule result in suprisingly reduced toxicity, while also retaining the increased stability and other characteristics of tc-DNA and 2'-modified RNA nucleosides and the enhanced biodistribution and other improvements associated with phosphorothioate substitution.

SUMMARY OF THE INVENTION

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound comprises from about 10 to about 20 nucleotides.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the melting temperature ($T_m$) of the oligomeric compound is at least about 50° C.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the melting temperature ($T_m$) of the oligomeric compound is at least 50° C.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein 2'-modified-RNA nucleosides are incorporated in positions such that self-complementary binding under physiological conditions is prevented.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound is a monomer as determined by non-denaturing gel electrophoresis.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound exhibits a monomer to multimer ratio of at least about 100 to 1 as determined by size-exclusion chromatography.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the C3 percentage determined in a complement assay in an in vitro serum is at least about 55% (relative to non-activated complement at 100%), wherein the in vitro serum is selected from the group consisting of human, monkey, dog, mouse, and rat serum.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the C3 percentage determined in a complement assay in an in vitro serum is at least 55% (relative to non-activated complement at 100%), wherein the in vitro serum is selected from the group consisting of human, monkey, dog, mouse, and rat serum.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound is not toxic in an animal model at a dose that would be equivalent to a therapeutically effective dose in a human, wherein the animal model is a mouse model or a primate model.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein 2'-modified-RNA nucleosides are incorporated in at least one position that forms self-complementary Watson-Crick base pairs.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein 2'-modified-RNA nucleosides are incorporated in at least two adjacent positions that form self-complementary Watson-Crick base pairs.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein 2'-modified-RNA nucleosides are incorporated at three or more adjacent positions that form self-complementary Watson-Crick base pairs.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound does not contain a direct tc-DNA to tc-DNA phosphorothioate internucleoside linkage.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, which is complementary to a target sequence.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the 2'-modified-RNA nucleosides are 2'-O-methyl-RNA nucleosides.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the 2'-modified-RNA nucleosides are 2'-fluoro-RNA nucleosides.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein each of the plurality of internucleoside linkages is independently selected from a phosphorothioate linkage, a phosphorodithioate linkage, and a phosphorodiester linkage, a phosphotriester linkage, an aminoalkylphosphotriester linkage, a methyl phosphonate linkage, an alkyl phosphonate linkage, a 5'-alkylene phosphonate linkage, a phosphonate linkage, a phosphinate linkage, a phosphoramidate linkage, an 3'-aminophosphoramidate linkage, an aminoalkyl phosphoramidate linkage, a thionophosphoramidate linkage, a thionoalkylphosphonate linkage, a thionoalkylphosphotriester linkage, a selenophosphate linkage, or a boranophosphate linkage.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the internucleoside linkages comprise a plurality of phosphorothioate linkages and a plurality of phosphorodiester linkages.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein no more than about 90% of the plurality of internucleoside linkages are phosphorothioate linkages. In an embodiment, the invention provides the foregoing oligomeric compound, wherein no more than about 75% of the plurality of internucleoside linkages are phosphorothioate linkages. In an embodiment, the invention provides the foregoing oligomeric compound, wherein no more than about 50% of the plurality of internucleoside linkages are phosphorothioate linkages. In an embodiment, the invention provides the foregoing oligomeric compound, wherein no more than about 33% of the plurality of internucleoside linkages are phosphorothioate linkages. In an embodiment, the invention provides the foregoing oligomeric compound, wherein no more than about 25% of the plurality of internucleoside linkages are phosphorothioate linkages. In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein all of the plurality of internucleoside linkages are phosphorothioate linkages.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein at least about 50% of the plurality of internucleoside linkages are phosphorodiester linkages. In an embodiment, the invention provides the foregoing oligomeric compound, wherein at least about 66% of the plurality of internucleoside linkages are phosphorodiester linkages. In an embodiment, the invention provides the foregoing oligomeric compound, wherein at least about 75% of the plurality of internucleoside linkages are phosphorodiester linkages.

In an embodiment, the invention provides an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, wherein the oligomeric compound comprises a sequence selected from the group consisting of:

```
                                            (SEQ ID NO: 43)
    5'-A*a*G*a*u*g*GCATTTCTA-3', (SEQ ID NO: 44)
    5'-AAGATGGCA*u*T*u*C*u*A-3', (SEQ ID NO: 45)
    5'-GAAGATGGCA*u*u*u*c*T-3', (SEQ ID NO: 46)
    5'-AGGAAGATGGCA*u*u*u*c*u*A-3', (SEQ ID NO: 47)
    5'-AGGAAGATGG*c*a*u*u*u*CTA-3', (SEQ ID NO: 48)
    5'-AGGAAGATGG*c*a*u*u*u*c*u*A-3',
```

-continued

```
                                                (SEQ ID NO: 49)
5'-A*a*G*a*u*g*GCATTTCTAGTT-3', (SEQ ID NO: 50)
5'-A*a*g*a*u*g*GCATTTCTAGTT-3', (SEQ ID NO: 51)
5'-AA*g*a*u*g*GCATTTCTAGTT-3', (SEQ ID NO: 52)
5'-AGGAAG*a*u*g*GCATTTCTA-3', (SEQ ID NO: 53)
5'-AGGA*a*g*a*u*g*GCATTTCTA-3', (SEQ ID NO: 54)
5'-GGA*a*g*a*u*g*GCATTTCTA-3', (SEQ ID NO: 55)
5'-GGA*a*g*a*u*g*GCATTTCT-3', (SEQ ID NO: 56)
5'-AGGAA*g*a*u*g*g*CATTTCTA-3', (SEQ ID NO: 57)
5'-AGGA*a*g*a*u*g*g*CATTTCTA-3', (SEQ ID NO: 58)
5'-AGGAAGATGG*c*a*u*u*c*u-3', (SEQ ID NO: 59)
5'-a*g*a*u*g*GCATTTCTAGTT-3', (SEQ ID NO: 60)
5'-AGGAAGATGG*c*a* u*u*u*c*u-3', (SEQ ID NO: 61)
5'-s*s*AAGAuGGCATTTCTA-3', (SEQ ID NO: 62)
5'-s*s*s*s*AAGAuGGCATTTCTA-3', (SEQ ID NO: 63)
5'-s*s*s*s*s*s*AAGAuGGCATTTCTA-3', (SEQ ID NO: 64)
5'-s*s*s*s*s*s*s*s*AAGAuGGCATTTCTA-3', (SEQ ID NO: 65)
5'-s*s*s*s*s*s*s*s*s*AAGAuGGCATTTCTA-3', (SEQ ID NO: 66)
5'-A*A*G*A*T*G*G*C*A*u*T*T*C*T*A-3',
and (SEQ ID NO: 67)
5'-A*A*G*A*T*G*G*C*a*T*T*T*C*T*A-3',
``` wherein an * between two nucleosides indicates a phosphorothioate, the absence of an * between two nucleosides indicates a phosphorodiester, the capitalized letters A, C, G, and T indicate tc-DNA nucleosides; the lowercase letters a, u, g, and t indicate 2'-O-methyl-RNA nucleosides, the nucleobase at all C positions is 5-methylcytosine, the nucleobase at all c positions is cytosine, and s represents a —O—CH$_2$—CH$_2$—CH$_2$—O— (1,3-propanediol) non-nucleoside.

In an embodiment, the invention provides a pharmaceutical composition that includes an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, according to any one of the foregoing embodiments.

In an embodiment, the invention provides a pharmaceutical composition that includes an oligomeric compound comprising a plurality of tricyclo-deoxyribonucleic acid (tc-DNA) nucleosides and a plurality of 2'-modified ribonucleic acid (2'-modified-RNA) nucleosides joined by a plurality of internucleoside linkages, according to any one of the foregoing embodiments, for use in the treatment of a neuromuscular or musculoskeletal disease. In an embodiment, the neuromuscular or musculoskeletal disease is selected from the group consisting of Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease).

In an embodiment, the invention provides a method for treating a neuromuscular or musculoskeletal disease comprising the step of administering to a patient a therapeutically effective dose of the pharmaceutical composition of any of the foregoing embodiments of oligomeric compounds. In an embodiment, the neuromuscular or musculoskeletal disease is selected from the group consisting of Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease).

In an embodiment, the invention provides a method of treating a disease of the central nervous system (CNS) comprising the step of administering to a patient a therapeutically effective dose of a pharmaceutical composition of any of the foregoing embodiments of oligomeric compounds.

In an embodiment, the invention provides a method of treating a neurodegenerative disease comprising the step of administering to a patient a therapeutically effective dose of a pharmaceutical composition of any of the foregoing embodiments of oligomeric compounds. In an embodiment, the neurodegenerative disease selected from the group consisting of amyotrophic lateral sclerosis (ALS), Alzheimer's Disease (AD), Parkinson's Disease (PD); Multiple Sclerosis (MS), epilepsy, Creutzfeldt-Jakob disease (CJ), Menkes Disease, and Huntington's Disease (HD).

In an embodiment, the invention provides a method of treating a psychiatric disorder comprising the step of administering to a patient a therapeutically effective dose of a pharmaceutical composition of any of the foregoing embodiments of oligomeric compounds. In an embodiment, the psychiatric disorder is selected from the group consisting of mood disorders, dementia, anxiety, bipolar disorder, schizophrenia, post-traumatic stress disorder (PTSD), attention deficit hyperactivity disorder (ADHD), and depression.

In an embodiment, the invention provides for a method of treating a disease or disorder that affects cerebellar function comprising the step of administering to a patient a therapeutically effective dose of a pharmaceutical composition of any of the foregoing embodiments of oligomeric compounds.

In an embodiment, the invention provides for a method of treating a disease or disorder that affects amygdala function comprising the step of administering to a patient a therapeutically effective dose of a pharmaceutical composition of any of the foregoing embodiments of oligomeric compounds.

In an embodiment, the invention provides for a method of treating a disease or disorder that affects hippocampal function comprising the step of administering to a patient a therapeutically effective dose of a pharmaceutical composition of any of the foregoing embodiments of oligomeric compounds.

In an embodiment, the invention provides for a method of treating a sleep disorder comprising the step of administering to a patient a therapeutically effective dose of a pharmaceutical composition of any of the foregoing embodiments of oligomeric compounds. In an embodiment of the invention, the sleep disorder is selected from the group consisting of slow wave sleep disturbance and insomnia.

In an embodiment, the invention provides a method of treating a cognitive disorder comprising the step of administering to a patient a therapeutically effective dose of a pharmaceutical composition of any of the foregoing embodiments of oligomeric compounds.

In an embodiment, the invention provides for a method of treating a symptom of schizophrenia comprising the step of administering to a patient a therapeutically effective dose of a pharmaceutical composition of any of the foregoing embodiments of oligomeric compounds. In an embodiment, the symptom is a positive or a negative symptom of schizophrenia. In an embodiment, the positive symptom is selected from the group consisting of hallucinations, delusions, and disturbances in logical thought process. In an embodiment, the symptom is a negative symptom selected from the group consisting of alogia, avolition, dysphoric mood, poor impulse control, abnormal psychomotor activity, lack of judgment, disturbances in sleep pattern, affective flattening, lack of motivation, lack of spontaneity, reduced ability to think abstractly, and reduced ability to experience pleasure.

BRIEF DESCRIPTION OF THE DRAWINGS

The foregoing summary, as well as the following detailed description of the invention, will be better understood when read in conjunction with the appended drawings.

FIG. 1 illustrates a sequence (SYN51, SEQ ID NO:68) used to illustrate acute toxicity of phosphorothioate tc-DNA oligonucleotides. The symbol "I" refers to Watson-Crick pairing, and the symbol ":" refers to G-T wobble base pairs.

FIG. 21 illustrates the detailed results of melting temperature measurements.

FIG. 22 illustrates the detailed results of melting temperature measurements.

FIG. 23 illustrates the detailed results of melting temperature measurements.

BRIEF DESCRIPTION OF THE SEQUENCE LISTING

Figure 2:
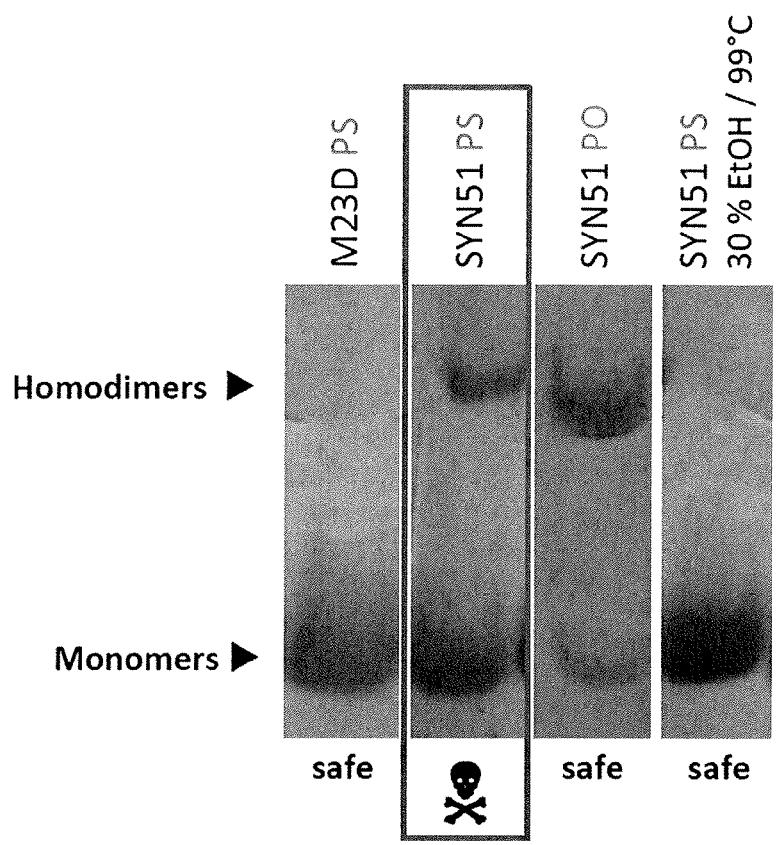
FIG. 2 illustrates the results of gel electrophoresis experiments. The SYN51 lanes shows the results of the oligonucleotide of FIG. 1 synthesized with all phosphorothioate linkages ("PS") and all phosphorodiester linkages ("PO"). The other lanes illustrate a control oligonucleotide ("M23D") and the SYN51 PS oligonucleotide after storage in 30% ethanol at high temperature to break multimers. The notation "safe" indicates oligonucleotides that were safe in animal testing.

SEQ ID NO: 1 is a nucleotide sequence for an oligonucleotide of the present invention.

SEQ ID NO:2 is a nucleotide sequence for an oligonucleotide of the present invention.

SEQ ID NO:3 is a nucleotide sequence for an oligonucleotide of the present invention.

SEQ ID NO:4 is a nucleotide sequence for an oligonucleotide of the present invention.

SEQ ID NO:5 is a nucleotide sequence for an oligonucleotide of the present invention.

SEQ ID NO:6 is a nucleotide sequence for an oligonucleotide of the present invention.

SEQ ID NO:7 is a nucleotide sequence for an oligonucleotide of the present invention.

SEQ ID NO:8 is a nucleotide sequence for an oligonucleotide of the present invention.

SEQ ID NO:9 is a nucleotide sequence for an oligonucleotide of the present invention.

SEQ ID NO: 10 is a nucleotide sequence for an oligonucleotide of the present invention.

SEQ ID NO: 11 is a nucleotide sequence for an oligonucleotide of the present invention.

SEQ ID NO: 12 is a nucleotide sequence for an oligonucleotide of the present invention.

SEQ ID NO: 13 is a nucleotide sequence for an oligonucleotide of the present invention.

SEQ ID NO: 14 is a nucleotide sequence for an oligonucleotide of the present invention.

SEQ ID NO: 15 is a nucleotide sequence for an oligonucleotide of the present invention.

SEQ ID NO: 16 is a nucleotide sequence for an oligonucleotide of the present invention.

SEQ ID NO: 17 is a nucleotide sequence for an oligonucleotide of the present invention.

SEQ ID NO: 18 is a nucleotide sequence for an oligonucleotide of the present invention.

SEQ ID NO: 19 is a nucleotide sequence for an oligonucleotide of the present invention.

SEQ ID NO:20 is a nucleotide sequence for an oligonucleotide of the present invention.

SEQ ID NO:21 is a nucleotide sequence for an oligonucleotide of the present invention.

SEQ ID NO:22 is a nucleotide sequence for an oligonucleotide of the present invention.

SEQ ID NO:23 is a nucleotide sequence for an oligonucleotide of the present invention.

SEQ ID NO:24 is a nucleotide sequence for an oligonucleotide of the present invention.

SEQ ID NO:25 is a nucleotide sequence for an oligonucleotide of the present invention.

SEQ ID NO:26 is a nucleotide sequence for an oligonucleotide of the present invention.

SEQ ID NO:27 is a nucleotide sequence for an oligonucleotide of the present invention.

SEQ ID NO:28 is a nucleotide sequence for an oligonucleotide of the present invention.

SEQ ID NO:29 is a nucleotide sequence for an oligonucleotide of the present invention.

SEQ ID NO:30 is a nucleotide sequence for an oligonucleotide of the present invention.

SEQ ID NO:31 is a nucleotide sequence for an oligonucleotide of the present invention (SY-0329).

SEQ ID NO:32 is a nucleotide sequence for an oligonucleotide of the present invention (SY-0330).

SEQ ID NO:33 is a nucleotide sequence for an oligonucleotide of the present invention (SY-0331).

SEQ ID NO:34 is a nucleotide sequence for an oligonucleotide of the present invention (SY-0332).

SEQ ID NO:35 is a nucleotide sequence for an oligonucleotide of the present invention (SY-0333).

SEQ ID NO:36 is a nucleotide sequence for an oligonucleotide of the present invention (SY-0334).

SEQ ID NO:37 is a nucleotide sequence for an oligonucleotide of the present invention (SY-0335).

SEQ ID NO:38 is a nucleotide sequence for an oligonucleotide of the present invention (SY-0337).

SEQ ID NO:39 is a nucleotide sequence for an oligonucleotide of the present invention (SY-0338).

SEQ ID NO:40 is a nucleotide sequence for an oligonucleotide of the present invention (SY-0339).

SEQ ID NO:41 is a nucleotide sequence for an oligonucleotide of the present invention (SY-0340).

SEQ ID NO:42 is a nucleotide sequence for an oligonucleotide of the present invention (SY-0341).

SEQ ID NO:43 is a nucleotide sequence for an oligonucleotide of the present invention (SY-0371).

SEQ ID NO:44 is a nucleotide sequence for an oligonucleotide of the present invention (SY-0372).

SEQ ID NO:45 is a nucleotide sequence for an oligonucleotide of the present invention (SY-0373).

SEQ ID NO:46 is a nucleotide sequence for an oligonucleotide of the present invention (SY-0374).

SEQ ID NO:47 is a nucleotide sequence for an oligonucleotide of the present invention (SY-0388).

SEQ ID NO:48 is a nucleotide sequence for an oligonucleotide of the present invention (SY-0389).

SEQ ID NO:49 is a nucleotide sequence for an oligonucleotide of the present invention (SY-0390).

SEQ ID NO:50 is a nucleotide sequence for an oligonucleotide of the present invention (SY-0391).

SEQ ID NO:51 is a nucleotide sequence for an oligonucleotide of the present invention (SY-0392).

SEQ ID NO:52 is a nucleotide sequence for an oligonucleotide of the present invention (SY-0393).

SEQ ID NO:53 is a nucleotide sequence for an oligonucleotide of the present invention (SY-0394).

SEQ ID NO:54 is a nucleotide sequence for an oligonucleotide of the present invention (SY-0395).

SEQ ID NO:55 is a nucleotide sequence for an oligonucleotide of the present invention (SY-0396).

SEQ ID NO:56 is a nucleotide sequence for an oligonucleotide of the present invention (SY-0397).

SEQ ID NO:57 is a nucleotide sequence for an oligonucleotide of the present invention (SY-0398).

SEQ ID NO:58 is a nucleotide sequence for an oligonucleotide of the present invention (SY-0406).

SEQ ID NO:59 is a nucleotide sequence for an oligonucleotide of the present invention (SY-0405).

SEQ ID NO:60 is a nucleotide sequence for an oligonucleotide of the present invention (SY-0407).

SEQ ID NO:61 is a nucleotide sequence for an oligonucleotide of the present invention (SY-0408).

SEQ ID NO:62 is a nucleotide sequence for an oligonucleotide of the present invention (SY-0410).

SEQ ID NO:63 is a nucleotide sequence for an oligonucleotide of the present invention (SY-0412).

SEQ ID NO:64 is a nucleotide sequence for an oligonucleotide of the present invention (SY-0414).

SEQ ID NO:65 is a nucleotide sequence for an oligonucleotide of the present invention (SY-0416).

SEQ ID NO:66 is a nucleotide sequence for an oligonucleotide of the present invention (SY-0417).

SEQ ID NO:67 is a nucleotide sequence for an oligonucleotide of the present invention (SY-0418).

SEQ ID NO:68 is a nucleotide sequence for oligonucleotide SYN51 (Syn15-mer HEX51 (+67+81)).

SEQ ID NO:69 is a nucleotide sequence for oligonucleotide Syn13-mer HEX51 (+68+80).

SEQ ID NO:70 is a nucleotide sequence for oligonucleotide SY-0206.

SEQ ID NO:71 is a nucleotide sequence for oligonucleotide SY-0210.

SEQ ID NO:72 is a nucleotide sequence for oligonucleotide SY-0208.

SEQ ID NO:73 is a nucleotide sequence for oligonucleotide SY-0336.

SEQ ID NO:74 is a nucleotide sequence for oligonucleotide SY-0219.

SEQ ID NO:75 is a nucleotide sequence for oligonucleotide Hex51 (+66;+83) 2-OMe 17 (SY-0375).

SEQ ID NO:76 is a nucleotide sequence for oligonucleotide Biot-Hex51 (+67;+81) 2-OMe 11 (SY-0376).

SEQ ID NO:77 is a nucleotide sequence for oligonucleotide Biot-Hex51 (+67;+81) 2-OMe 13 (6Sb5) (SY-0377).

SEQ ID NO:78 is a nucleotide sequence for oligonucleotide Biot-Hex51 (+67;+81) 2-OMe 14 (6Sb3) (SY-0378).

SEQ ID NO:79 is a nucleotide sequence for oligonucleotide Biot-Hex51 (+67;+81) 2-OMe 15 (5Sb3) (SY-0379).

SEQ ID NO:80 is a nucleotide sequence for oligonucleotide Biot-Hex51 (+66;+83) 2-OMe 16 (6Sb3) (SY-0380).

SEQ ID NO:81 is a nucleotide sequence for oligonucleotide Biot-Hex51 (+66;+83) 2-OMe 17 (SY-0381).

SEQ ID NO:82 is a nucleotide sequence for oligonucleotide M23D-15m (2OMe 5Sb3) (SY-0382).

SEQ ID NO:83 is a nucleotide sequence for oligonucleotide M23D-15m (2OMe 4Sb3) (SY-0383).

SEQ ID NO:84 is a nucleotide sequence for oligonucleotide M23D-15m (2OMe 3Sb3) (SY-0384).

SEQ ID NO:85 is a nucleotide sequence for oligonucleotide Biot-M23D-15m (2OMe 5Sb3) (SY-0385).

SEQ ID NO:86 is a nucleotide sequence for oligonucleotide Biot-M23D-15m (2OMe 4Sb3) (SY-0386).

SEQ ID NO:87 is a nucleotide sequence for oligonucleotide Biot-M23D-15m (2OMe 3Sb3) (SY-0387).

SEQ ID NO:88 is a nucleotide sequence for oligonucleotide Hex45 (−2;+13) (SY-0462).

SEQ ID NO:89 is a nucleotide sequence for oligonucleotide Hex45 (−2;+13) 2-OMe 01 (SY-0463).

SEQ ID NO:90 is a nucleotide sequence for oligonucleotide Hex45 (+1;+15) (SY-0464).

SEQ ID NO:91 is a nucleotide sequence for oligonucleotide Hex45 (+1;+15) 2-OMe 01 (SY-0465).

SEQ ID NO:92 is a nucleotide sequence for oligonucleotide Hex45 (+13;+27) (SY-0466).

SEQ ID NO:93 is a nucleotide sequence for oligonucleotide Hex45 (+15;+29) (SY-0467).

SEQ ID NO:94 is a nucleotide sequence for oligonucleotide Hex45 (−6;+9) (SY-0471).

SEQ ID NO:95 is a nucleotide sequence for oligonucleotide Hex45 (−6;+9) 2-OMe 01 (SY-0472).

SEQ ID NO:96 is a nucleotide sequence for oligonucleotide Hex45 (−4;+11) (SY-0473).

SEQ ID NO:97 is a nucleotide sequence for oligonucleotide Hex45 (−4;+11) 2-OMe 01 (SY-0474).

SEQ ID NO:98 is a nucleotide sequence for oligonucleotide Hex53 (+17;+31) (SY-0468).

SEQ ID NO:99 is a nucleotide sequence for oligonucleotide Hex53 (+17;+31) 2-OMe 01 (SY-0469).

SEQ ID NO: 100 is a nucleotide sequence for oligonucleotide Hex53 (+59;+73) (SY-0470).

SEQ ID NO: 101 is a nucleotide sequence for oligonucleotide Hex53 (+27;+41) (SY-0475).

SEQ ID NO: 102 is a nucleotide sequence for oligonucleotide Hex53 (+27;+41) 2-OMe 01 (SY-0476).

SEQ ID NO: 103 is a nucleotide sequence for oligonucleotide Hex53 (+33;+47) (SY-0477).

SEQ ID NO: 104 is a nucleotide sequence for oligonucleotide Hex53 (+33;+47) 2-OMe 01 (SY-0478).

SEQ ID NO: 105 is a nucleotide sequence for oligonucleotide Hex53 (+41;+55) (SY-0479).

SEQ ID NO: 106 is a nucleotide sequence for oligonucleotide Hex53 (+41;+55) 2-OMe 01 (SY-0480).

SEQ ID NO: 107 is a nucleotide sequence for oligonucleotide Hex53 (+73;+87) (SY-0481).

SEQ ID NO: 108 is a nucleotide sequence for oligonucleotide Hex53 (+73;+87) 2-OMe 01 (SY-0482).

SEQ ID NO: 109 is a nucleotide sequence for oligonucleotide PS SMN 2i7 (SY-0221).

SEQ ID NO: 110 is a nucleotide sequence for oligonucleotide PS SMN 2i7 2-OMe 01 (SY-0483).

SEQ ID NO: 111 is a nucleotide sequence for oligonucleotide PS SMN 2i7 2-OMe 02 (SY-0484).

SEQ ID NO: 112 is a nucleotide sequence for an oligonucleotide of the present invention.

SEQ ID NO: 113 is a nucleotide sequence for an oligonucleotide of the present invention.

SEQ ID NO: 114 is a nucleotide sequence for an oligonucleotide of the present invention.

SEQ ID NO: 115 is a nucleotide sequence for an oligonucleotide of the present invention.

SEQ ID NO: 116 is a nucleotide sequence for an oligonucleotide of the present invention.

SEQ ID NO: 117 is a nucleotide sequence for an oligonucleotide of the present invention.

SEQ ID NO: 118 is a nucleotide sequence for an oligonucleotide of the present invention.

SEQ ID NO: 119 is a nucleotide sequence for an oligonucleotide of the present invention.

SEQ ID NO: 120 is a nucleotide sequence for an oligonucleotide of the present invention.

SEQ ID NO: 121 is a nucleotide sequence for an oligonucleotide of the present invention.

SEQ ID NO: 122 is a nucleotide sequence for an oligonucleotide of the present invention.

SEQ ID NO: 123 is a nucleotide sequence for an oligonucleotide of the present invention.

SEQ ID NO: 124 is a nucleotide sequence for an oligonucleotide of the present invention.

SEQ ID NO: 125 is a nucleotide sequence for an oligonucleotide of the present invention.

SEQ ID NO: 126 is a nucleotide sequence for an oligonucleotide of the present invention.

SEQ ID NO: 127 is a nucleotide sequence for an oligonucleotide of the present invention.

SEQ ID NO: 128 is a nucleotide sequence for an oligonucleotide of the present invention.

SEQ ID NO: 129 is a nucleotide sequence for an oligonucleotide of the present invention.

SEQ ID NO: 130 is a nucleotide sequence for an oligonucleotide of the present invention.

SEQ ID NO: 131 is a nucleotide sequence for an oligonucleotide of the present invention.

SEQ ID NO: 132 is a nucleotide sequence for an oligonucleotide of the present invention.

SEQ ID NO: 133 is a nucleotide sequence for an oligonucleotide of the present invention.

SEQ ID NO: 134 is a nucleotide sequence for an oligonucleotide of the present invention.

SEQ ID NO: 135 is a nucleotide sequence for an oligonucleotide of the present invention.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

Definitions

The terms "oligomeric compound" and "oligonucleotide" refer to short polynucleotides that contain nucleotide monomeric subunits. The length of an oligonucleotide may be denoted by the number of nucleotide monomeric subunits concatenated to the term "-mer." For example, an oligonucleotide containing ten nucleotide monomeric subunits is a 10-mer (or decamer), and an oligonucleotide containing 25 nucleotide monomeric subunits is a 25-mer. Oligonucleotides and oligomeric compounds of the present disclosure are listed from left to right following the order of the 5' to the 3' end, respectively.

The term "antisense oligonucleotide" refers to an oligonucleotide or oligomeric compound that is capable of interacting with and/or hybridizing to a pre-mRNA or an mRNA having a complementary nucleotide sequence thereby modifying gene expression.

The melting temperature ($T_m$) of an oligonucleotide or oligomeric compound refers to the temperature at which 50% of the oligonucleotide and its complement are in a duplex.

The terms "joined" or "joining," as used herein with reference to the connectivity of two or more nucleosides or non-nucleosides by one or more internucleoside linkages, encompass the direct joining of two nucleosides or non-nucleosides by one internucleoside linkage, and also encompass indirect joining of two or more nucleosides or non-nucleosides through one or more additional nucleosides, non-nucleosides, and internucleoside linkages.

The term "base analog" (also referred to as "modified nucleobases") refers to chemical modifications of DNA or RNA bases with a molecular structure that mimics natural DNA or RNA bases. Base analogs include, but are not limited to, 5-methylcytosine, 5-bromouracil, inosine, 5-substituted pyrimidines, 6-azapyrimidines and N-2, N-6 and O-6 substituted purines, including 2-aminopropyladenine, 5-propynyluracil and 5-propynylcytosine. Base analogs also include, but are not limited to, 5-hydroxymethylcytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine, 2-thiocytosine, 5-halouracil and cytosine, 5-propinyluracil and 5-propinylcytosine (and other alkynyl derivatives of pyrimidine bases), 6-azouracil, 6-azocytosine, 6-azothymine, 5-uracil (pseudouracil), 4-thiouracil, 8-halo, 8-amino, 8-thiol, 8-thioalkyl, 8-hydroxyl and other 8-substituted adenines and guanines, 5-halo and particularly 5-bromo, 5-trifluoromethyl and other 5-substituted uracils and cytosine's, 7-methylguanine and 7-methyladenine, 2-F-adenine, 2-amino-adenine, 8-azaguanine and 8-azaadenine, 7-deazaguanine and 7-deaza-adenine, 3-deazaguanine and 3-deaza-adenine, universal bases, tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), and pyridoindole cytidine (2H-pyrido[3',2':4,5]pyrrolo[2,3-d]pyrimidin-2-one). Base analogs may also include those in which the purine or pyrimidine base is replaced with other heterocycles, for example 7-deaza-adenine, 7-deazaguanosine, 2-aminopyridine and 2-pyridone. The preparation of modified nucleobases is known in the art and is described in U.S. Pat. Nos. 3,687,808, 4,845,205; 5,130,302; 5,134,066; 5,175,273; 5,367,066; 5,432,272; 5,457,187; 5,459,255; 5,484,908; 5,502, 177; 5,525,711; 5,552,540; 5,587,469; 5,594, 121; 5,596,091; 5,614,617; 5,645,985; 5,750,692; 5,830,653; 5,763,588; 6,005,096; and 5,681,941.

The term "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. "Complementary" (or "specifically hybridizable") are terms that indicate a sufficient degree of complementarity or precise pairing such that stable and specific binding occurs between an oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity may be indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "exon skipping" refers to the modification of pre-mRNA splicing by the targeting of splice donor and/or acceptor sites within a pre-mRNA with one or more complementary antisense oligonucleotides or oligomeric compounds. By blocking access of a spliceosome to one or more splice donor or acceptor sites, or any other site within an exon or intron involved in the definition of splicing, an oligonucleotide can prevent a splicing reaction and cause the deletion of exons from a fully-processed mRNA. Exon skipping is achieved in the nucleus during the maturation process of pre-mRNAs. Exon skipping includes the masking of key sequences involved in the splicing of targeted exons by using antisense oligonucleotides that are complementary to splice donor sequences within a pre-mRNA. For example, the oligomeric compounds provided herein may be suitably employed for exon skipping through the masking of splice sites at intron/exon junctions within a dystrophin pre-mRNA thereby facilitating the deletion of a mutant exon during the processing of the pre-mRNA to a mature mRNA.

The term "exon inclusion" refers to oligonucleotide-mediated processes such as the base-pairing of antisense oligonucleotides to a target pre-mRNA to block an exonic or intronic splicing enhancer and block the corresponding splicing repressor and/or disrupt an unfavorable secondary structure, resulting in more efficient recognition of the exon by the spliceosome and restoration of exon expression.

The terms "co-administration," "co-administering," "administered in combination with," "administering in combination with," "simultaneous," and "concurrent," as used herein, encompass administration of two or more active pharmaceutical ingredients to a human subject so that both active pharmaceutical ingredients and/or their metabolites are present in the human subject at the same time. Co-administration includes simultaneous administration in separate compositions, administration at different times in separate compositions, or administration in a composition in which two or more active pharmaceutical ingredients are present. Simultaneous administration in separate compositions and administration in a composition in which both agents are present is also encompassed in the methods of the invention.

The terms "active pharmaceutical ingredient" and "drug" include oligomeric compounds such as oligonucleotides.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

"Prodrug" is intended to describe a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers the advantages of solubility, tissue compatibility or delayed release in a mammalian organism (see, e.g., Bundgaard, *Design of Prodrugs*, Elsevier, Amsterdam, 1985). The term "prodrug" is also intended to include any covalently bonded carriers, which release the active compound in vivo when administered to a subject. Prodrugs of an active compound, as described herein, may be prepared by modifying functional groups present in the active compound in such a way that the modifications are cleaved, either in routine manipulation or in vivo, to yield the active parent compound. Prodrugs include, for example, compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetates, formates and benzoate derivatives of an alcohol, various ester derivatives of a carboxylic acid, or acetamide, formamide and benzamide derivatives of an amine functional group in the active compound.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C- or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

"Alkyl" refers to a straight or branched hydrocarbon chain radical consisting solely of carbon and hydrogen atoms, containing no unsaturation, having from one to sixteen carbon atoms (e.g., ($C_{1-16}$)alkyl or $C_{1-16}$alkyl). Whenever it appears herein, a numerical range such as "1 to 16" refers to each integer in the given range—e.g., "1 to 20 carbon atoms" means that the alkyl group may consist of 1 carbon atom, 2 carbon atoms, 3 carbon atoms, etc., up to and including 20 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., (C$_{2-10}$)alkenyl or C$_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., (C$_{2-10}$)alkynyl or C$_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e. (C$_{3-10}$)cycloalkyl or C$_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxy" refers to the group —O-alkyl, including from 1 to 16 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons, also referred to as $(C_{1-6})$alkoxy or O—$(C_{1-6})$alkyl.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R')C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R')$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C=O)— attached through the carbonyl carbon wherein the alkoxy group has the indicated number of carbon atoms. Thus a $(C_{1-20})$alkoxycarbonyl group is an alkoxy group having from 1 to 20 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C=O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R')$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$_2$ of —N(R)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, *Protective Groups in Organic Synthesis*, 5$^{th}$ Ed., John Wiley & Sons, New York, N.Y., 2014, which is incorporated herein by reference in its entirety.

"Aromatic" or "aryl" or "Ar" refers to an aromatic radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R')$_2$, N(R$^a$)C(NR$^a$)N(R)$_2$, —N(R$^a$)S(O)$_t$R$^a$ (where t is 1 or 2), —S(O)$_t$OR$^a$ (where t is 1 or 2), —S(O)N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 5$^{th}$ Ed., John Wiley & Sons, New York, N.Y., 2014, which is incorporated herein by reference in its entirety. Unless stated otherwise specifically in the specification, an ester group is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., $C_1$-$C_4$ heteroalkyl which refers to the chain length in total, which in this example is 4 atoms long. A heteroalkyl group may be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R')$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylheterocycloalkyl" refers to an -(heteroalkyl)heterocycloalkyl radical where heteroalkyl and heterocloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyrimidinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R')C(O)OR$^a$, —N(R')C(O)R$^a$, —N(R$^a$)C(O)N(R')$_2$, N(R$^a$)C(NR$^a$)N(R$^a$)$_2$, —N(R')S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. Substituted heteroaryl also includes ring systems substituted with one or more oxide (—O—) substituents, such as, for example, pyridinyl N-oxides.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R')S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Nitro" refers to the —NO$_2$ radical.

"Oxa" refers to the —O— radical.

"Oxo" refers to the =O radical.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)$_2$—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. The oligomeric compounds of the present invention can include mixtures of diastereomers, including complex mixtures comprising diastereomers formed by inversion of stereocenters from chemical reactions designed to form phosphorothioate groups. Such mixtures include mixtures comprising greater than 1%, 2%, 5%, 10%, 20%, 30%, 40%, 50%, 60%, 70%, 80%, or 90% of one or more given diastereomers. Such mixtures also include mixtures comprising less than 1%, 2%, 5%, 10%, 20%, 30%, 40%, 50%, 60%, 70%, 80%, or 90% of one or more given diastereomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or enantiomers can be prepared by asymmetric syntheses. See, for example, Jacques, et al., *Enantiomers, Racemates and Resolutions*, Wiley Interscience, New York (1981); Eliel, *Stereochemistry of Carbon Compounds*, McGraw-Hill, New York (1962); and Eliel and Wilen, *Stereochemistry of Organic Compounds*, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization.

A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy, and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in Greene and Wuts, *Protective Groups in Organic Synthesis*, 3rd Edition, John Wiley & Sons, New York (1999).

The terms "about" and "approximately" mean within a statistically meaningful range of a value. Such a range can be within an order of magnitude, preferably within 50%, more preferably within 20%, more preferably still within 10%, and even more preferably within 5% of a given value or range. The allowable variation encompassed by the terms "about" or "approximately" depends on the particular system under study and, where applicable, the particular measurement, and can be readily appreciated by one of ordinary skill in the art.

Methods of Treating Diseases

The compositions described herein can be used in a method for treating a disease. In some embodiments, the disease is a disease that may be treated using an exon-skipping oligomeric compound. In some embodiments, the disease is a disease that may be treated using an antisense-mediated exon-inclusion oligomeric compound. In an embodiment of the invention, the compositions described herein cross the blood-brain barrier, thus are useful in treating diseases of the central nervous system, behavioral disorders, psychiatric disorders, and/or behavioral symptoms of diseases. In some embodiments, the disease is a disease of the central nervous system (CNS). In some embodiments, the disease is amyotrophic lateral sclerosis (ALS), Alzheimer's Disease (AD), Parkinson's Disease (PD), Multiple Sclerosis (MS), epilepsy, Creutzfeldt-Jakob, (CJ), Menkes Disease, or Huntington's Disease (HD). In some embodiments, the disease is a disease affecting cerebellar function, including, but not limited to, ataxia. In some embodiments, the disease is a disease affecting amygdala function, including, but not limited to, Urbach-Wiethe Disease. In some embodiments, the disease is a disease affecting hippocampal function, including, but not limited to, memory loss. In some embodiments, the disease to be treated is a psychiatric or behavioral disorder, including, but not limited to, mood disorders, dementia, anxiety, bipolar disorder, schizophrenia, sleep disorders, post-traumatic stress disorder (PTSD), attention-deficit hyperactivity disorder (ADHD), and depression disorders.

In some embodiments of the invention, the oligonucleotides of the present invention are used to treat sleep and/or cognitive disorders, and symptoms associated therewith. In some embodiments, the sleep disorder is insomnia or slow wave sleep disturbance. In some embodiments, the cognitive disorder is schizophrenia. Where the disease being treated is schizophrenia, both positive and negative symptoms of schizophrenia may be treated. In some embodiments, positive symptoms of schizophrenia are hallucinations, delusions, or disturbances in logical thought process. In some embodiments, negative symptoms of schizophrenia include deficit in motivation, deficit in spontaneity, inability to think abstractly, deficit in mood expression, deficit in cognition, deficit in the ability to experience pleasure, affective flattening, alogia, avolition, dysphoric mood, including anger, anxiety, and depression, disturbances in sleep pattern, poor impulse control, lack of judgment, abnormal psychomotor activity, such as pacing or rocking, and movement disorders, such as tardive dyskinesia. In some embodiments, areas of cognition, such as verbal memory, verbal fluency, memory consolidation, and executive functions, are improved by administration of one or more of the oligonucleotide compounds of the present invention. In some embodiments, slow wave sleep is increased, thereby improving cognition, with administration of one or more of the oligonucleotide compounds of the present invention. In some embodiments, the disease is Duchenne muscular dystrophy, treatment of familial dysautonomia, spinal muscular atrophy, ataxia telangiectasia, congenital disorder of glycosylation, fronto-temporal dementia (FTD), Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), or myotonic dystrophy type 1 (DM1 or Steinert disease). Methods of using tc-DNA oligonucleotides for the treatment of Duchenne muscular dystrophy (DMD), spinal muscular atrophy (SMA), spinocerebellar ataxia type 3 (SCA3), and other diseases are known in the art and are described, e.g., in U.S. Pat. Nos. 4,981,957; 5, 118,800; 5,319,080; 5,359,044; 5,393,878; 5,446, 137; 5,466, 786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847; and 6,600,032; and U.S. Patent Application Publication Nos. 2015/0141637, 2016/0002280, 2014/0296323, and 2012/0149756, the disclosures of which are incorporated by reference herein.

Table A provides a listing of certain neurodegenerative diseases and their targets for which the compositions of the present invention are useful.

| Disease State | Target Gene |
|---|---|
| SMA | Survival of motor neuron 2 (SMN2) |
| ALS | Superoxide dismutase 1 (SOD1) |
| | Acetylcholinesterase (AChE) |
| | C9ORF72 |
| | Glutamate receptor subunit 3 (GluR3) |
| | P75 neurotrophin receptor (P75NTR) |
| HD | Mutant HTT |
| | HTT |
| AD | APP |
| | Mutated APP |
| | GSK-3β |
| CJ | PRPc |
| SCA3 | Ataxin 3 |
| Menkes Disease | ATP7A |
| FTD | Tau |

Efficacy of the compositions described herein in treating, preventing and/or managing the indicated diseases or disorders can be tested using various models known in the art, which provide guidance for treatment of human disease. Models for diseases that may be treated using an exon-skipping oligomeric compound are described, e.g., in Siva, et al., *Nucleic Acid Therapeutics* 2014, 24, 69-86. Models for diseases that may be treated using an antisense-mediated exon-inclusion oligomeric compound are described, e.g., in Hua and Krainer, *Methods Mol. Biol.* 2012, 867, 307-323.

Genetic animal models for DMD are known in the art. The mdx mouse harbors a nonsense mutation in exon 23 of the dystrophin gene, which precludes the synthesis of full-length, wild-type dystrophin protein. Grounds, et al., *Neurobiol. Dis.* 2008, 31, 1-19. The GRMD (Golden Retriever Muscle Dystrophy) dog model lacks functional dystrophin because of a splice site mutation in intron 6, which disrupts the reading frame. In the GRMD model, as with human DMD, the progressive degradation of fibers leads to skeletal musculature decay with marked endomysial and perimysial fibrosis. Other models for DMD include dystrophin/utrophin double knockout mice, humanized DMD mice, mdx52 mice (carrying a deletion of exon 52 in murine DMD), and 4CV mice (carrying a nonsense mutation in exon53). Goyenvalle, et al., *Mol. Ther.* 2010, 18, 198-05; Bremmer-Bout, et al., *Mol. Ther.* 2004, 10, 232-240; Aoki, et al., *Mol. Ther.* 2010, 18, 1995-2005; Mitrpant, et al., *J. Gene. Med.* 2009, 11, 46-56.

Tc-DNA Nucleosides

In an embodiment, the tc-DNA nucleosides of the oligomeric compounds of the invention comprise a compound of Formula (1):

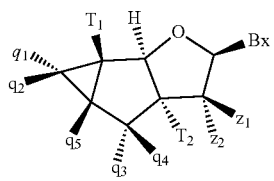

Formula (1)

wherein:
Bx is a heterocyclic base moiety;
one of $T_1$ and $T_2$ is an internucleoside linkage attaching the compound of Formula (1) to the oligomeric compound and the other of $T_1$ and $T_2$ is hydroxyl, a protected hydroxyl, a phosphate moiety, a 5'- or 3'-terminal group or an internucleoside linkage attaching said tricyclic nucleoside of Formula (1) to said oligomeric compound;
$q_1$, $q_2$, $q_3$, $q_4$, and $q_5$ are each independently selected from the group consisting of hydrogen (H), halogen, $(C_{1-6})$alkyl, $(C_{2-6})$alkenyl, $(C_{2-6})$alkynyl, substituted $(C_{1-6})$alkyl, substituted $(C_{2-6})$alkenyl, substituted $(C_{2-6})$alkynyl, and —$(CH_2)_n$—$C(O)$—$R_6'$, wherein n is 0 to 6 and wherein $R_6'$ is selected from the group consisting of OH, $NH_2$, and O—$(C_1$-$C_{16})$alkyl;
$z_1$ and $z_2$ are each independently selected from the group consisting of H, halogen, $(C_{1-6})$alkyl, $(C_{1-6})$alkoxyl, O—$(C_{2-6})$alkenyl, O—$(C_{2-6})$alkynyl, substituted $(C_{1-6})$alkyl, substituted $(C_{1-6})$alkoxy, substituted O—$(C_{2-6})$alkenyl, and substituted O—$(C_{2-6})$alkynyl;
or a pharmaceutically-acceptable salt thereof.

In an embodiment, the tc-DNA nucleosides of the oligomeric compounds of the invention comprise a compound of Formula (1), wherein $q_5$ is H.

In an embodiment, the tc-DNA nucleosides of the oligomeric compounds of the invention comprise a compound of Formula (1), wherein Bx is selected from the group consisting of thymine, adenine, guanine, and cytosine. In an embodiment, the tc-DNA nucleosides of the oligomeric compounds of the invention comprise a compound of Formula (1), wherein Bx is a modified base. In an embodiment, the tc-DNA nucleosides of the oligomeric compounds of the invention comprise a compound of Formula (1), wherein Bx is a modified base selected from the group consisting of 5-methylcytosine, 5-bromouracil, inosine, and 2,6-diaminopurine.

In an embodiment, the tc-DNA nucleosides of the oligomeric compounds of the invention comprise a compound of Formula (2):

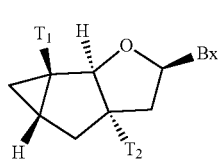

Formula (2)

wherein:
Bx is a heterocyclic base moiety;
one of $T_1$ and $T_2$ is an internucleoside linking group attaching the compound of Formula (2) to the oligomeric compound and the other of $T_1$ and $T_2$ is hydroxyl, a protected hydroxyl, a phosphate moiety, a 5' or 3'-terminal group or an internucleoside linking group attaching the compound of Formula (2) to the oligomeric compound.

In an embodiment, the tc-DNA nucleosides of the oligomeric compounds of the invention comprise a compound of Formula (2), wherein Bx is selected from the group consisting of thymine, adenine, guanine, and cytosine. In an embodiment, the tc-DNA nucleosides of the oligomeric compounds of the invention comprise a compound of Formula (2), wherein Bx is a modified base. In an embodiment, the tc-DNA nucleosides of the oligomeric compounds of the invention comprise a compound of Formula (2), wherein Bx is a modified base selected from the group consisting of 5-methylcytosine, 5-bromouracil, inosine, and 2,6-diaminopurine.

In an embodiment, the tc-DNA nucleosides of the oligomeric compounds of the invention comprise a compound of Formula (3) (also known as a C(6')-functionalized tc-DNA):

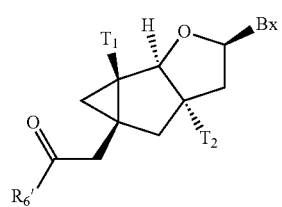

Formula (3)

wherein:
Bx is a heterocyclic base moiety;
$R_6'$ is selected from the group consisting of OH, $NH_2$, and O—$(C_1$-$C_{16})$alkyl;
one of $T_1$ and $T_2$ is an internucleoside linking group attaching the compound of Formula (3) to the oligomeric compound and the other of $T_1$ and $T_2$ is hydroxyl, a protected hydroxyl, a phosphate moiety, a 5' or 3'-terminal group or an internucleoside linking group attaching the compound of Formula (3) to the oligomeric compound.

In an embodiment, the tc-DNA nucleosides of the oligomeric compounds of the invention comprise a compound of Formula (3), wherein Bx is selected from the group consisting of thymine, adenine, guanine, and cytosine. In an embodiment, the tc-DNA nucleosides of the oligomeric compounds of the invention comprise a compound of Formula (3), wherein Bx is a modified base. In an embodiment, the tc-DNA nucleosides of the oligomeric compounds of the invention comprise a compound of Formula (3), wherein Bx is a modified base selected from the group consisting of 5-methylcytosine, 5-bromouracil, inosine, and 2,6-diaminopurine.

In an embodiment, the tc-DNA nucleosides of the oligomeric compounds of the invention comprise a compound of Formula (4) (also known as 6'-fluoro-tc-DNA):

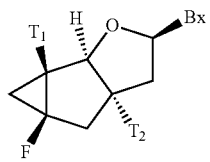

Formula (4)

wherein:
Bx is a heterocyclic base moiety;
one of $T_1$ and $T_2$ is an internucleoside linking group attaching the compound of Formula (4) to the oligomeric compound and the other of $T_1$ and $T_2$ is hydroxyl, a protected hydroxyl, a phosphate moiety, a 5' or 3'-terminal group or an internucleoside linking group attaching the compound of Formula (4) to the oligomeric compound.

In an embodiment, the tc-DNA nucleosides of the oligomeric compounds of the invention comprise a compound of Formula (4), wherein Bx is selected from the group consisting of thymine, adenine, guanine, and cytosine. In an embodiment, the tc-DNA nucleosides of the oligomeric compounds of the invention comprise a compound of Formula (4), wherein Bx is a modified base. In an embodiment, the tc-DNA nucleosides of the oligomeric compounds of the invention comprise a compound of Formula (4), wherein Bx is a modified base selected from the group consisting of 5-methylcytosine, 5-bromouracil, inosine, and 2,6-diaminopurine.

In an embodiment, the tc-DNA nucleosides of the oligomeric compounds of the invention comprise a compound of Formula (5) (also known as 2'-fluoro-tc-DNA):

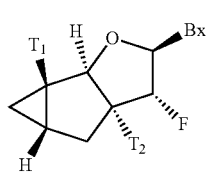

Formula (5)

wherein:
Bx is a heterocyclic base moiety;
one of $T_1$ and $T_2$ is an internucleoside linking group attaching the compound of Formula (5) to the oligomeric compound and the other of $T_1$ and $T_2$ is hydroxyl, a protected hydroxyl, a phosphate moiety, a 5' or 3'-terminal group or an internucleoside linking group attaching the compound of Formula (5) to the oligomeric compound.

In an embodiment, the tc-DNA nucleosides of the oligomeric compounds of the invention comprise a compound of Formula (5), wherein Bx is selected from the group consisting of thymine, adenine, guanine, and cytosine. In an embodiment, the tc-DNA nucleosides of the oligomeric compounds of the invention comprise a compound of Formula (5), wherein Bx is a modified base. In an embodiment, the tc-DNA nucleosides of the oligomeric compounds of the invention comprise a compound of Formula (5), wherein Bx is a modified base selected from the group consisting of 5-methylcytosine, 5-bromouracil, inosine, and 2,6-diaminopurine.

General methods of preparation of compounds of Formula (1) to Formula (5) for use with oligomeric compounds are known in the art, including the methods described in U.S. Patent Application Publication Nos. 2015/0141637, 2016/0002280, and 2014/0296323, the disclosures of which are incorporated by reference herein. Standard phosphoramidite building blocks for tc-DNA have been described in the art, e.g., in Steffens and Leumann, *Helv. Chim. Acta* 1997, 80, 2426-2439. Methods of preparing compounds of Formula (3) have been described, e.g., in Lietard and Leumann, *J. Org. Chem.* 2012, 77, 4566-77, the disclosure of which is incorporated by reference herein. Methods of preparing compounds of Formula (4) have been described, e.g., in Medvecky, Istrate, and Leumann, *J. Org. Chem.* 2015, 80, 3556-65, the disclosure of which is incorporated by reference herein. Methods of preparing compounds of Formula (5) have been described, e.g., in Istrate, Medvecky, and Leumann, *Org. Lett.* 2015, 17, 1950-53, the disclosure of which is incorporated by reference herein.

2'-Modified RNA Nucleosides

In an embodiment, the 2'-modified-RNA nucleosides of the oligomeric compounds of the invention comprise a compound of Formula (6) (a 2'-hydroxy-RNA nucleoside):

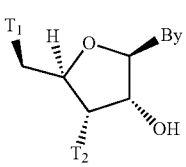

Formula (6)

In an embodiment, the 2'-modified-RNA nucleosides of the oligomeric compounds of the invention comprise a compound of Formula (6), wherein By is selected from the group consisting of cytosine, adenine, guanine, and uracil. In an embodiment, the 2'-modified-RNA nucleosides of the oligomeric compounds of the invention comprise a compound of Formula (6), wherein By is a modified base. In an embodiment, the 2'-modified-RNA nucleosides of the oligomeric compounds of the invention comprise a compound of Formula (6), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (7) (a 2'-O-methyl-RNA nucleoside):

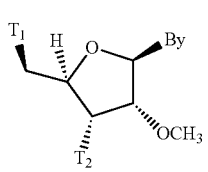

Formula (7)

In an embodiment, the 2'-modified-RNA nucleosides of the oligomeric compounds of the invention comprise a compound of Formula (7), wherein By is selected from the group consisting of cytosine, adenine, guanine, and uracil. In an embodiment, the 2'-modified-RNA nucleosides of the oligomeric compounds of the invention comprise a compound of Formula (7), wherein By is a modified base. In an embodiment, the 2'-modified-RNA nucleosides of the oligomeric compounds of the invention comprise a compound of Formula (7), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (8) (a 2'-O-propargyl-RNA nucleoside):

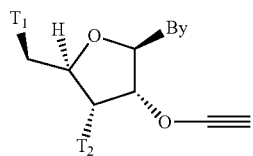

Formula (8)

In an embodiment, the 2'-modified-RNA nucleosides of the oligomeric compounds of the invention comprise a compound of Formula (8), wherein By is selected from the group consisting of cytosine, adenine, guanine, and uracil. In an embodiment, the 2'-modified-RNA nucleosides of the oligomeric compounds of the invention comprise a compound of Formula (8), wherein By is a modified base. In an embodiment, the 2'-modified-RNA nucleosides of the oligomeric compounds of the invention comprise a compound of Formula (8), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (9) (a 2'-O-propylamino-RNA nucleoside):

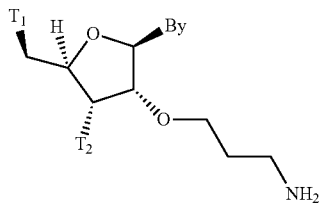

Formula (9)

In an embodiment, the 2'-modified-RNA nucleosides of the oligomeric compounds of the invention comprise a compound of Formula (9), wherein By is selected from the group consisting of cytosine, adenine, guanine, and uracil. In an embodiment, the 2'-modified-RNA nucleosides of the oligomeric compounds of the invention comprise a compound of Formula (9), wherein By is a modified base. In an embodiment, the 2'-modified-RNA nucleosides of the oligomeric compounds of the invention comprise a compound of Formula (9), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (10) (a 2'-O-amino-RNA nucleoside):

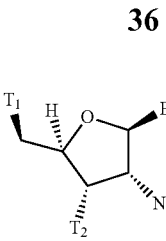

Formula (10)

In an embodiment, the 2'-modified-RNA nucleosides of the oligomeric compounds of the invention comprise a compound of Formula (10), wherein By is selected from the group consisting of cytosine, adenine, guanine, and uracil. In an embodiment, the 2'-modified-RNA nucleosides of the oligomeric compounds of the invention comprise a compound of Formula (10), wherein By is a modified base. In an embodiment, the 2'-modified-RNA nucleosides of the oligomeric compounds of the invention comprise a compound of Formula (10), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (11) (a 2'-fluoro-RNA nucleoside):

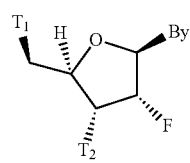

Formula (11)

In an embodiment, the 2'-modified-RNA nucleosides of the oligomeric compounds of the invention comprise a compound of Formula (11), wherein By is selected from the group consisting of cytosine, adenine, guanine, and uracil. In an embodiment, the 2'-modified-RNA nucleosides of the oligomeric compounds of the invention comprise a compound of Formula (11), wherein By is a modified base. In an embodiment, the 2'-modified-RNA nucleosides of the oligomeric compounds of the invention comprise a compound of Formula (11), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (12) (a 2'-O-methoxyethyl-RNA, or 2'-MOE, nucleoside):

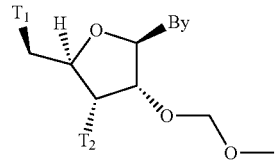

Formula (12)

In an embodiment, the 2'-modified-RNA nucleosides of the oligomeric compounds of the invention comprise a compound of Formula (12), wherein By is selected from the group consisting of cytosine, adenine, guanine, and uracil. In an embodiment, the 2'-modified-RNA nucleosides of the oligomeric compounds of the invention comprise a compound of Formula (12), wherein By is a modified base. In an embodiment, the 2'-modified-RNA nucleosides of the oligomeric compounds of the invention comprise a compound of Formula (12), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (13) (a morpholino nucleoside):

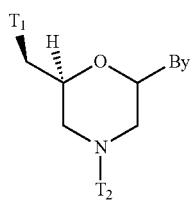

Formula (13)

In an embodiment, the 2'-modified-RNA nucleosides of the oligomeric compounds of the invention comprise a compound of Formula (13), wherein By is selected from the group consisting of cytosine, adenine, guanine, and uracil. In an embodiment, the 2'-modified-RNA nucleosides of the oligomeric compounds of the invention comprise a compound of Formula (13), wherein By is a modified base. In an embodiment, the 2'-modified-RNA nucleosides of the oligomeric compounds of the invention comprise a compound of Formula (13), wherein By is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (14) (a locked nucleic acid or LNA nucleoside):

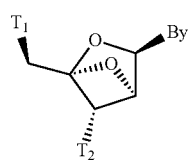

Formula (14)

In an embodiment, the 2'-modified-RNA nucleosides of the oligomeric compounds of the invention comprise a compound of Formula (14), wherein By is selected from the group consisting of cytosine, adenine, guanine, and uracil. In an embodiment, the 2'-modified-RNA nucleosides of the oligomeric compounds of the invention comprise a compound of Formula (14), wherein By is a modified base. In an embodiment, the 2'-modified-RNA nucleosides of the oligomeric compounds of the invention comprise a compound of Formula (14), wherein By is a modified base selected from the group consisting of 5-methylcytosine, 5-methyluracil, 5-bromouracil, inosine, and 2,6-diaminopurine.

General methods of preparation of compounds of Formula (6) to Formula (14) for use with oligomeric compounds are known in the art, including the methods described in U.S. Pat. Nos. 4,981,957; 5, 118,800; 5,319,080; 5,359,044; 5,393,878; 5,446, 137; 5,466, 786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847; and 6,600,032; U.S. Patent Application Publication Nos. 2015/0141637, 2016/0002280, and 2014/0296323; and Renneberg, et al., *J. Am. Chem. Soc.* 2002, 124, 5993-6002, the disclosures of which are incorporated by reference herein.

Non-Nucleosides

In an embodiment, the oligomeric compounds of the invention comprise non-nucleosides, also known in the art as non-nucleoside linkers, non-nucleotide linkers, and non-nucleotidylic linkers, which are highly flexible substitutes for the sugar carbons of, e.g., a ribofuranone moiety, and which can be used to replace the tc-DNA nucleosides and 2'-modified RNA nucleosides of the present oligomeric compounds. An exemplary non-nucleotide is the 1,3-propanediol group shown in Formula (15), which is shown joining two exemplary phosphorodiester internucleoside linkages:

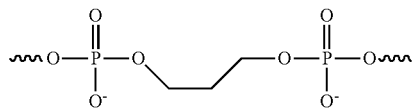

Formula (15)

The wavy lines in Formula (15) signify additional oligomeric repeating nucleoside and internucleoside linkages units as described herein.

The non-nucleotides of the present invention may be used with any of the internucleoside linkages described herein, including embodiments wherein the phosphorodiester internucleoside linkages shown in Formula (15) are replaced with one or more phosphorothioate internucleoside linkages.

In a preferred embodiment, a non-nucleotide is a 1,3-propanediol group (denoted by an "s"). The synthesis and incorporation of 1,3-propanediol groups into oligomeric compounds is known in the art and is described, e.g., in Seela and Kaiser, *Nuc. Acids Res.* 1987, 15, 3113-29. In an embodiment, the oligomeric compounds of the invention include 1, 2, 3, 4, 5, 6, 7, 8, 9, 10, 11, or 12 1,3-propanediol groups linked by phosphorothioate internucleoside linkages, phosphorodiester internucleoside linkages, or mixtures thereof.

Alternative non-nucleosides may also be used with the oligomeric compounds of the present invention, such as ethylene glycol oligomers of various lengths (i.e., one, two, three, or more ethylene glycol units joined to form a single non-nucleoside). Various suitable ethylene glycol groups are described, e.g., in Pils and Micura, *Nuc. Acids Res.* 2000, 28, 1859-63. The synthesis and use of non-nucleosides has also been described in, e.g., U.S. Pat. No. 5,573,906, the disclosure of which is incorporated by reference herein.

Internucleoside Linkages

In an embodiment, the internucleoside linkages of the oligomeric compounds of the invention comprise phosphate moieties independently selected from the group consisting of a phosphorothioate linkage, a phosphorodithioate linkage, a phosphorodiester linkage, a phosphotriester linkage, an aminoalkylphosphotriester linkage, a methyl phosphonate linkage, an alkyl phosphonate linkage, a 5'-alkylene phosphonate linkage, a phosphonate linkage, a phosphinate linkage, a phosphoramidate linkage, an 3'-aminophosphoramidate linkage, an aminoalkyl phosphoramidate linkage, a thionophosphoramidate linkage, a thionoalkylphosphonate linkage, a thionoalkylphosphotriester linkage, a selenophosphate linkage, and a boranophosphate linkage.

In a preferred embodiment, the internucleoside linkages of the oligomeric compounds of the invention comprise phosphate moieties independently selected from the group consisting of a phosphorothioate linkage and a phosphorodiester linkage. In an embodiment, the internucleoside linkages of the oligomeric compounds of the invention comprise phosphate moieties comprising only phosphorothioate linkages. In a preferred embodiment, the internucleoside linkages of the oligomeric compounds of the invention comprise phosphate moieties independently selected from the group consisting of a phosphorothioate linkage and a phosphorodiester linkage, wherein the percentage of phosphorothioate linkages relative to the total number of internucleoside linkages is selected from the group consisting of no more than about 90%, no more than about 80%, no more than about 75%, no more than about 70%, no more than about 65%, no more than about 60%, no more than about 55%, no more than about 50%, no more than about 49%, no more than about 48%, no more than about 47%, no more than about 46%, no more than about 45%, no more than about 44%, no more than about 43%, no more than about 42%, no more than about 41%, no more than about 40%, no more than about 39%, no more than about 38%, no more than about 37%, no more than about 36%, no more than about 35%, no more than about 34%, no more than about 33%, no more than about 32%, no more than about 31%, no more than about 30%, no more than about 25%, no more than about 20%, and no more than about 15%. In a preferred embodiment, the internucleoside linkages of the oligomeric compounds of the invention comprise phosphate moieties independently selected from the group consisting of a phosphorothioate linkage and a phosphorodiester linkage, wherein the percentage of phosphorothioate linkages relative to the total number of internucleoside linkages is selected from the group consisting of no more than 90%, no more than 80%, no more than 75%, no more than 70%, no more than 65%, no more than 60%, no more than 55%, no more than 50%, no more than 49%, no more than 48%, no more than 47%, no more than 46%, no more than 45%, no more than 44%, no more than 43%, no more than 42%, no more than 41%, no more than 40%, no more than 39%, no more than 38%, no more than 37%, no more than 36%, no more than 35%, no more than 34%, no more than 33%, no more than 32%, no more than 31%, no more than 30%, no more than 25%, no more than 20%, and no more than 15%.

In an embodiment, the internucleoside linkages of the oligomeric compounds of the invention comprise phosphate moieties comprising only phosphorodiester linkages. In a preferred embodiment, the internucleoside linkages of the oligomeric compounds of the invention comprise phosphate moieties independently selected from the group consisting of a phosphorothioate linkage and a phosphorodiester linkage, wherein the percentage of phosphorodiester linkages relative to the total number of internucleoside linkages is selected from the group consisting of at least about 5%, at least about 10%, at least about 15%, at least about 20%, at least about 25%, at least about 30%, at least about 35%, at least about 40%, at least about 45%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, and at least about 85%. In a preferred embodiment, the internucleoside linkages of the oligomeric compounds of the invention comprise phosphate moieties independently selected from the group consisting of a phosphorothioate linkage and a phosphorodiester linkage, wherein the percentage of phosphorodiester linkages relative to the total number of internucleoside linkages is selected from the group consisting of at least 5%, at least 10%, at least 15%, at least 20%, at least 25%, at least 30%, at least 35%, at least 40%, at least 45%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, and at least 85%.

An exemplary phosphorothioate linkage is shown in Formula (16):

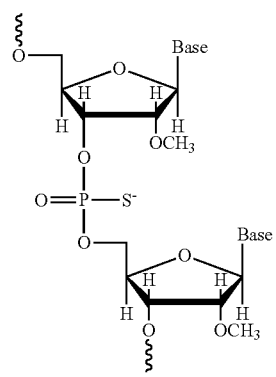

Formula (16)

An exemplary phosphorodiester linkage is shown in Formula (17):

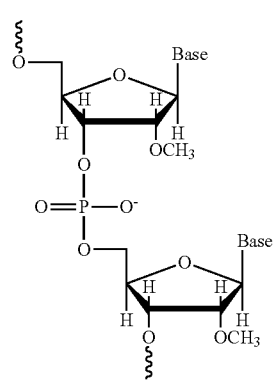

Formula (17)

The wavy lines in Formula (16) and Formula (17) signify additional oligomeric repeating nucleoside and internucleoside linkages units as described herein.

General methods of preparation of internucleoside linkages for use with oligomeric compounds are known in the art, including the methods described in U.S. Pat. Nos.

3,687,808; 4,469,863; 4,476,301; 5,023,243; 5,177,196; 5,188,897; 5,264,423; 5,276,019; 5,278,302; 5,286, 717; 5,321, 131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5, 194,599; 5,565,555; 5,527,899; 5,721,218; 5,672,697 and 5,625,050, the disclosures of which are incorporated by reference herein. Phosphorothioates may be prepared from phosphate triesters, for example, using phenylacetyl disulfide (PADS) chemistry described in Krotz, et al., *Org. Proc. R & D* 2004, 8, 852-58, as part of solid-phase syntheses using, e.g., the four-reaction 3'- to 5'-elongation cycle (detritylation, coupling, sulfurization using PADS, and capping, followed by deprotection, cleavage from the support, and purification steps.

Oligomeric Compounds

In an embodiment, the invention includes an oligomeric compound comprising a plurality of tc-DNA nucleosides and a plurality of 2'-modified-RNA nucleosides joined by a plurality of internucleoside linkages. Suitable tc-DNA nucleosides and 2'-modified-RNA nucleosides are described herein. In an embodiment, the invention includes a pharmaceutically acceptable salt of an oligomeric compound comprising a plurality of tc-DNA nucleosides and a plurality of 2'-modified-RNA nucleosides joined by a plurality of internucleoside linkages. Oligomeric compounds comprising a plurality of tc-DNA nucleosides and a plurality of 2'-modified-RNA nucleosides may be prepared by methods used for other tc-DNA or RNA oligonucleotides, such as those described or incorporated by reference elsewhere herein. Suitable methods for preparation of oligomeric tc-DNA and 2'-modified-RNA compounds that may be adapted for use with the present oligomeric compounds are also described in Renneberg, et al., *J. Am. Chem. Soc.* 2002, 124, 5993-6002 and *Handbook of Analysis of Oligonucleotides and Related Products*, CRC Press, 2011, the disclosures of which are incorporated by reference herein. Solid-phase syntheses using the four-reaction 3'- to 5'-elongation cycle (detritylation, coupling, sulfurization using PADS if desired, and capping, followed by deprotection, cleavage from the support, and purification of the oligomeric compound. Phosphoroamidite chemistry suitable for the foregoing processes is described, e.g., in U.S. Pat. No. 4,725,677, the disclosure of which is incorporated by reference herein. In general, such chemistry includes the steps of providing a solid support wherein an attached nucleoside is subjected to removal of the protecting group on the 5'-hydroxyl position. The incoming phosphoramidite is coupled to the growing chain in the presence of an activator. Any unreacted 5'-hydroxyl groups are capped and the phosphite triester is then oxidized (or sulfurized, e.g., using PADS) to provide the desired phosphotriester linkage. The steps are repeated until an oligomer of the desired length results. The reagents used may vary according to the choice of protecting groups. Once the oligonucleotide has been synthesized, it may be deprotected using a two-step process that entails cleavage of the oligomer from the support and deprotection of the base and phosphate blocking groups, followed by removal of the 2'-protecting groups. Occasionally, a different order of reactions or separate deprotection of the phosphate groups is required. Finally, purification and isolation are performed. Suitable purification methods are known in the art and may include chromatographic (such as reversed phase chromatography and ion-pairing chromatography) and desalting processes, including those described in U.S. Pat. Nos. 5,804, 683, 5,977,343, and 7,893,249, the disclosures of which are incorporated by reference herein. Suitable isolation methods are known in the art and may include lyophilization, precipitation, and spray-drying. Such processes may result in the formation of amorphous oligomeric compounds (i.e., lacking long-range order characteristic of crystalline material) that are also mixtures of salts or are partial (i.e., non-stoichiometric) salts. In an embodiment, the oligomeric compound is a pharmaceutically acceptable salt or mixture of salts of an oligomeric compound of the present disclosure.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 50° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 55° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 60° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 65° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 70° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 75° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 80° C.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than about 50° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 55° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 60° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 65° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 70° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 75° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is greater than 80° C.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 45° C. and about 50° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 50° C. and about 55° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 55° C. and about 60° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 60° C. and about 65° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 65° C. and about 70° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 70° C. and about 75° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 75° C. and about 80° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 80° C. and about 85° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between about 85° C. and about 90° C.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 45 OC and 50° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 50° C. and 55 OC. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 55 OC and 60° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 60° C. and 65° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 65 OC and 70° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 70° C. and 75 OC. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 75 OC and 80° C. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 80° C. and 85 OC. In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is between 85 OC and 90° C.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is selected from the group consisting of about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., and about 90° C.

In an embodiment, the invention includes an oligomeric compound comprising a plurality of tc-DNA nucleosides and a plurality of 2'-modified-RNA nucleosides joined by a plurality of internucleoside linkages, wherein the melting temperature ($T_m$) is selected from the group consisting of 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., and 90° C.

In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is selected from the group consisting of about 1° C., about 2° C., about 3° C., about 4° C., about 5° C., about 6° C., about 7° C., about 8° C., about 9° C., about 10° C., about 11° C., about 12° C., about 13° C., about 14° C., and about 15° C.

In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is selected from the group consisting of 1 OC, 2° C., 3° C., 4° C., 5° C., 6° C., 7° C., 8° C., 9° C., 10° C., 11° C., 12° C., 13° C., 14° C., and 15° C.

In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 2° C. and 3° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 3° C. and 4° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 4° C. and 5° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 5° C. and 6° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 6° C. and 7° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 7° C. and 8° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 8° C. and 9° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 9° C. and 10° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 10° C. and 11° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 11° C. and 12° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 12° C. and 13° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 13° C. and 14° C. In an embodiment, the invention includes an oligomeric compound comprising a plurality of tc-DNA nucleosides and a plurality of 2'-modified-RNA nucleosides joined by a plurality of internucleoside linkages, wherein the increase in melting temperature per modification ($\Delta T_m$/mod) against target natural RNA is between 14° C. and 15° C.

In an embodiment, the invention includes an oligomeric compound comprising a plurality of tc-DNA nucleosides and a plurality of 2'-modified-RNA nucleosides joined by a plurality of internucleoside linkages, wherein the size of the oligomeric compound is selected from the group consisting of an 8-mer, a 9-mer, a 10-mer, a 11-mer, a 12-mer, a 13-mer, a 14-mer, a 15-mer, a 16-mer, a 17-mer, a 18-mer, a 19-mer, a 20-mer, a 21-mer, a 22-mer, a 23-mer, a 24-mer, a 25-mer, a 26-mer, a 27-mer, a 28-mer, a 29-mer, and a 30-mer.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 6 to about 16 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 8 to about 18 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 10 to about 20 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 12 to about 22 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 14 to about 24 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 16 to about 26 linked monomeric subunits.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 14 to about 16 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 16 to about 18 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 18 to about 20 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 20 to about 22 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 22 to about 24 linked monomeric subunits. In an embodiment, the invention includes an oligomeric compound comprising a plurality of tc-DNA nucleosides and a plurality of 2'-modified-RNA nucleosides joined by a plurality of internucleoside linkages, wherein the oligomeric compound comprises from 24 to about 26 linked monomeric subunits.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is selected from the oligomeric compounds listed in Table 1.

TABLE 1

Embodiments of oligonucleotide sequences of the present invention. All oligonucleotides may use phosphorothioate linkages, phosphorodiester linkages, or other internucleoside linkages, or mixtures thereof, and any suitable base analog may be employed in addition to the nucleobase shown.

| Identifier | Sequence (A, G, C, T = tc-DNA; a, g, c, u = 2'-modified-RNA) |
|---|---|
| SEQ ID NO: 1 | AAG aTG GCA TTT CTA |
| SEQ ID NO: 2 | AAG AuG GCA TTT CTA |
| SEQ ID NO: 3 | AAG ATg GCA TTT CTA |
| SEQ ID NO: 4 | AAG ATG GcA TTT CTA |
| SEQ ID NO: 5 | AAG auG GCA TTT CTA |
| SEQ ID NO: 6 | AAG aTg GCA TTT CTA |
| SEQ ID NO: 7 | AAG aTg GcA TTT CTA |
| SEQ ID NO: 8 | AAG aug GCA TTT CTA |
| SEQ ID NO: 9 | AAG auG GcA TTT CTA |
| SEQ ID NO: 10 | AAG AuG GcA uTT CTA |
| SEQ ID NO: 11 | AaG aug GCA TTT CTA |
| SEQ ID NO: 12 | AAG ATG Gca uTu CTA |
| SEQ ID NO: 13 | AaG aug GCA TTT CTA |
| SEQ ID NO: 14 | AAG ATG GCA uTu CuA |

TABLE 1-continued

Embodiments of oligonucleotide sequences of the present invention. All oligonucleotides may use phosphorothioate linkages, phosphorodiester linkages, or other internucleoside linkages, or mixtures thereof, and any suitable base analog may be employed in addition to the nucleobase shown.

| Identifier | Sequence (A, G, C, T = tc-DNA; a, g, c, u = 2'-modified-RNA) |
|---|---|
| SEQ ID NO: 15 | GAA GAT GGC Auu ucT |
| SEQ ID NO: 16 | AAG ATG GCA uTT CTA |
| SEQ ID NO: 17 | AAG ATG GCa TTT CTA |
| SEQ ID NO: 18 | AAG Aug GCA TTT CTA |
| SEQ ID NO: 19 | AAG ATG GCa uTT CTA |
| SEQ ID NO: 20 | AAG ATG GcA uTT CTA |
| SEQ ID NO: 21 | AAG ATG Gca TTT CTA |
| SEQ ID NO: 22 | AAG aTG GCa TTT CTA |
| SEQ ID NO: 23 | AAG AuG GCA uTT CTA |
| SEQ ID NO: 24 | AAG AuG GcA TTT CTA |
| SEQ ID NO: 25 | AAG ATg GCA uTT CTA |
| SEQ ID NO: 26 | AAG ATg GCa TTT CTA |
| SEQ ID NO: 27 | AAG ATG Gca uTT CTA |
| SEQ ID NO: 28 | AAG aTg GCa TTT CTA |
| SEQ ID NO: 29 | AAG Aug GCA uTT CTA |
| SEQ ID NO: 30 | AGG AAG ATG GCA uuu cuA |

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is selected from the oligomeric compounds listed in Table 1A.

TABLE 1A

Embodiments of oligonucleotide sequences of the present invention. All oligonucleotides may use phosphorothioate linkages, phosphorodiester linkages, or other internucleoside linkages, or mixtures thereof, and any suitable base analog may be employed in addition to the nucleobase shown.

| Identifier | Sequence (A, G, C, T = tc-DNA; a, g, c, u = 2'-modified-RNA) |
|---|---|
| SEQ ID NO: 112 | CAT CCT GGA GTT CCT |
| SEQ ID NO: 113 | CAT CCT GgA GTT CCT |
| SEQ ID NO: 114 | GCC ATC CTG GAG TTC |
| SEQ ID NO: 115 | GCC ATC CTG gAG TTC |
| SEQ ID NO: 116 | CCG CTG CCC AAT GCC |
| SEQ ID NO: 117 | TGC CGC TGC CCA ATG |

TABLE 1A-continued

Embodiments of oligonucleotide sequences of the present invention. All oligonucleotides may use phosphorothioate linkages, phosphorodiester linkages, or other internucleoside linkages, or mixtures thereof, and any suitable base analog may be employed in addition to the nucleobase shown.

| Identifier | Sequence (A, G, C, T = tc-DNA; a, g, c, u = 2'-modified-RNA) |
|---|---|
| SEQ ID NO: 118 | CTG GAG TTC CTG TAA |
| SEQ ID NO: 119 | CTG gAG TTC CTG TAA |
| SEQ ID NO: 120 | TCC TGG AGT TCC TGT |
| SEQ ID NO: 121 | TCC TGg AGT TCC TGT |
| SEQ ID NO: 122 | ACT TCA TCC CAC TGA |
| SEQ ID NO: 123 | ACT TcA TCC CAC TGA |
| SEQ ID NO: 124 | ATT TCA TTC AAC TGT |
| SEQ ID NO: 125 | GTG TTC TTG TAC TTC |
| SEQ ID NO: 126 | GTG TTC TTG TaC TTC |
| SEQ ID NO: 127 | CTG AAG GTG TTC TTG |
| SEQ ID NO: 128 | CTG AaG GTG TTC TTG |
| SEQ ID NO: 129 | CTC CGG TTC TGA AGG |
| SEQ ID NO: 130 | CTC CGG TTc TGA AGG |
| SEQ ID NO: 131 | TTG AAT CCT TTA ACA |
| SEQ ID NO: 132 | TTG AAT CCT uTA ACA |
| SEQ ID NO: 133 | CTT TCA TAA TGC TGG |
| SEQ ID NO: 134 | CTT TCa TAA TGC TGG |
| SEQ ID NO: 135 | CTT TCA TAA uGC TGG |

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is selected from the oligomeric compounds listed in Table 2.

TABLE 2

Embodiments of oligonucleotide sequences of the present invention. PS refers to phosphorothioate linkages, and PO refers to phosphorodiester linkages. A, G, C, and T refer to tc-DNA; a, g, c, and u refer to 2'-O-Me-RNA; and s refers to —O—CH$_2$—CH$_2$—CH$_2$—O— (a 1,3-propanediol non-nucleoside). All tc-DNA cytosine positions ("C") use the 5-methylcytosine base analog, and all 2'-O-Me RNA positions ("c") use cytosine.

| Identifier | Name | Sequence | Notes |
|---|---|---|---|
| SEQ ID NO: 31 | SY-0329 | AAG aTG GCA TTT CTA | Full PS |
| SEQ ID NO: 32 | SY-0330 | AAG AuG GCA TTT CTA | Full PS |
| SEQ ID NO: 33 | SY-0331 | AAG ATg GCA TTT CTA | Full PS |
| SEQ ID NO: 34 | SY-0332 | AAG ATG GcA TTT CTA | Full PS |
| SEQ ID NO: 35 | SY-0333 | AAG auG GCA TTT CTA | Full PS |
| SEQ ID NO: 36 | SY-0334 | AAG aTg GCA TTT CTA | Full PS |
| SEQ ID NO: 37 | SY-0335 | AAG aTG GcA TTT CTA | Full PS |
| SEQ ID NO: 38 | SY-0337 | AAG aug GCA TTT CTA | Full PS |
| SEQ ID NO: 39 | SY-0338 | AAG auG GcA TTT CTA | Full PS |
| SEQ ID NO: 40 | SY-0339 | AAG AuG GcA uTT CTA | Full PS |
| SEQ ID NO: 41 | SY-0340 | AaG aug GCA TTT CTA | Full PS |
| SEQ ID NO: 42 | SY-0341 | AAG ATG Gca uTu CTA | Full PS |
| SEQ ID NO: 43 | SY-0371 | A*a*G* a*u*g* GCA TTT CTA | PO, but with PS at * |
| SEQ ID NO: 44 | SY-0372 | AAG ATG GCA* u*T*u* C*u*A | PO, but with PS at * |
| SEQ ID NO: 45 | SY-0373 | G AAG ATG GCA* u*u*u* c*T | PO, but with PS at * |
| SEQ ID NO: 46 | SY-0374 | AGG AAG ATG GCA* u*u*u* c*u*A | PO, but with PS at * |
| SEQ ID NO: 47 | SY-0388 | AGG AAG ATG G*c*a* u*u*u* CTA | PO, but with PS at * |
| SEQ ID NO: 48 | SY-0389 | AGG AAG ATG G*c*a* u*u*u* c*u*A | PO, but with PS at * |
| SEQ ID NO: 49 | SY-0390 | A*a*G* a*u*g* GCA TTT CTA GTT | PO, but with PS at * |
| SEQ ID NO: 50 | SY-0391 | A*a*g* a*u*g* GCA TTT CTA GTT | PO, but with PS at * |
| SEQ ID NO: 51 | SY-0392 | AA*g* a*u*g* GCA TTT CTA GTT | PO, but with PS at * |
| SEQ ID NO: 52 | SY-0393 | AGG AAG* a*u*g* GCA TTT CTA | PO, but with PS at * |
| SEQ ID NO: 53 | SY-0394 | AGG A*a*g* a*u*g* GCA TTT CTA | PO, but with PS at * |
| SEQ ID NO: 54 | SY-0395 | GG A*a*g* a*u*g* GCA TTT CTA | PO, but with PS at * |

TABLE 2-continued

Embodiments of oligonucleotide sequences of the present invention. PS refers to phosphorothioate linkages, and PO refers to phosphorodiester linkages. A, G, C, and T refer to tc-DNA; a, g, c, and u refer to 2'-O-Me-RNA; and s refers to —O—CH$_2$—CH$_2$—CH$_2$—O— (a 1,3-propanediol non-nucleoside). All tc-DNA cytosine positions ("C") use the 5-methylcytosine base analog, and all 2'-O-Me RNA positions ("c") use cytosine.

| Identifier | Name | Sequence | Notes |
|---|---|---|---|
| SEQ ID NO: 55 | SY-0396 | GG A*a*g* a*u*g* GCA TTT CT | PO, but with PS at * |
| SEQ ID NO: 56 | SY-0397 | AGG AA*g* a*u*g* g*CA TTT CTA | PO, but with PS at * |
| SEQ ID NO: 57 | SY-0398 | AGG A*a*g* a*u*g* g*CA TTT CTA | PO, but with PS at * |
| SEQ ID NO: 58 | SY-0406 | AGG AAG ATG G*c*a* u*u*u* c*u | PO, but with PS at * |
| SEQ ID NO: 59 | SY-0405 | a*g* a*u*g* GCA TTT CTA GTT | PO, but with PS at * |
| SEQ ID NO: 60 | SY-0407 | AAG AuG GCA TTT CTA | PO, but with PS at * |
| SEQ ID NO: 61 | SY-0408 | s*s* AAG AuG GCA TTT CTA | PO, but with PS at * |
| SEQ ID NO: 62 | SY-0410 | s* s*s*s* AAG AuG GCA TTT CTA | PO, but with PS at * |
| SEQ ID NO: 63 | SY-0412 | s*s*s* s*s*s* AAG AuG GCA TTT CTA | PO, but with PS at * |
| SEQ ID NO: 64 | SY-0414 | s*s* s*s*s* s*s*s* AAG AuG GCA TTT CTA | PO, but with PS at * |
| SEQ ID NO: 65 | SY-0416 | s* s*s*s* s*s*s* s*s*s* AAG AuG GCA TTT CTA | PO, but with PS at * |
| SEQ ID NO: 66 | SY-0417 | A*A*G* A*T*G* G*C*A* u*T*T* C*T*A | PO, but with PS at * |
| SEQ ID NO: 67 | SY-0418 | A*A*G* A*T*G* G*C*a* T*T*T* C*T*A | PO, but with PS at * |

SEQ ID NO:66 and SEQ ID NO:67 are embodiments of SEQ ID NO:16 and SEQ ID NO: 17, respectively.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is selected from the oligomeric compounds listed in Table 2A.

TABLE 2A

Embodiments of oligonucleotide sequences of the present invention. PS refers to phosphorothioate linkages. A, G, C, and T refer to tc-DNA; a, g, c, and u refer to 2'-O-Me-RNA. All tc-DNA cytosine positions ("C") use the 5-methylcytosine base analog, and all 2'-O-Me RNA positions ("c") use cytosine.

| Identifier | Name | Sequence | Notes |
|---|---|---|---|
| SEQ ID NO: 88 | SY-0462 | CAT CCT GGA GTT CCT | Full PS |
| SEQ ID NO: 89 | SY-0463 | CAT CCT GgA GTT CCT | Full PS |
| SEQ ID NO: 90 | SY-0464 | GCC ATC CTG GAG TTC | Full PS |
| SEQ ID NO: 91 | SY-0465 | GCC ATC CTG gAG TTC | Full PS |
| SEQ ID NO: 92 | SY-0466 | CCG CTG CCC AAT GCC | Full PS |
| SEQ ID NO: 93 | SY-0467 | TGC CGC TGC CCA ATG | Full PS |
| SEQ ID NO: 94 | SY-0471 | CTG GAG TTC CTG TAA | Full PS |
| SEQ ID NO: 95 | SY-0472 | CTG gAG TTC CTG TAA | Full PS |
| SEQ ID NO: 96 | SY-0473 | TCC TGG AGT TCC TGT | Full PS |
| SEQ ID NO: 97 | SY-0474 | TCC TGg AGT TCC TGT | Full PS |
| SEQ ID NO: 98 | SY-0468 | ACT TCA TCC CAC TGA | Full PS |
| SEQ ID NO: 99 | SY-0469 | ACT TcA TCC CAC TGA | Full PS |
| SEQ ID NO: 100 | SY-0470 | ATT TCA TTC AAC TGT | Full PS |
| SEQ ID NO: 101 | SY-0475 | GTG TTC TTG TAC TTC | Full PS |
| SEQ ID NO: 102 | SY-0476 | GTG TTC TTG TaC TTC | Full PS |
| SEQ ID NO: 103 | SY-0477 | CTG AAG GTG TTC TTG | Full PS |
| SEQ ID NO: 104 | SY-0478 | CTG AaG GTG TTC TTG | Full PS |
| SEQ ID NO: 105 | SY-0479 | CTC CGG TTC TGA AGG | Full PS |
| SEQ ID NO: 106 | SY-0480 | CTC CGG TTc TGA AGG | Full PS |
| SEQ ID NO: 107 | SY-0481 | TTG AAT CCT TTA ACA | Full PS |
| SEQ ID NO: 108 | SY-0482 | TTG AAT CCT uTA ACA | Full PS |
| SEQ ID NO: 109 | SY-0221 | CTT TCA TAA TGC TGG | Full PS |
| SEQ ID NO: 110 | SY-0483 | CTT TCa TAA TGC TGG | Full PS |
| SEQ ID NO: 111 | SY-0484 | CTT TCA TAA uGC TGG | Full PS |

For illustrative purposes, a single diastereomer of SY-0371 (SEQ ID NO:43) (which encompasses a mixture of diastereomers) is shown below as Formula (18):

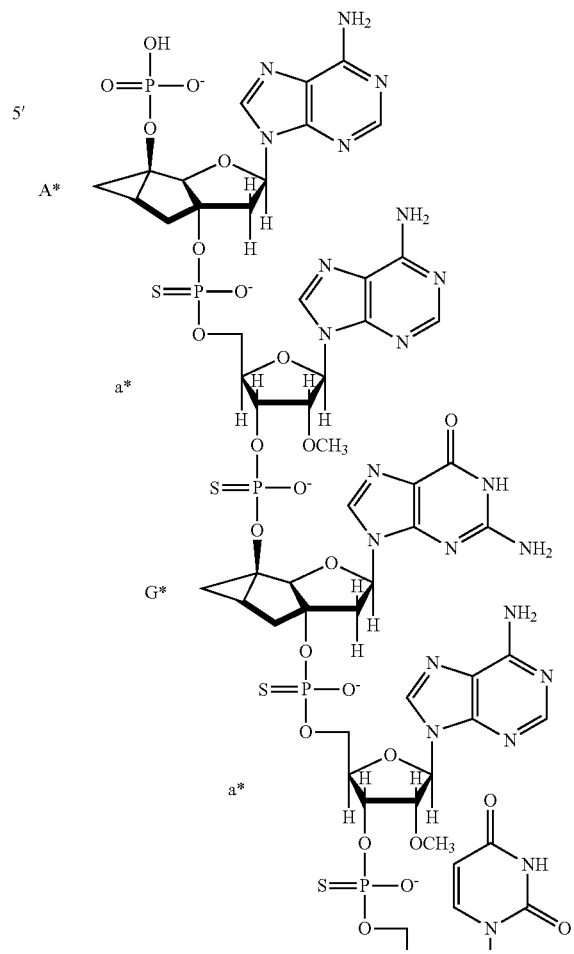

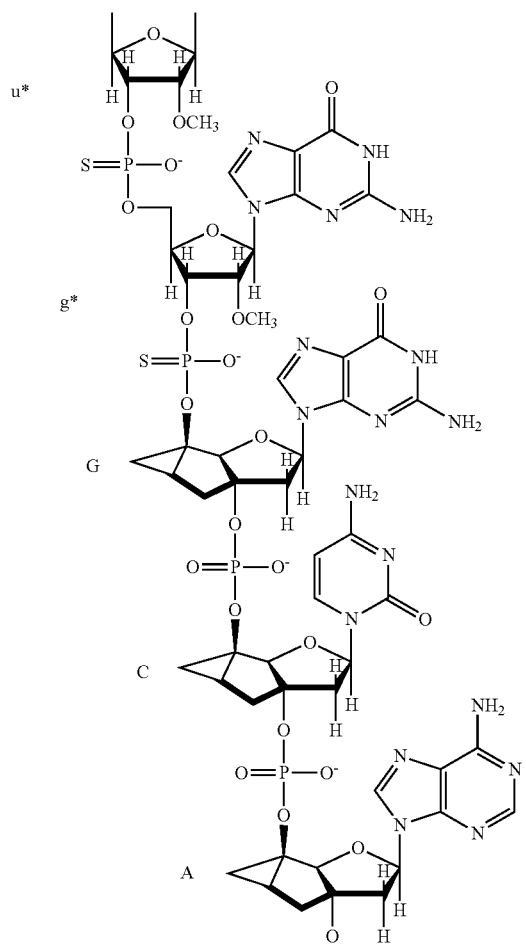
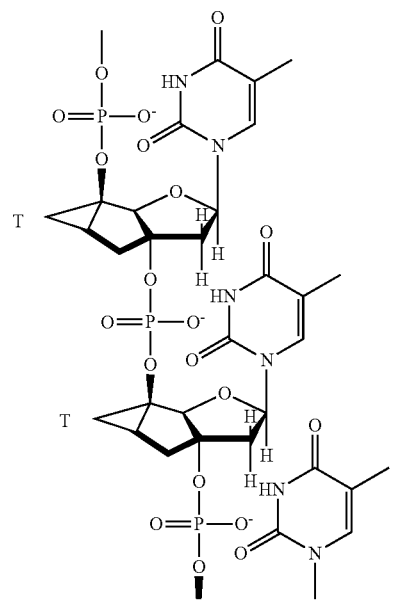

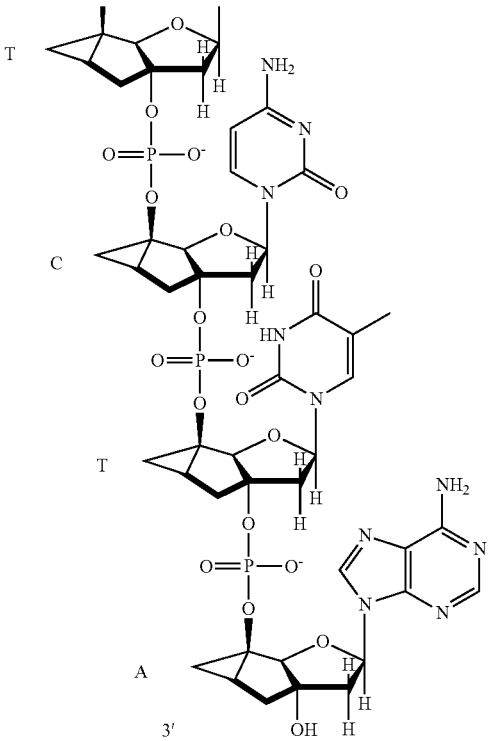

In an embodiment, the invention includes an oligomeric compound comprising a plurality of tc-DNA nucleosides and a plurality of 2'-modified-RNA nucleosides joined by a plurality of internucleoside linkages, wherein the oligomeric compound in not toxic in an animal model at a dose that would be therapeutically effective in a human.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is a monomer as determined by non-denaturing polyacrylamide gel electrophoresis (PAGE). In an embodiment, the invention includes an oligomeric compound comprising a plurality of tc-DNA nucleosides and a plurality of 2'-modified-RNA nucleosides joined by a plurality of internucleoside linkages, wherein the oligomeric compound does not exhibit any multimer bands as determined by non-denaturing polyacrylamide gel electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits minor multimer bands as determined by non-denaturing polyacrylamide gel electrophoresis.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is a monomer as determined by size exclusion chromatography (SEC). In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 99% monomer as determined by size exclusion chromatography.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 98% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 97% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 96% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 95% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 90% monomer as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 85% monomer as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 80% monomer as determined by size-exclusion chromatography.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 99% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 98% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 97% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 96% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 95% monomer as determined by size exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 90% monomer as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 85% monomer as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 80% monomer as determined by size-exclusion chromatography.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 250 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 200 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 150 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 100 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 75 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 50 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 25 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 20 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 15 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 10 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 5 to 1 as determined by size-exclusion chromatography.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 250 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 200 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 150 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 100 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 75 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 50 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 25 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 20 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 15 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 10 to 1 as determined by size-exclusion chromatography. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 5 to 1 as determined by size-exclusion chromatography.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is a monomer as determined by capillary electrophoresis (CE). In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 99% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 98% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 97% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 96% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 95% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 90% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 85% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least about 80% monomer as determined by capillary electrophoresis.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 99% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 98% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 97% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 96% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 95% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 90% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 85% monomer as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound is at least 80% monomer as determined by capillary electrophoresis.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 250 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 200 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 150 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 100 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 75 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 50 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 25 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 20 to 1 as i81 determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 15 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 10 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of at least 5 to 1 as determined by capillary electrophoresis.

In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 250 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 200 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 150 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 100 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 75 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 50 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 25 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 20 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 15 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 10 to 1 as determined by capillary electrophoresis. In an embodiment, the invention includes an oligomeric compound comprising a plurality of tc-DNA nucleosides and a plurality of 2'-modified-RNA nucleosides joined by a plurality of internucleoside linkages, wherein the oligomeric compound exhibits a monomer to multimer ratio of about 5 to 1 as determined by capillary electrophoresis.

In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro human serum is selected from the group consisting of at least about 95%, at least about 90%, at least about 85%, at least about 80%, at least about 75%, at least about 70%, at least about 65%, at least about 60%, at least about 55%, and at least about 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro monkey serum is selected from the group consisting of at least about 95%, at least about 90%, at least about 85%, at least about 80%, at least about 75%, at least about 70%, at least about 65%, at least about 60%, at least about 55%, and at least about 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro dog serum is selected from the group consisting of at least about 95%, at least about 90%, at least about 85%, at least about 80%, at least about 75%, at least about 70%, at least about 65%, at least about 60%, at least about 55%, and at least about 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro mouse serum is selected from the group consisting of at least about 95%, at least about 90%, at least about 85%, at least about 80%, at least about 75%, at least about 70%, at least about 65%, at least about 60%, at least about 55%, and at least about 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro rat serum is selected from the group consisting of at least about 95%, at least about 90%, at least about 85%, at least about 80%, at least about 75%, at least about 70%, at least about 65%, at least about 60%, at least about 55%, and at least about 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro human serum is selected from the group consisting of at least 95%, at least 90%, at least 85%, at least 80%, at least 75%, at least 70%, at least 65%, at least 60%, at least 55%, and at least 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro monkey serum is selected from the group consisting of at least 95%, at least 90%, at least 85%, at least 80%, at least 75%, at least 70%, at least 65%, at least 60%, at least 55%, and at least 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro dog serum is selected from the group consisting of at least 95%, at least 90%, at least 85%, at least 80%, at least 75%, at least 70%, at least 65%, at least 60%, at least 55%, and at least 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro mouse serum is selected from the group consisting of at least 95%, at least 90%, at least 85%, at least 80%, at least 75%, at least 70%, at least 65%, at least 60%, at least 55%, and at least 50%. In an embodiment, the invention includes an oligomeric compound comprising a plurality of tc-DNA nucleosides and a plurality of 2'-modified-RNA nucleosides joined by a plurality of internucleoside linkages, wherein the C3 percentage determined in a complement assay in in vitro rat serum is selected from the group consisting of at least 95%, at least 90%, at least 85%, at least 80%, at least 75%, at least 70%, at least 65%, at least 60%, at least 55%, and at least 50%. The foregoing values are relative to non-activated complement at 100%.

In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro human serum is selected from the group consisting of at least about 95%, not greater than about 10%, not greater than about 15%, not greater than about 20%, not greater than about 25%, not greater than about 30%, not greater than about 35%, not greater than about 40%, not greater than about 45%, and not greater than about 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro monkey serum is selected from the group consisting of at least about 95%, not greater than about 10%, not greater than about 15%, not greater than about 20%, not greater than about 25%, not greater than about 30%, not greater than about 35%, not greater than about 40%, not greater than about 45%, and not greater than about 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro dog serum is selected from the group consisting of at least about 95%, not greater than about 10%, not greater than about 15%, not greater than about 20%, not greater than about 25%, not greater than about 30%, not greater than about 35%, not greater than about 40%, not greater than about 45%, and not greater than about 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro mouse serum is selected from the group consisting of at least about 95%, not greater than about 10%, not greater than about 15%, not greater than about 20%, not greater than about 25%, not greater than about 30%, not greater than about 35%, not greater than about 40%, not greater than about 45%, and not greater than about 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro rat serum is selected from the group consisting of at least about 95%, not greater than about 10%, not greater than about 15%, not greater than about 20%, not greater than about 25%, not greater than about 30%, not greater than about 35%, not greater than about 40%, not greater than about 45%, and not greater than about 50%, relative to non-activated complement at 100%.

In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro human serum is selected from the group consisting of at least 95%, not greater than 10%, not greater than 15%, not greater than 20%, not greater than 25%, not greater than 30%, not greater than 35%, not greater than 40%, not greater than 45%, and not greater than 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro monkey serum is selected from the group consisting of at least 95%, not greater than 10%, not greater than 15%, not greater than 20%, not greater than 25%, not greater than 30%, not greater than 35%, not greater than 40%, not greater than 45%, and not greater than 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro dog serum is selected from the group consisting of at least 95%, not greater than 10%, not greater than 15%, not greater than 20%, not greater than 25%, not greater than 30%, not greater than 35%, not greater than 40%, not greater than 45%, and not greater than 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro mouse serum is selected from the group consisting of at least 95%, not greater than 10%, not greater than 15%, not greater than 20%, not greater than 25%, not greater than 30%, not greater than 35%, not greater than 40%, not greater than 45%, and not greater than 50%, relative to non-activated complement at 100%. In an embodiment, the invention includes an oligomeric compound comprising a plurality of tc-DNA nucleosides and a plurality of 2'-modified-RNA nucleosides joined by a plurality of internucleoside linkages, wherein the reduction in C3 percentage determined in a complement assay in in vitro rat serum is selected from the group consisting of at least 95%, not greater than 10%, not greater than 15%, not greater than 20%, not greater than 25%, not greater than 30%, not greater than 35%, not greater than 40%, not greater than 45%, and not greater than 50%, relative to non-activated complement at 100%.

In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro human serum is selected from the group consisting of at least about 4000 ng/mL, at least about 3800 ng/mL, at least about 3600 ng/mL, at least about 3400 ng/mL, at least about 3200 ng/mL, at least about 3000 ng/mL, at least about 2800 ng/mL, at least about 2600 ng/mL, at least about 2400 ng/mL, at least about 2200 ng/mL, and at least about 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro monkey serum is selected from the group consisting of at least about 4000 ng/mL, at least about 3800 ng/mL, at least about 3600 ng/mL, at least about 3400 ng/mL, at least about 3200 ng/mL, at least about 3000 ng/mL, at least about 2800 ng/mL, at least about 2600 ng/mL, at least about 2400 ng/mL, at least about 2200 ng/mL, and at least about 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro dog serum is selected from the group consisting of at least about 4000 ng/mL, at least about 3800 ng/mL, at least about 3600 ng/mL, at least about 3400 ng/mL, at least about 3200 ng/mL, at least about 3000 ng/mL, at least about 2800 ng/mL, at least about 2600 ng/mL, at least about 2400 ng/mL, at least about 2200 ng/mL, and at least about 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro mouse serum is selected from the group consisting of at least about 4000 ng/mL, at least about 3800 ng/mL, at least about 3600 ng/mL, at least about 3400 ng/mL, at least about 3200 ng/mL, at least about 3000 ng/mL, at least about 2800 ng/mL, at least about 2600 ng/mL, at least about 2400 ng/mL, at least about 2200 ng/mL, and at least about 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro rat serum is selected from the group consisting of at least about 4000 ng/mL, at least about 3800 ng/mL, at least about 3600 ng/mL, at least about 3400 ng/mL, at least about 3200 ng/mL, at least about 3000 ng/mL, at least about 2800 ng/mL, at least about 2600 ng/mL, at least about 2400 ng/mL, at least about 2200 ng/mL, and at least about 2000 ng/mL. The foregoing values are relative to non-activated complement at approximately 5000 ng/mL.

In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro human serum is selected from the group consisting of at least 4000 ng/mL, at least 3800 ng/mL, at least 3600 ng/mL, at least 3400 ng/mL, at least 3200 ng/mL, at least 3000 ng/mL, at least 2800 ng/mL, at least 2600 ng/mL, at least 2400 ng/mL, at least 2200 ng/mL, and at least 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro monkey serum is selected from the group consisting of at least 4000 ng/mL, at least 3800 ng/mL, at least 3600 ng/mL, at least 3400 ng/mL, at least 3200 ng/mL, at least 3000 ng/mL, at least 2800 ng/mL, at least 2600 ng/mL, at least 2400 ng/mL, at least 2200 ng/mL, and at least 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro dog serum is selected from the group consisting of at least 4000 ng/mL, at least 3800 ng/mL, at least 3600 ng/mL, at least 3400 ng/mL, at least 3200 ng/mL, at least 3000 ng/mL, at least 2800 ng/mL, at least 2600 ng/mL, at least 2400 ng/mL, at least 2200 ng/mL, and at least 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro mouse serum is selected from the group consisting of at least 4000 ng/mL, at least 3800 ng/mL, at least 3600 ng/mL, at least 3400 ng/mL, at least 3200 ng/mL, at least 3000 ng/mL, at least 2800 ng/mL, at least 2600 ng/mL, at least 2400 ng/mL, at least 2200 ng/mL, and at least 2000 ng/mL. In an embodiment, the invention includes an oligomeric compound comprising a plurality of tc-DNA nucleosides and a plurality of 2'-modified-RNA nucleosides joined by a plurality of internucleoside linkages, wherein the C3 concentration (ng/mL) determined in a complement assay in in vitro rat serum is selected from the group consisting of at least 4000 ng/mL, at least 3800 ng/mL, at least 3600 ng/mL, at least 3400 ng/mL, at least 3200 ng/mL, at least 3000 ng/mL, at least 2800 ng/mL, at least 2600 ng/mL, at least 2400 ng/mL, at least 2200 ng/mL, and at least 2000 ng/mL. The foregoing values are relative to non-activated complement at approximately 5000 ng/mL.

Pharmaceutical Compositions

In an embodiment, an active pharmaceutical ingredient or combination of active pharmaceutical ingredients, such as any of the foregoing oligomeric compounds, is provided as a pharmaceutically acceptable composition, which may include one or more pharmaceutically acceptable excipients.

In some embodiments, the concentration of each of the active pharmaceutical ingredients provided in the pharmaceutical compositions of the invention, such as any of the foregoing oligomeric compounds, is less than about, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is greater than about, for example, 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is in the range from 0.0001% to 50%, 0.001% to 40%, 0.01% to 30%, 0.02% to 29%, 0.03% to 28%, 0.04% to 27%, 0.05% to 26%, 0.06% to 25%, 0.07% to 24%, 0.08% to 23%, 0.09% to 22%, 0.1% to 21%, 0.2% to 20%, 0.3% to 19%, 0.4% to 18%, 0.5% to 17%, 0.6% to 16%, 0.7% to 15%, 0.8% to 14%, 0.9% to 12% or 1% to 10% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical composition.

In some embodiments, the concentration of each of the active pharmaceutical ingredients provided in the pharmaceutical compositions of the invention, such as any of the foregoing oligomeric compounds, is in the range from 0.001% to 10%, 0.01% to 5%, 0.02% to 4.5%, 0.03% to 4%, 0.04% to 3.5%, 0.05% to 3%, 0.06% to 2.5%, 0.07% to 2%, 0.08% to 1.5%, 0.09% to 1%, 0.1% to 0.9% w/w, w/v, or v/v of the pharmaceutical composition.

In some embodiments, the amount of each of the active pharmaceutical ingredients provided in the pharmaceutical compositions of the invention, such as any of the foregoing oligomeric compounds, is equal to or less than about, for example, 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the foregoing oligomeric compounds, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the foregoing oligomeric compounds, is more than about, for example, 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of each of the active pharmaceutical ingredients provided in the pharmaceutical compositions of the invention, such as any of the foregoing oligomeric compounds, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the foregoing oligomeric compounds inhibitors may also be used if appropriate.

In an embodiment, the pharmaceutical compositions of the present invention, such as any of the foregoing oligomeric compounds, are useful in the treatment of neuromuscular or musculoskeletal disease. In some embodiments, the neuromuscular or musculoskeletal disease is Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), or myotonic dystrophy type 1 (DM1 or Steinert disease). In some embodiments, the pharmaceutical compositions of the present invention, such as any of the foregoing oligomeric compounds, cross the blood-brain barrier, thus are useful in treating diseases of the central nervous system, behavioral disorders, psychiatric disorders, and/or behavioral symptoms of diseases. In some embodiments, the disease is a disease of the central nervous system (CNS). In some embodiments, the disease is amyotrophic lateral sclerosis (ALS), Alzheimer's Disease (AD), Parkinson's Disease (PD), Multiple Sclerosis (MS), epilepsy, Creutzfeldt-Jakob, (CJ), Menkes Disease, or Huntington's Disease (HD). In some embodiments, the disease is a disease affecting cerebellar function, including, but not limited to, ataxia. In some embodiments, the disease is a disease affecting amygdala function, including, but not limited to, Urbach-Wiethe Disease. In some embodiments, the disease is a disease affecting hippocampal function, including, but not limited to, memory loss. In some embodiments, the disease to be treated is a psychiatric or behavioral disorder, including, but not limited to, mood disorders, dementia, anxiety, bipolar disorder, schizophrenia, post-traumatic stress disorder (PTSD), attention-deficit hyperactivity disorder (ADHD), and depression disorders. In some embodiments of the present invention, the oligomeric compounds disclosed herein are administered as an active pharmaceutical ingredient in a pharmaceutical composition for use in treating diseases of the central nervous system, behavioral disorders, psychiatric disorders, and/or behavioral symptoms of other diseases, wherein the active is present in a range of from about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of active pharmaceutical ingredient disclosed herein is in a range of from about 4.5 mg/kg to about 50 mg/kg, about 5 mg/kg to about 40 mg/kg, about 6 mg/kg to about 35 mg/kg, about 7 mg/kg to about 30 mg/kg, about 8 mg/kg to about 25 mg/kg, about 9 mg/kg to about 20 mg/kg, about 10 mg/kg to about 19 mg/kg, about 11 mg/kg to about 18 mg/kg, about 12 mg/kg to about 17 mg/kg, about 13 mg/kg to about 16 mg/kg, about 14 mg/kg to about 17 mg/kg, or about 16 mg/kg to about 17 mg/kg. In some embodiments, an effective dosage of an active pharmaceutical ingredient disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, about 3.6 mg/kg, about 4 mg/kg, about 5, mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21, mg/kg, about 22 mg/kg, about 23 mg/kg, about 24 mg/kg, or about 25 mg/kg. In some embodiments, an effective dosage of an active pharmaceutical ingredient disclosed herein is about 50 mg/kg, about 100 mg/kg, about 150 mg/kg, about 200 mg/kg, about 250 mg/kg, or about 300 mg/kg.

In some embodiments, the oligomeric compounds of the present invention may be used to treat diseases of the central nervous system, behavioral disorders, psychiatric disorders, and/or behavioral symptoms of diseases are administered as elsewhere described herein. Doses and dosing regimens as elsewhere described herein for the oligomeric compounds of the present invention are also useful in treating diseases of the central nervous system, behavioral disorders, psychiatric disorders, and/or behavioral symptoms of diseases.

Described below are non-limiting pharmaceutical compositions and methods for preparing the same.

Pharmaceutical Compositions for Oral Administration

In some embodiments, the invention provides a pharmaceutical composition for oral administration containing the active pharmaceutical ingredient or combination of active pharmaceutical ingredients, such as the oligomeric compounds described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or non-aqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

An empirical parameter used to characterize the relative hydrophilicity and hydrophobicity of non-ionic amphiphilic compounds is the hydrophilic-lipophilic balance ("HLB" value). A suitable hydrophilic surfactant may generally have an HLB value of at least 10, while suitable lipophilic surfactants may generally have an HLB value of or less than about 10. Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, .epsilon.-caprolactone and isomers thereof, 6-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, the invention provides a pharmaceutical composition for injection containing an active pharmaceutical ingredient, such as an oligomeric compound and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, the invention provides a pharmaceutical composition for transdermal delivery containing an active pharmaceutical ingredient or combination of active pharmaceutical ingredients, such as the oligomeric compounds described herein, and a pharmaceutical excipient suitable for transdermal delivery.

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252; 4,992,445 and 5,001,139. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the oligomeric compounds described herein. The compositions are administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, orally or nasally, from devices that deliver the formulation in an appropriate manner. Dry powder inhalers may also be used to provide inhaled delivery of the compositions.

Other Pharmaceutical Compositions

Pharmaceutical compositions of the oligomeric compounds described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, et al., eds., *Handbook of Clinical Drug Data*, Tenth Edition, McGraw-Hill, 2002; and Pratt and Taylor, eds., *Principles of Drug Action*, Third Edition, Churchill Livingston, 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), via local delivery by catheter or stent or through inhalation. The active pharmaceutical ingredient or combination of active pharmaceutical ingredients can also be administered intrathecally.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g., PEO-PLLA); polydimethylsiloxane, poly(ethylene-vinylacetate), acrylate-based polymers or copolymers (e.g., polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. The active pharmaceutical ingredient or combination of active pharmaceutical ingredients may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. The active pharmaceutical ingredient or combination of active pharmaceutical ingredients may additionally be administered intravascularly from a balloon used during angioplasty. Extravascular administration of an active pharmaceutical ingredient or combination of active pharmaceutical ingredients via the pericard or via advential application of formulations of the invention may also be performed to decrease restenosis.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include an active pharmaceutical ingredient, such as the oligomeric compounds of the present invention, or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer. The kits described above are for use in the treatment of the diseases and conditions described herein.

In an embodiment, the kits of the present invention are for use in the treatment of a neuromuscular or musculoskeletal disease. In an embodiment, the kits of the present invention are for use in the treatment of a neuromuscular or musculoskeletal disease selected from the group consisting of Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease).

Dosages and Dosing Regimens

The amounts of the pharmaceutical compositions administered using the methods herein, such as the dosages of oligomeric compounds, will be dependent on the human or mammal being treated, the severity of the disorder or condition, the rate of administration, the disposition of the active pharmaceutical ingredients, such as any of the foregoing oligomeric compounds, and the discretion of the prescribing physician. However, in some embodiments, an effective dosage is in the range of about 0.001 to about 500 mg per kg (mg/kg) body weight provided either weekly or biweekly, such as about 1 to about 35 mg/kg/week or about 1 to about 35 mg/kg/2 weeks, in single or divided doses. For a 70 kg human, this would amount to about 0.05 to about 7 g/week or about 0.05 to about 7 g/2 weeks, such as about 0.05 to about 2.5 g/week or about 0.05 to about 2.5 g/2 weeks. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in mg/m² of body surface area.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once a week, once every two weeks, once a month, once every two months, or once every three months. Dosing may be once, twice, three times, four times, five times, six times, or more than six times per day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients in the methods of the invention may continue as long as necessary. In some embodiments, a pharmaceutical composition is administered for more than 1, 2, 3, 4, 5, 6, 7, 14, or 28 days. In some embodiments, a pharmaceutical composition is administered for less than 28, 14, 7, 6, 5, 4, 3, 2, or 1 day. In some embodiments, a pharmaceutical composition is administered chronically on an ongoing basis—e.g., for the treatment of chronic effects. In some embodiments, the administration of a pharmaceutical composition continues for less than about 7 days. In another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 2 g, about 10 mg to about 500 mg, about 20 mg to about 300 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, about 250 mg, about 500 mg, about 1 g, about 1.5 g, about 2 g, about 2.5 g, about 3 g, about 4 g, or about 5 g.

In some embodiments, an effective dosage of an active pharmaceutical ingredient disclosed herein is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of active pharmaceutical ingredient disclosed herein is in a range of from about 4.5 mg/kg to about 50 mg/kg, about 5 mg/kg to about 40 mg/kg, about 6 mg/kg to about 35 mg/kg, about 7 mg/kg to about 30 mg/kg, about 8 mg/kg to about 25 mg/kg, about 9 mg/kg to about 20 mg/kg, about 10 mg/kg to about 19 mg/kg, about 11 mg/kg to about 18 mg/kg, about 12 mg/kg to about 17 mg/kg, about 13 mg/kg to about 16 mg/kg, about 14 mg/kg to about 17 mg/kg, or about 16 mg/kg to about 17 mg/kg. In some embodiments, an effective dosage of an active pharmaceutical ingredient disclosed herein is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, about 3.6 mg/kg, about 4 mg/kg, about 5, mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21, mg/kg, about 22 mg/kg, about 23 mg/kg, about 24 mg/kg, or about 25 mg/kg. In some embodiments, an effective dosage of an active pharmaceutical ingredient disclosed herein is about 50 mg/kg, about 100 mg/kg, about 150 mg/kg, about 200 mg/kg, about 250 mg/kg, or about 300 mg/kg.

In some embodiments, an effective dosage of an active pharmaceutical ingredient disclosed herein is about 1 mg/m$^2$, about 2 mg/m$^2$, about 5 mg/m$^2$, about 10 mg/m$^2$, about 25 mg/m$^2$, about 50 mg/m$^2$, about 100 mg/m$^2$, about 150 mg/m$^2$, about 200 mg/m$^2$, about 250 mg/m$^2$, or about 300 mg/m$^2$.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 1 mg to about 50 mg, about 5 mg to about 45 mg, about 10 mg to about 40 mg, about 15 mg to about 35 mg, about 20 mg to about 30 mg, about 23 mg to about 28 mg, about 50 mg to about 150 mg, about 60 mg to about 140 mg, about 70 mg to about 130 mg, about 80 mg to about 120 mg, about 90 mg to about 110 mg, or about 95 mg to about 105 mg, about 98 mg to about 102 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 207 mg. In some embodiments, an effective dosage of an active pharmaceutical ingredient disclosed herein is about 25 mg, about 50 mg, about 75 mg, about 100 mg, about 125 mg, about 150 mg, about 175 mg, about 200 mg, about 225 mg, or about 250 mg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some embodiments, dosage levels below the lower limit of the aforesaid ranges may be more than adequate, while in other embodiments still larger doses may be employed without causing any harmful side effect—e.g., by dividing such larger doses into several small doses for administration throughout the day.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1—Acute Toxicity of Phosphorothioate Oligonucleotides

Acute toxicity was demonstrated using the SYN51 tc-DNA oligonucleotide sequence shown in FIG. 1 (SEQ ID NO:68), which was synthesized both with all phosphorothioate linkages ("PS") and with all phosphorodiester linkages ("PO"). The likely homodimerization motif of this sequence is also illustrated in FIG. 1.

Polyacrylamide-gel electrophoresis (PAGE) experiments were performed to detect self-multimers. The following chemicals were used: tris(hydroxymethyl)aminomethane (Tris), (TCI A0321); acetic acid (Merck 1.00063); acrylamide/Bis solution, 29:1 (40%, Serva 10680.01); tetramethylethylenediamine (TEMED, Sigma-Aldrich T9281); ammonium persulfate (Sigma-Aldrich 248614); and glycerol (Sigma-Aldrich G9012). Buffer solution A was prepared by dissolving 60 g of Tris in 200 mL of water. The pH is adjusted to 7.4 with glacial acetic acid (about 25-30 mL). The solution is diluted to 500 mL with water and stored at +4° C. Buffer solution B was prepared by diluting 16 mL of buffer solution A to 800 mL with water. Ammonium persulfate 10% (w/v) was prepared by dissolving 100 mg of ammonium persulfate are dissolved in 0.9 mL of water. The preparation of gel was performed by mixing the following solutions in a glass beaker: 9.4 mL acrylamide/bis solution; 15 mL water; 500 µL of buffer solution A; 125 µL of ammonium persulfate 10% (w/v), and 38 µL of TEMED. The test solution was 2 mg/mL in 50% glycerol, and 10 µL was applied (equal to 20 µg of oligonucleotide). The pre-migration settings were 40 min/90 V with buffer solution B. The migration settings were 90 min/90 V or 15 min/90 V plus 45-60 min/120 V with buffer solution B. 5-7 µL of 6×DNA loading dye was also migrated. Detection was performed by placing the gel on a TLC plate and examining under UV light at 254 nm. Afterwards, staining with Stains-All (Sigma-Aldrich, 1-Ethyl-2-[3-(1-ethylnaphtho[1,2-d]thiazolin-2-ylidene)-2-methylpropenyl]naphtho[1,2-d]thiazolium bromide, 3,3'-diethyl-9-methyl-4,5,4',5'-dibenzothiacarbocyanine) according to the manufacturer's protocol was performed.

The results of the gel electrophoresis experiments are shown in FIG. 2. The appearance of multimers is apparent for the SYN51 oligonucleotide of FIG. 1 (SEQ ID NO:68, 5'-PO-AAGATGGCATTTCTA-OH-3') synthesized with all phosphorothioate linkages ("SYN51 PS"), which also occurs for the same oligonucleotide when synthesized using all phosphorodiester linkages ("SYN51 PO"). The other lanes illustrate a control oligonucleotide ("M23D" or "M23D PS") that does not form multimers as predicted from its sequence (but does contain all phosphorothioate linkages), and a SYN51 PS oligonucleotide after storage in 30% ethanol at high temperature to break multimers. The notation "safe" indicates oligonucleotides that were safe in a separate animal study.

In vitro complement activation, measured as % C3 antigen, may be performed using commercially-available enzyme-linked immunosorbent assay (ELISA) kits, using rat, dog, monkey, human, or mouse sera. Examples of kits include Abcam Human Complement C3 ELISA Kit (ab108822), Abcam Mouse Complement C3 ELISA Kit ab157711, and Cusabio Monkey Complement 3 (C3) ELISA Kit (CSB-E16528Mk). Other methods of assessing complement activation known to those of skill the art may be used, such as the methods described in Harboe, et al., *Adv. Drug Deliv. Rev.* 2011, 63, 976-87.

In order to study if the compounds are able to activate complement in vitro, mouse serum samples were incubated with 4 mg/mL of each oligonucleotide at 37° C. for 45 minutes. Mouse C3 complement activation was then analysed by ELISA using PanSpecific C3 reagent followed by SC5b-9 kit. Briefly, mouse C3 protein is converted to human SC5b9 using a C3 converter reagent (Microvue Complement Pan-Specific C3 Reagent Kit, Cat. No. 20261, Quidel Corp., San Diego, Calif., USA) then detected by terminal complex complement SC5b9 ELISA (Microvue Complement SC5b-9 Plus, Cat. No. A020, Quidel Corp., San Diego, Calif., USA). SC5b9 terminal complex complement levels correlate with the status of the terminal complement pathway in the organism. More details of the methods and underlying biology are described in Sefton, et al., *J. Mat. Sci,* 1994, 5, 622-627; Mold, et al., *Clin. Immunol. & Immunopath.,* 1995, 70, 314-320; Rinder, et al., *J. Clin. Invest.,* 1995, 96, 1564-1572; Rollins, et al., *Transplantation* 1995, 60, 1284-1292; Yeh, et al., *J. Immuno.* 1997, 158, 2872-2881. The level of C3 is then expressed as a percentage considering PBS levels at 100% of C3 (no activation).

A mouse toxicology study was also performed using SYN51 synthesized with all phosphorothioate linkages ("SYN51 PS", Syn15-mer HEX51 (+67+81)), SEQ ID NO:68, 5'-AAGATGGCATTTCTA-OH-3') and a second fully phosphorothioate-substituted oligonucleotide (Syn13-mer HEX51 (+68+80)), SEQ ID NO:69, 5'-AGATGGCAT-TTCT-OH-3'). Intravenous injection of 200 mg/kg of the oligonucleotides (approximately 4 mg per mouse) was used. In the group treated with Syn13-mer HEX51 (+68+80), 4/10 animals were found dead on Day 17 or 29 and 6/10 animals were prematurely sacrificed on Day 42 for humane reasons. From Day 15, significant to adverse body weight losses were recorded in almost all animals until death or sacrifice. In biochemistry performed on animals sacrificed prematurely, a slight decrease in chloride concentration and moderate increases in urea and total bilirubin were noted. Marked increases were also seen in total protein and albumin, with a moderate increase in A/G ratio. Enzymes were also affected with a moderate increase in alkaline phosphatase (ALP) activity and marked adverse increases in aspartate aminotransferase (ASAT) and alanine aminotransferase (ALAT) activities. In the group treated with SYN51 PS (Syn15-mer HEX51 (+67+81)), 4/11 animals were found dead on Days 1, 16 or 29 and 3/11 animals were prematurely sacrificed on Day 29 or 44 for humane reasons. In both groups, severe and transient clinical signs were recorded in these animals after each intravenous administration and mainly consisted in ventral or lateral recumbency, hypoactivity, half-closed eyes, and dyspnea. Local reactions were also recorded and were attributed to the test item injection. Deaths in these groups were considered to be related to the oligomeric compounds tested. The acute deaths observed within a day of the intravenous injection with Syn13-mer HEX51 (+68+80) (3/10 females) and SYN51 PS (Syn15-mer HEX51 (+67+81)) (7/11 females) were most likely related to the shock associated with the marked increases in cytokines and/or to the complement activation observed on the days of injection. Microscopic findings were similar to those seen in other animals at terminal sacrifice and could not explain these acute deaths. The moribund condition that led to premature sacrifice on Day 42 of the surviving females treated with Syn13-mer HEX51 (+68+80) was considered to be related to renal lesions. These animals also showed pronounced liver lesions that may have contributed to their poor health status. In surviving animals, similar clinical signs than those described above were observed in animals treated with SYN51 PS (Syn15-mer HEX51 (+67+81)) after each intravenous administration. These clinical signs were considered to be adverse. A control group of mice injected with phosphate-buffered saline showed no adverse clinical signs.

Figure 3:
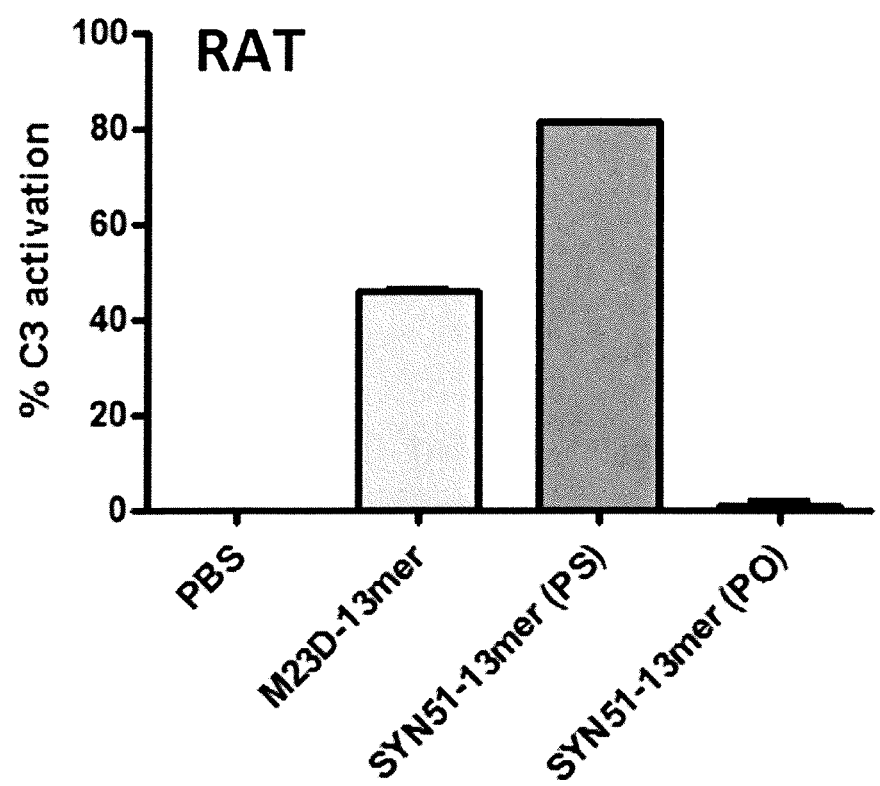
FIG. 3 illustrates the results of a complement activation assay (rat) for SYN51 and M23D oligonucleotides. Phosphate-buffered saline (PBS) is used as a control.
Figure 4:
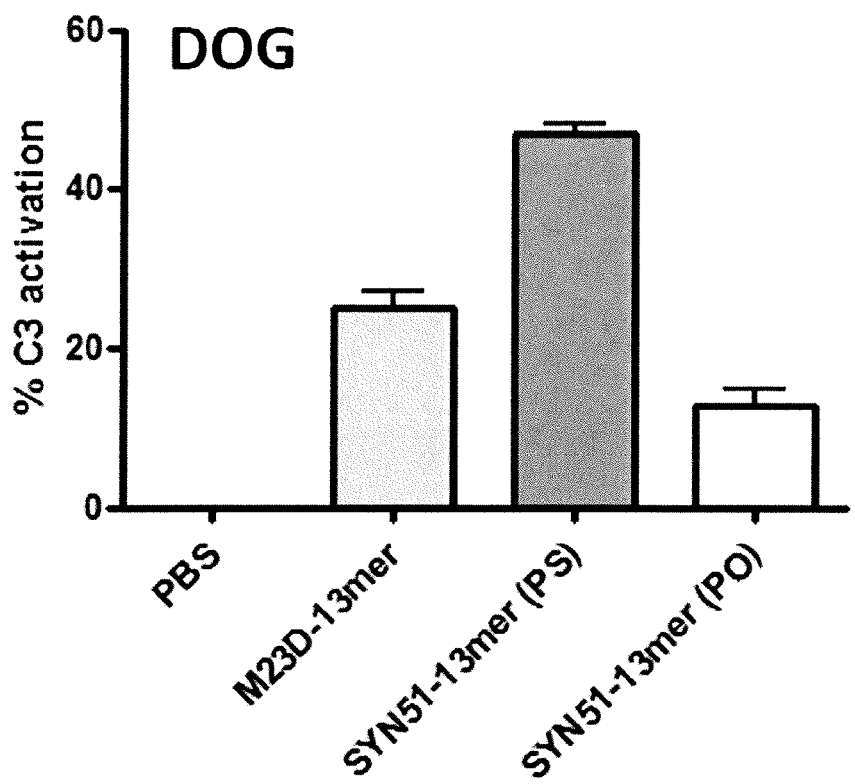
FIG. 4 illustrates the results of a complement activation assay (dog) for SYN51 and M23D oligonucleotides. PBS is used as a control.

The results of the % C3 complement activation assay are shown in FIG. 3 and FIG. 4, which show the results of the assay in rat serum and dog serum, respectively. The strongest activation is observed for SYN51 PS, consistent with the death of animals observed in the tox study described above using this oligonucleotide. Much milder activation is observed for the SYN51 PO and the fully PS M23D oligonucleotides, which correlated with the lack of toxicity in the animal study. The results demonstrate that particular oligonucleotides have increased toxicity both because of the inclusion of PS groups and because of the tendency to form multimers. This creates a significant problem for the design of useful oligonucleotides for exon-skipping and exon-inclusion diseases based on tc-DNA because of the need for phosphorothioate linkages.

Figure 5:
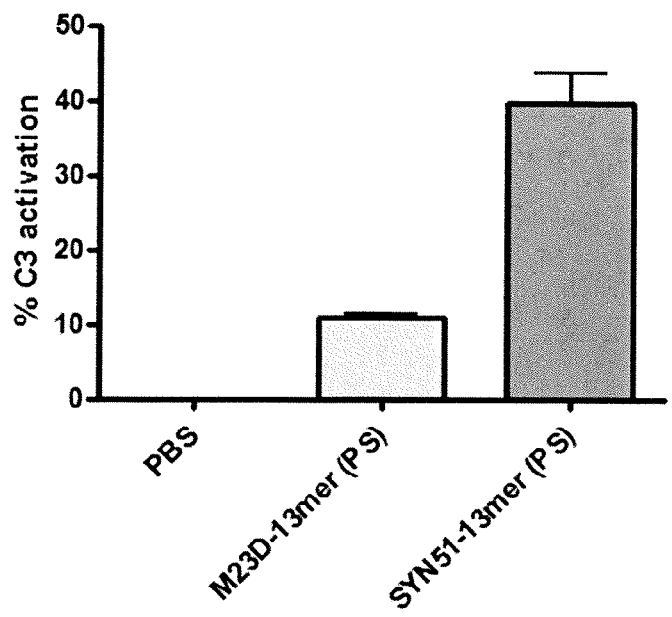
FIG. 5 illustrates the results of a complement activation assay for SYN51 PS and M23D PS oligonucleotides. PBS is used as a control.
Figure 6:
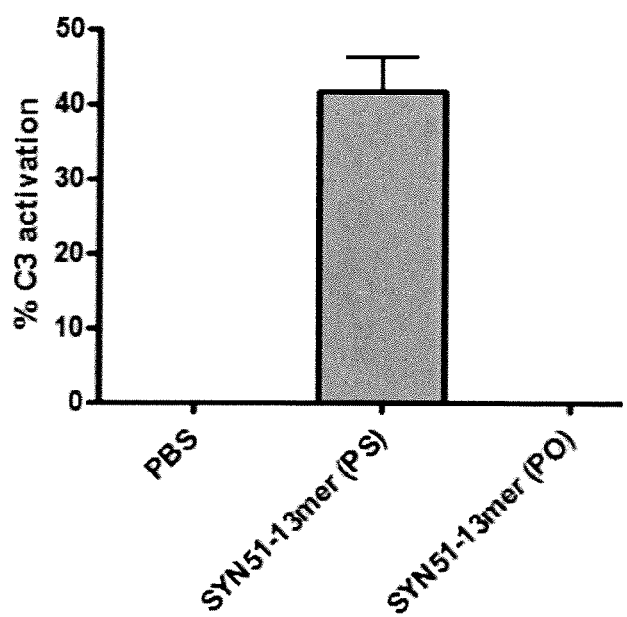
FIG. 6 illustrates the results of a complement activation assay for SYN51 PS (fully phophorothioate, previously shown in FIG. 5) and SYN51 PO (fully phosphorodiester) oligonucleotides. PBS is used as a control.

The difficulties with toxicity of SYN51 PS, and activation of the complement by PS internucleoside linkages through the alternative pathway, are further illustrated by a complement activation assay in mouse serum, where a decrease in total C3 (which is split into C3a and C3b upon activation) 1 hour after i.v. injection of PBS control or M23D PS, SYN51 PS, or SYN51 PO at a dose of 200 mg/kg. Results are shown in FIG. 5 and FIG. 6. Acute toxicity and complement activation is consistently observed with SYN51 PS but not with the same tc-DNA sequence with full PO internucleoside linkages. M23D PS was never observed to be toxic in animals but still induces moderate activation of the complement, highlighting the challenges in avoiding toxicity with oligonucleotides developed for human therapy.

Example 2—Identification of Multimers

A study was performed to explore multimer formation of tc-DNA oligonucleotides and identification of additional bands in gel electrophoresis experiments. As noted previously, it was observed that tc-DNA oligonucleotides with acute toxicity show an additional band in polyacrylamide gel electrophoresis experiments. It was proposed that this rather sharp band is a multimer of the oligonucleotide (e.g., duplex, trimer, or larger aggregate). The aim of this study is to identify the structure of this additional band. All oligonucleotides in this study are full tc-DNA and utilize full phosphorothioate (PS) internucleoside linkages (except for the PO group at the 5'-end).

Figure 7:
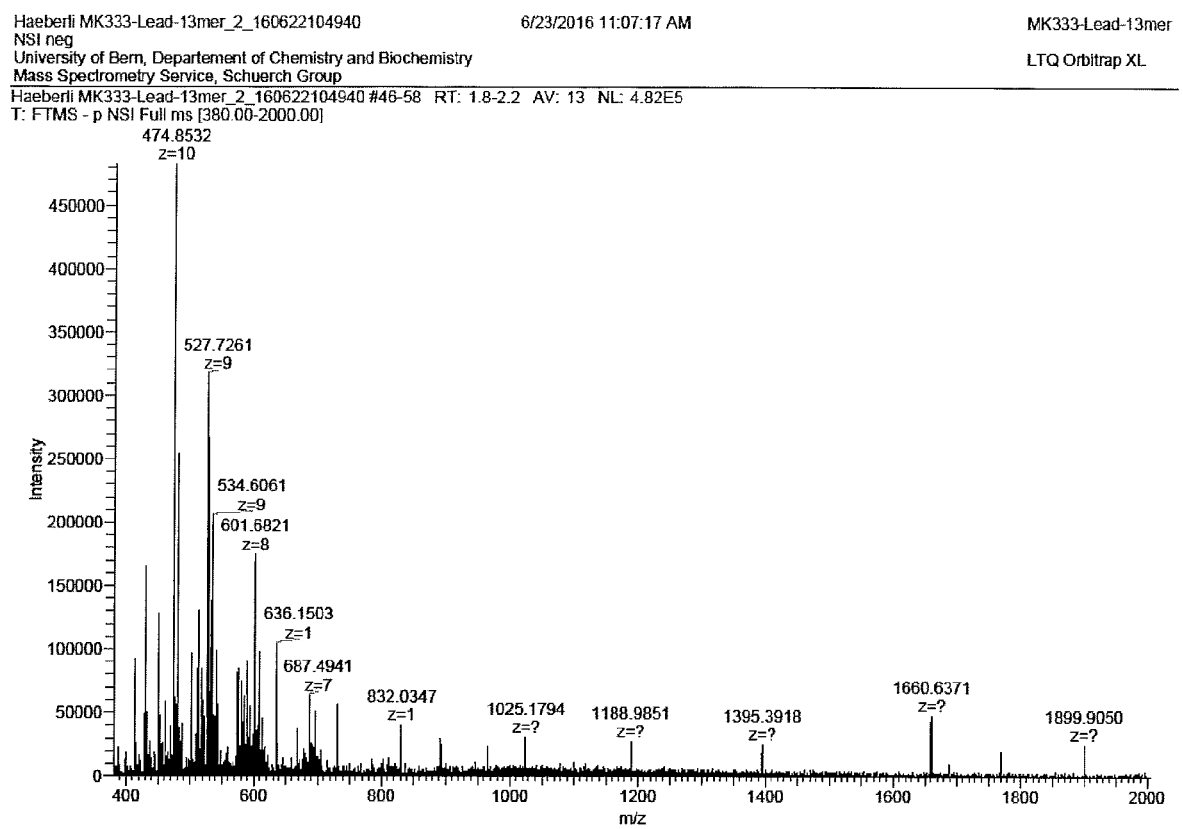
FIG. 7 illustrates Orbitrap MS results for oligonucleotide SY-0206 (batch MK333). No multimers were detected.
Figure 8:
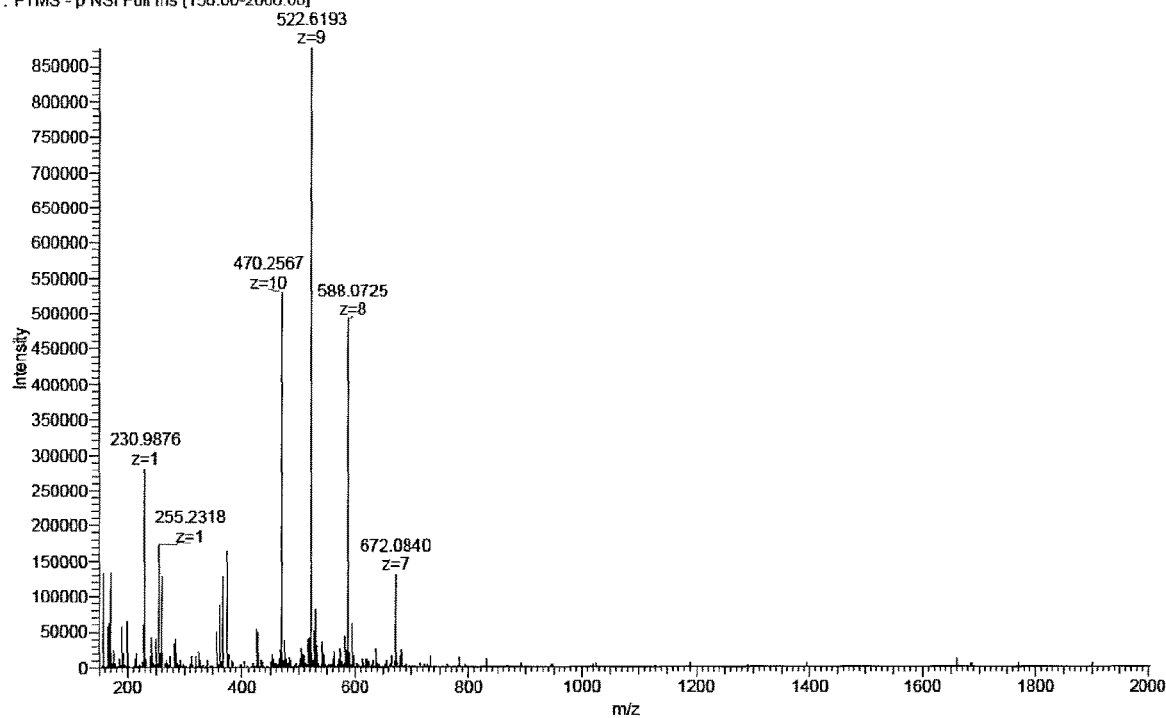
FIG. 8 illustrates Orbitrap MS results for oligonucleotide SY-0210 (batch MK371). No multimers were detected.

The following oligonucleotides were measured by mass spectrometric (MS) analysis using an Orbitrap (ThermoFisher) instrument: SY-0206 (batch MK333, SYN 13-mer, purity 82%, toxic, SEQ ID NO:70); and SY-0210 (batch MK371, M23D 13-mer, purity 76%, non-toxic, SEQ ID NO:71). 14 µM solutions were prepared in water, diluted with methanol/water, and immediately injected. Mass spectra are shown in FIG. 7 and FIG. 8. The results confirm the mass of both oligonucleotides. No signals corresponding to higher order structures (e.g., multimers) were detected by Orbitrap MS, indicating that multimers have dissociated, which rules out the formation of new covalent structures as a source of the additional band in polyacrylamide gel electrophoresis experiments.

Extraction of bands from the polyacrylamide gel was then performed. Four wells were loaded with 40 µg of SY-0206 each (batch MK568, SEQ ID NO:70, SYN 13-mer, purity about 70%, loaded with 20% glycerol, no annealing). The lower band ("monomer band") and upper band ("multimer band") were extracted in 0.05 M ammonium acetate buffer for 48 hours at room temperature. The extracts from above were measured by ion pairing reversed phase high-performance liquid chromatography with time of flight mass spectrometry (HPLC-TOF-MS) using two different methods as described in the following two paragraphs.

In the first method, a C18 column with a particle size of 1.7 µm was used. The column temperature was set to 75° C. Mobile phase A was 400 mM hexafluoroisopropanol (HFIP) and 15 mM triethylamine, and mobile phase B was methanol. A gradient of 18 to 28% methanol was applied, although other gradients can be employed. The flow rate was set to 0.2 mL/min. The oligonucleotides were detected using a UV detector set at 260 nm and a time-of-flight mass spectrometer. The monomer band had a purity of 82%. About 10% of shortmers were detected. No additional signals in the chromatogram or MS spectra were observed (e.g., no multimers). The multimer band had a purity of 56%. About 34% of shortmers were detected. No new signals in the chromatogram or MS spectra were observed (e.g., no multimers).

Figure 9:
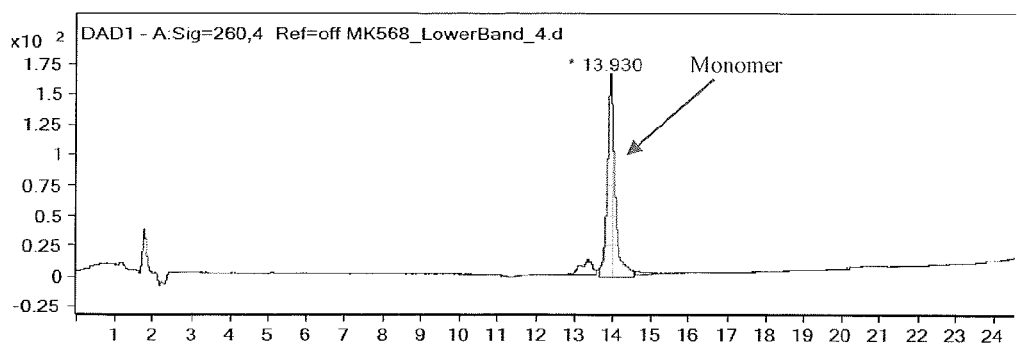
FIG. 9 illustrates a high-performance liquid chromatography (HPLC) chromatogram of the extracted monomer band (column temperature 30° C.).
Figure 10:
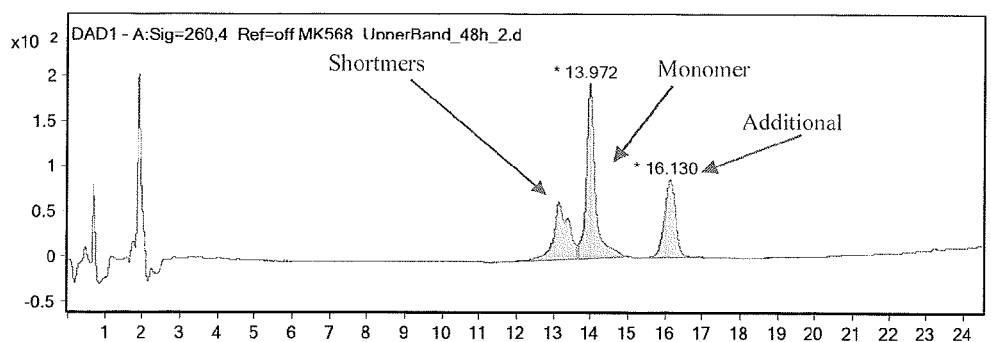
FIG. 10 illustrates a HPLC chromatogram of the extracted multimer band (column temperature 30° C.).

In the second method, a lower column temperature (30° C.) and steeper gradient (15 to 90% of MeOH) were used. The monomer band yielded comparable results as with the first method (FIG. 9). In the HPLC chromatogram of the multimer band, an additional signal with relative retention time of 1.15 was detected (FIG. 10). In the MS spectrum, it was shown that this signal consists of the monomer, no multimers were detected. The fact that the ratio of peaks changed with time, temperature, and sample handling suggests that reversed-phase HPLC-MS is not the method of choice for analysis or structure determination of the multimers.

With both MS and HPLC methods unable to detect the origin of the additional band in polyacrylamide gel electrophoresis experiments, further study using gel electrophoresis was performed. The following isolated gel extracts were loaded on polyacrylamide gel, in order to evaluate the stability of isolated bands after extraction (FIG. 11):

Extracted monomer (5 µg, see above)
Extracted multimer (1.8 µg, see above)
SY-0206 (batch MK333); SYN 13-mer (AGA TGG CAT TTC T, 5 µg, toxic) (SEQ ID NO:70)
SY-0206 (batch MK568); SYN 13-mer (AGA TGG CAT TTC T, 5 µg, toxic) (SEQ ID NO:70)
SY-0210 (batch MK371); M23D 13-mer (CCT CGG CTT ACC T, 5 µg, non-toxic) (SEQ ID NO:71)

Figure 12:
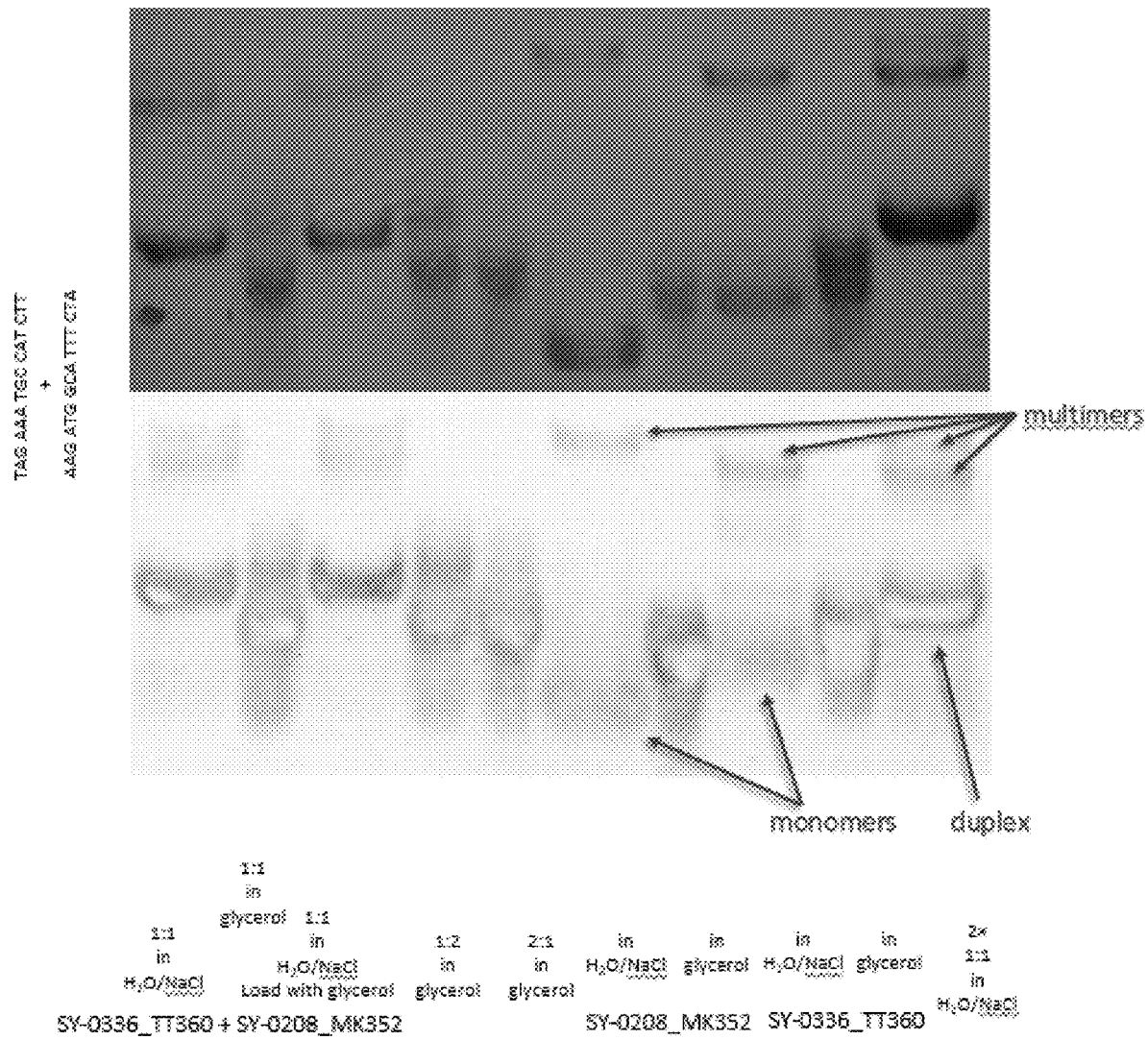
FIG. 12 illustrates non-denaturing PAGE of single stranded SY-0208 and SY-0336 and duplexes thereof (visualization with UV at 258 nm and StainsAll).

The mobility of the tc-DNA duplex, composed of two fully complementary tc-DNA sequences, is very similar to the parent monomer. The multimer band has substantially lower mobility than this duplex (FIG. 12):

SY-0208 (batch MK352); SYN 15-mer (AAG ATG GCA TTT CTA) (SEQ ID NO:72)
SY-0336 (batch TT360); complement to SYN 13-mer (TAG AAA TGC CAT CTT) (SEQ ID NO:73)

Figure 13:
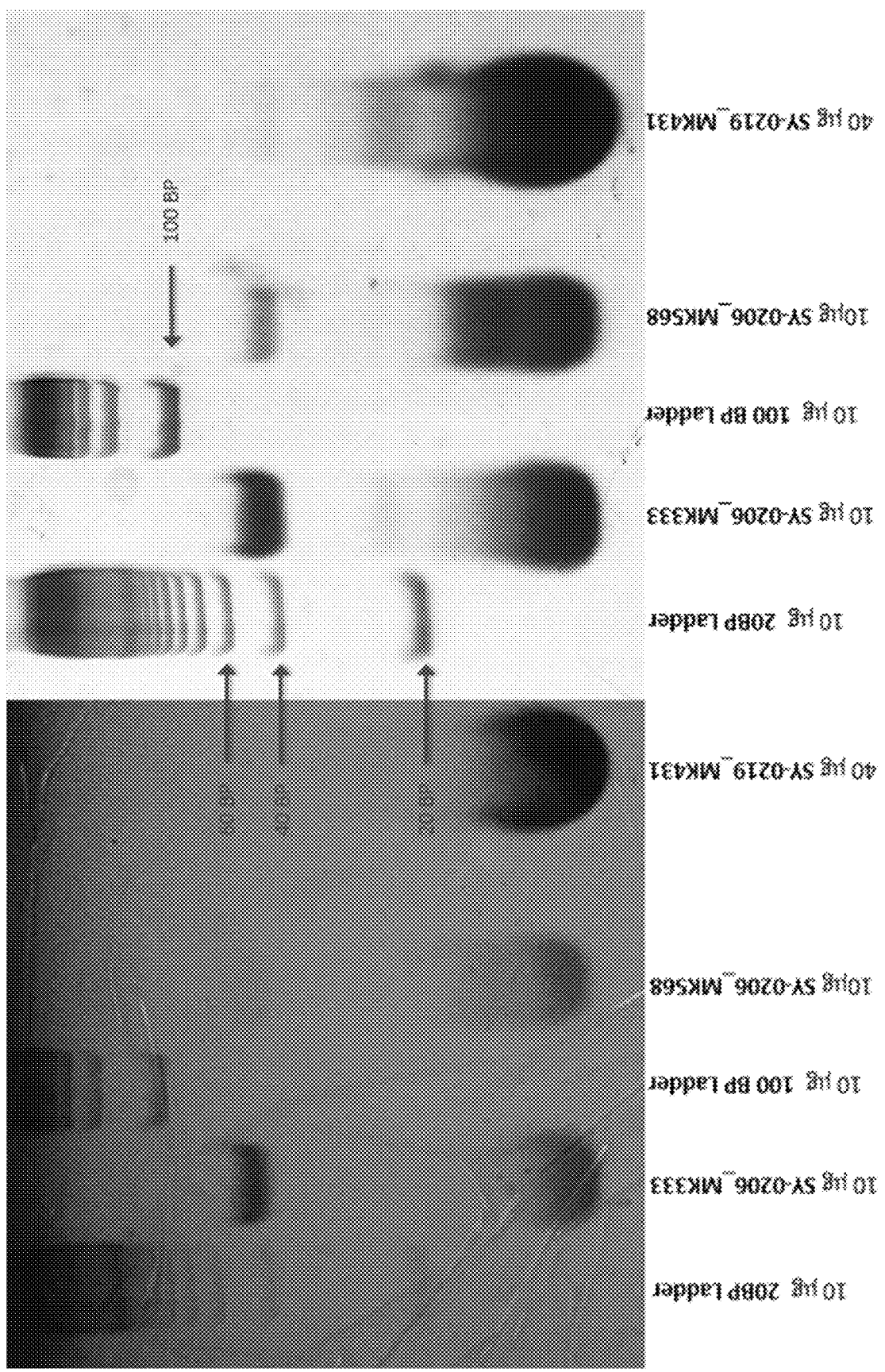
FIG. 13 illustrates tc-DNA versus DNA ladder (visualization with UV at 258 nm and StainsAll).

The approximate size of the "upper band" has been evaluated using a DNA ladder as a size marker using the following samples (FIG. 13):

PCR Low Ladder Set, Sigma D7808, 20/100 bp ladder
SY-0206 (batch MK333); SYN 13-mer (AGA TGG CAT TTC T, 10 µg, toxic) (SEQ ID NO:70) SYN 15-mer
SY-0206 (batch MK568); SYN 13-mer (AGA TGG CAT TTC T, 10 µg, toxic) (SEQ ID NO:70)
SY-0219 (batch MK431); 15-mer HEX51 (+97;+111) (CTG CCA GAG CAG GTA, 40 µg, slightly toxic) (SEQ ID NO:74)

Figure 11:
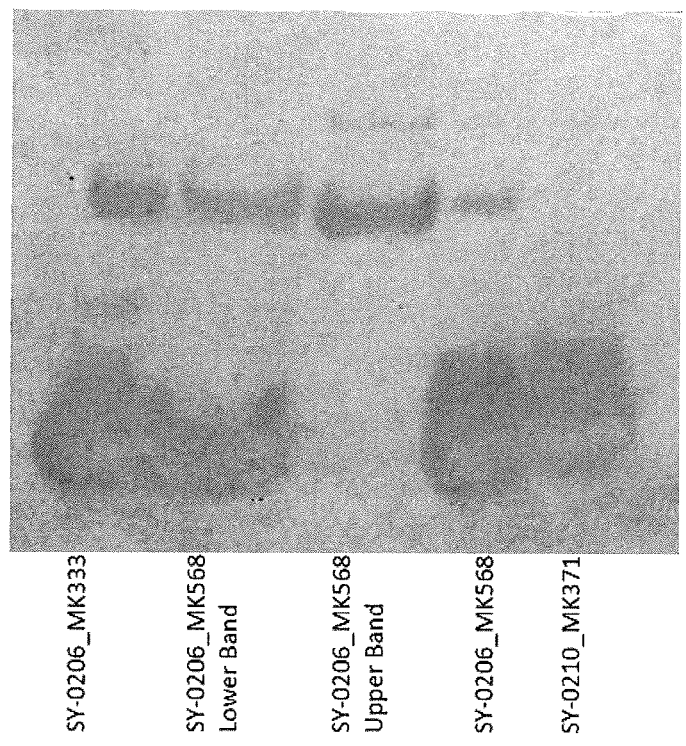
FIG. 11 illustrates non-denaturing polyacrylamide gel electrophoresis (PAGE) of extracted bands of SY-0206 (visualization with StainsAll).

The results of the foregoing experiments are summarized as follows. After isolation, the extracted monomer forms two bands identical to parent oligonucleotide (monomer and multimer). After isolation, the extracted multimer forms rather a stable structure, as no monomer re-forms. Moreover, an additional band that migrates even less than the other bands appears (FIG. 11). Based on the mobility of tc-DNA duplex, the "upper band" is most likely a larger structure than a dimer of parent oligonucleotide, i.e., a multimer. The structure of this multimer band for oligonucleotide SY-0206 appears to be in the range of about 40 base pairs (6-mer) according to the DNA ladder experiment In conclusion, the multimer band consists most likely of monomers, which dissociate during the MS measurement (e.g., at higher temperature on the HPLC column or in the MS source). Consequently, formation of a new oligonucleotide can be excluded (e.g., a covalently bound dimer). It appears that impurities, especially shortmers, are accumulated in the multimer band. The multimer band is most likely not a simple duplex, but rather a 5-mer to 10-mer. The exact structure of the multimer and the mechanism by which oligonucleotides form multimers with a single, rather well defined band as observed by PAGE is under investigation. If the acute toxicity observed in mice results from alternative complement activation pathway, formation of multimers of tc-DNA oligonucleotides fits well with the published mechanism of complement activation (Henry, et al., *J. Pharmacol. Exp. Ther.* 1997, 281, 810-816). The mechanism involves binding of Factor H (through polyanion binding sites); therefore, increasing the net charge of oligonucleotide by formation of multimers should result in improved binding to Factor H and consequent triggering of the complement activation cascade. Moreover, Factor H has been identified as one of the significant PS tc-DNA binding proteins based on results from biotinylated PS tc-DNA oligonucleotides.

A size exclusion chromatography (SEC) method was developed and may be used for quantification of monomer and multimer levels and ratios. The SEC method uses a TSKgel column (G3000PWXL, 300×7.8 mm, Tosoh Bioscience, No 08021). The sample is dissolved at 5.0 mg/mL in water and prepared immediately before use, and an injection volume of 0.1 µL is used. The mobile phase is prepared by dissolving 11.7 g of sodium dihydrogen phosphate dihydrate (Sigma 71505) in about 450 mL of water, adjusting the pH to 7.0 with 4 N sodium hydroxide, and diluting the solution to 500 mL with water. The column temperature is 20° C. and the flow is 0.50 mL/minute. The maximum column pressure is 40 bars. UV detection is used with a wavelength of 260 nm. Signals in the chromatogram are normalized and peaks are separated with a valley-drop line.

Example 3—Synthesis and Characterization of Oligomeric Compounds

As described in the previous examples, a correlation exists between the toxicity of PS tc-DNA oligonucleotides and their ability to form multimers. Safe sequences (e.g., M23D) do not form self-multimers as identified by non-denaturing PAGE and SEC. It has been shown (e.g., in Example 1) that the disruption of a multimer structures leads to suppression of toxicity of an oligonucleotide that is otherwise toxic in its multimeric form. Other methods of disrupting self-multimer structures, including self-dimers, are known in the art (see, e.g., WO 2008/114262) but are not adequate at least for suppressing self-multimer formation and toxicity in antisense oligonucleotides comprising both tc-DNA and phosphorothioate linkages designed for use in treating exon-skipping diseases such as DMD. The novel approaches described herein to suppress self-multimer formation (as in the toxic SYN51) employ new chemistry introduced in the backbone in order to disrupt the highly pre-organized structure of tc-DNA.

Sequence selection was performed using the following approach. The structure of the most stable anti-parallel self-dimer contains two blocks of three consecutive Watson-Crick base pairs separated by a single G-G mismatch. Moreover, when taking into account possible G-T wobble base pairs, the sequence can be considered to form two stretches of five consecutive base-pairs separated by a single G-G mismatch.

```
    5'    AAGATGGCATTTCTA   | = Watson-Crick
          |:||| |||:|
    3'    ATCTTTACGGTAGAA   : = Wobble
```

The backbone modification approach involves modifying the three-base pair stretch in the putative structure above via introduction of one to four 2'-OMe-RNA nucleosides into original tc-DNA sequence. Such a substitution provides at least 30 possible sequences (Table 1). For illustrative purposes, twelve of these sequences have been selected below for evaluation of the approach:

4× single base substitution—one for each base
3× two and three base substitution—one consecutive and two separated bases (within one or two base pair stretches)
2× four base substitution—located in the region of the 3'- or 5'-end This selection yielded the non-limiting sequences shown in Table 3.

TABLE 3

Non-limiting oligonucleotide sequences designed by the approach described in this example.

| Name | Identifier | Sequence (A, G, C, T = tc-DNA; a, g, c, u = 2'-modified-RNA) |
|---|---|---|
| SY-0329 | SEQ ID NO: 31 | AAG aTG GCA TTT CTA |
| SY-0330 | SEQ ID NO: 32 | AAG AuG GCA TTT CTA |
| SY-0331 | SEQ ID NO: 33 | AAG ATg GCA TTT CTA |
| SY-0332 | SEQ ID NO: 34 | AAG ATG GcA TTT CTA |
| SY-0333 | SEQ ID NO: 35 | AAG auG GCA TTT CTA |
| SY-0334 | SEQ ID NO: 36 | AAG aTg GCA TTT CTA |
| SY-0335 | SEQ ID NO: 37 | AAG aTG GcA TTT CTA |
| SY-0337 | SEQ ID NO: 38 | AAG aug GCA TTT CTA |
| SY-0338 | SEQ ID NO: 39 | AAG auG GcA TTT CTA |

TABLE 3-continued

Non-limiting oligonucleotide sequences designed by the approach described in this example.

| Name | Identifier | Sequence (A, G, C, T = tc-DNA; a, g, c, u = 2'-modified-RNA) |
|---|---|---|
| SY-0339 | SEQ ID NO: 40 | AAG AuG GcA uTT CTA |
| SY-0340 | SEQ ID NO: 41 | AaG aug GCA TTT CTA |
| SY-0341 | SEQ ID NO: 42 | AAG ATG Gca uTu CTA |

In addition to sequence selection as described above, further design of oligonucleotides is necessary to address toxicity. As described above, the acute toxicity triggered upon bolus administration of some tc-DNA oligonucleotides with phosphorothioate linkages correlates with the propensity of those sequences to form multimers. The mechanism of complement activation by oligonucleotides with phosphorothioate linkages is known to involve binding of polyanionic oligonucleotides to factor H, which acts as a brake on the alternative cascade of complement. Proteomic methods were used determine which human serum proteins bind to a non-toxic oligonucleotide (for example M23D) and compared the profile to the human serum proteins that bind to a "toxic" oligonucleotide (for example SYN51-PS). Many of the proteins identified are part of the complement system. The overall identities of the binding proteins are similar between the two oligonucleotides. This provides evidence that toxicity is due to enhanced protein binding in the presence of high PS ratios compared to low PS ratios, and that breaking the multimer into its parent monomeric structures may result in reduced toxicity.

Although the introduction of new chemistry (e.g., 2'-OMe-RNA) into a full tc-DNA backbone at the position of self-multimerization can break multimers, such an alternation of tc-DNA backbone also lowers the affinity towards target RNA. Reducing the amount of sulfur in the backbone can also reduce the toxicity of tc-DNA oligonucleotides, but also reduces affinity towards proteins, which is necessary for protecting the oligonucleotides against renal filtration and is likely needed at cellular level for effective shuttling of the oligonucleotide into the nucleus.

Oligonucleotide synthesis was performed as follows. Oligonucleotides were synthesized either on a 50 µmol scale using an OP-10 synthesizer or on a 1 µmol scale using an Expedite parallel synthesizer. All synthesized sequences were deprotected and purified using standard procedures, as described in Renneberg, et al., *J. Am. Chem. Soc.* 2002, 124, 5993-6002. Desired final purity is >75% of FLP and is determined using the ion-pairing reversed phase high performance liquid chromatography method described in Example 2 coupled with mass spectrometry. Other suitable methods may be used, including those described in *Handbook of Analysis of Oligonucleotides and Related Products*, CRC Press, 2011.

Evaluation of toxicity, efficacy and biodistribution in vivo was performed as follows. Mice were injected IV (retro-orbital) with 200 mg/kg of tc-DNA per week (bolus injection of ~100 µL for a 20 g mouse) for 4 weeks and analyzed 2 weeks after the last injection. Mice are carefully evaluated and videotaped following injection to monitor and assess for clinical signs of toxicity. Serum is collected 1 hour after the injection for complement activation analysis. 2 weeks after the last injection (4 injections in total), serum is collected for biochemistry analysis (creatine kinase (CK), alanine aminotransferase (ALT), aspartate aminotransferase (AST), bilirubin, urea, creatinine, and albumin). Various muscles and tissues (TA, Gas, Quad, Tri, Bi, Dia, heart and brain) are analyzed for exon 51 skipping (RNA extraction, Nested RT-PCR, qRT-PCR) and analyzed for biodistribution (mass spectrometry). Liver and kidney is harvested for biodistribution only.

The design goals for the compounds are: (1) well tolerated after bolus intravenous injection at high doses and (2) trigger sufficient exon 51 skipping. Sufficient exon 51 skipping may be effected by an oligonucleotide that: (1) has high affinity towards target pre-mRNA; (2) is sufficiently stabilized against renal filtration; (3) is stable against degradation; and (4) is taken up into target cells.

Table 4 lists oligonucleotides that combine the design elements of this example. Table 5 also includes additional examples for use as probe molecules (labeled with 5'-biotin) or as comparators.

TABLE 4

Non-limiting oligonucleotide sequences designed by the approach described in this example. A "*" represents a PS (phosphorothioate) linkage; "A", "G", "C", and "T" each represent tc-DNA; and "a", "g", "c", and "u" each represent 2'-O-methyl RNA. All "C" are 5-methylcytosines, and all "c" are cytosines.

| Name and Identifier | Description | Sequence |
|---|---|---|
| SY-0340 SEQ ID NO: 41 | Hex51 (+67; +81) 2-OMe 11 | A*a*G* a*u*g* G*C*A* T*T*T* C*T*A |
| SY-0371 SEQ ID NO: 43 | Hex51 (+67; +81) 2-OMe 13 (6Sb5) | A*a*G* a*u*g* GCA TTT CTA |
| SY-0372 SEQ ID NO: 44 | Hex51 (+67; +81) 2-OMe 14 (6Sb3) | AAG ATG GCA* u*T*u* C*u*A |
| SY-0373 SEQ ID NO: 45 | Hex51 (+67; +81) 2-OMe 15 (5Sb3) | G AAG ATG GCA* u*u*u* c*T |
| SY-0374 SEQ ID NO: 46 | Hex51 (+66; +83) 2-OMe 16 (6Sb3) | AGG AAG ATG GCA* u*u*u* c*u*A |
| SY-0375 SEQ ID NO: 75 | Hex51 (+66; +83) 2-OMe 17 | A*G*G* A*A*G* A*T*G* G*C*A* u*u*u* c*u*A |
| SY-0376 SEQ ID NO: 76 | Biot-Hex51 (+67; +81) 2-OMe 11 | biotin-A*a*G* a*u*g* G*C*A* T*T*T* C*T*A |
| SY-0377 SEQ ID NO: 77 | Biot-Hex51 (+67; +81) 2-OMe 13 (6Sb5) | biotin-A*a*G* a*u*g* GCA TTT CTA |
| SY-0378 SEQ ID NO: 78 | Biot-Hex51 (+67; +81) 2-OMe 14 (6Sb3) | biotin-AAG ATG GCA* u*T*u* C*u*A |
| SY-0379 SEQ ID NO: 79 | Biot-Hex51 (+67; +81) 2-OMe 15 (5Sb3) | biotin-G AAG ATG GCA* u*u*u* c*T |
| SY-0380 SEQ ID NO: 80 | Biot-Hex51 (+66; +83) 2-OMe 16 (6Sb3) | biotin-AGG AAG ATG GCA* u*u*u* c*u*A |

TABLE 4-continued

Non-limiting oligonucleotide sequences designed by the approach described in this example. A "*" represents a PS (phosphorothioate) linkage; "A", "G", "C", and "T" each represent tc-DNA; and "a", "g", "c", and "u" each represent 2'-O-methyl RNA. All "C" are 5-methylcytosines, and all "c" are cytosines.

| Name and Identifier | Description | Sequence |
|---|---|---|
| SY-0381 SEQ ID NO: 81 | Biot-Hex51 (+66; +83) 2-OMe 17 | biotin-A*G*G* A*A*G* A*T*G* G*C*A* u*u*u* c*u*A |
| SY-0382 SEQ ID NO: 82 | M23D-15m (2OMe 5Sb3) | AAC CTC GGC T*u*a* c*c*T |
| SY-0383 SEQ ID NO: 83 | M23D-15m (2OMe 4Sb3) | AAC CTC GGC TT*a* c*c*T |
| SY-0384 SEQ ID NO: 84 | M23D-15m (2OMe 3Sb3) | AAC CTC GGC TTA* c*c*T |
| SY-0385 SEQ ID NO: 85 | Biot-M23D-15m (2OMe 5Sb3) | biotin-AAC CTC GGC T*u*a* c*c*T |
| SY-0386 SEQ ID NO: 86 | Biot-M23D-15m (2OMe 4Sb3) | biotin-AAC CTC GGC TT*a* c*c*T |
| SY-0387 SEQ ID NO: 87 | Biot-M23D-15m (2OMe 3Sb3) | biotin-AAC CTC GGC TTA* c*c*T |

Figure 14:
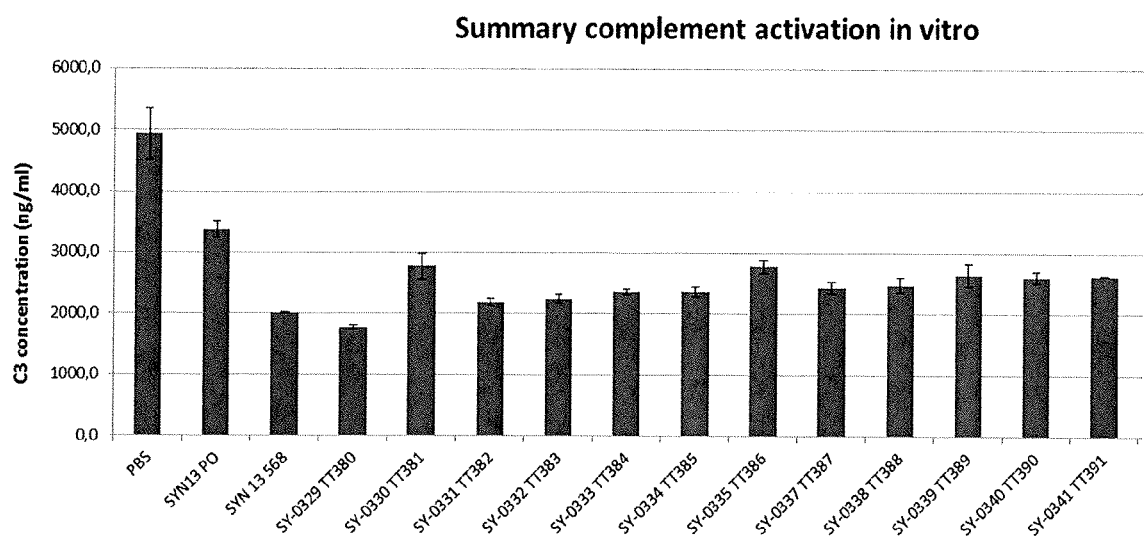
FIG. 14 illustrates the results of a complement activation assay for oligonucleotides of the present invention.
Figure 15:
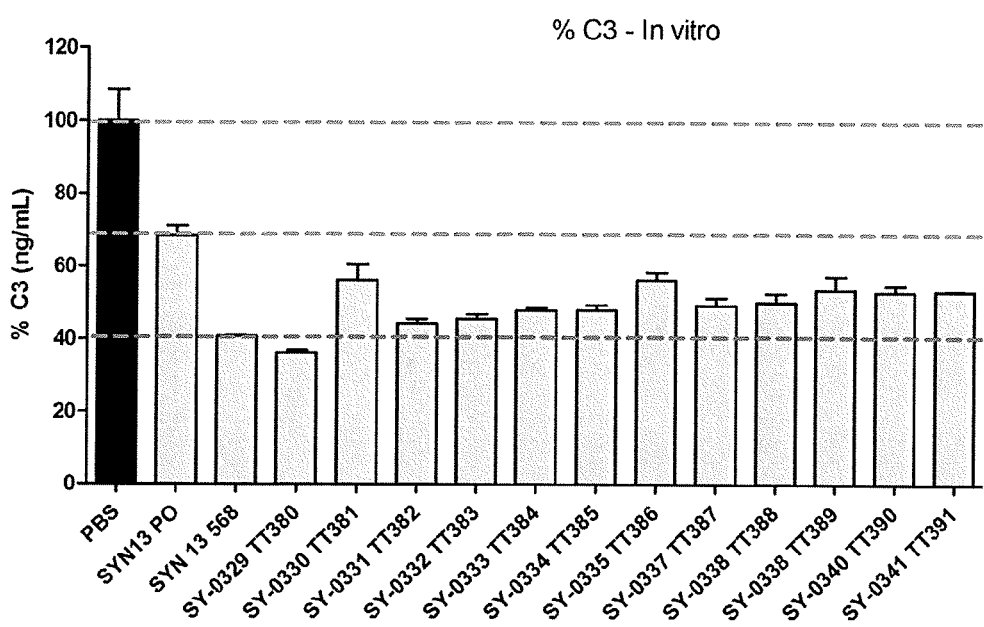
FIG. 15 illustrates the results of a complement activation assay for oligonucleotides of the present invention.
Figure 16:
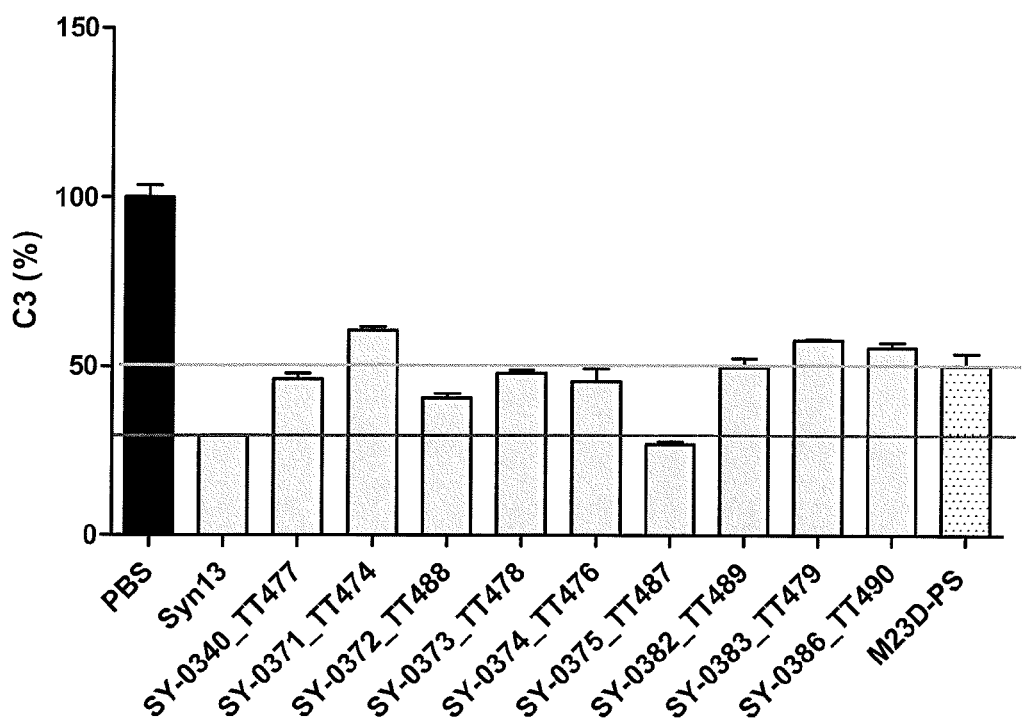
FIG. 16 illustrates the results of a complement activation assay for oligonucleotides of the present invention.
Figure 17:
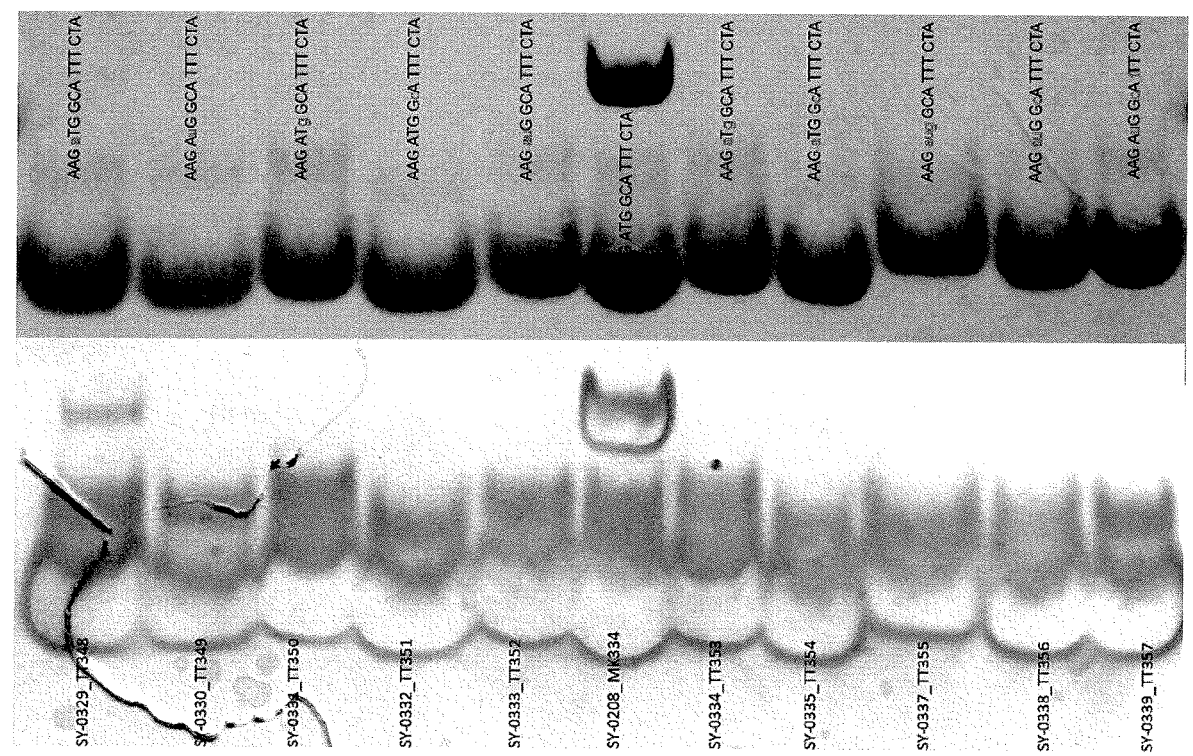
FIG. 17 illustrates the results of gel electrophoresis analysis for oligonucleotides of the present invention.
Figure 18:
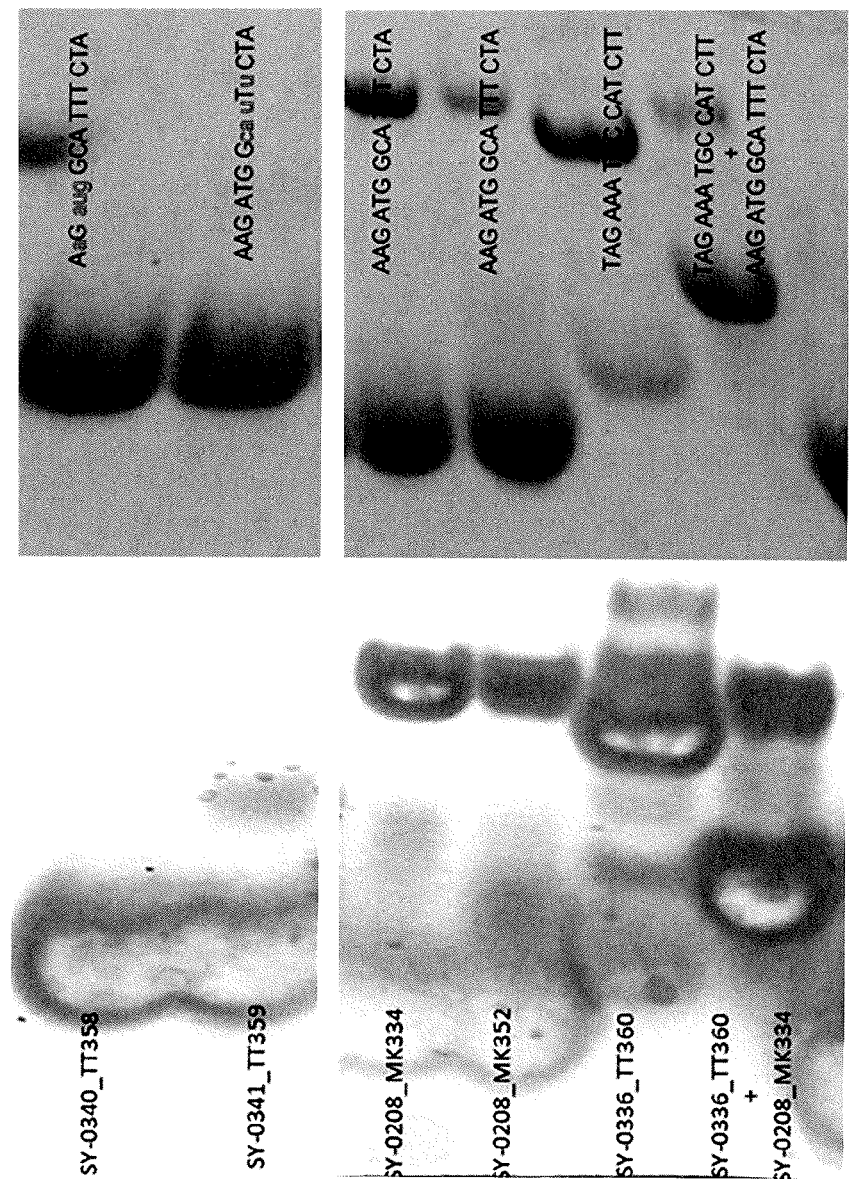
FIG. 18 illustrates the results of gel electrophoresis analysis for oligonucleotides of the present invention.
Figure 19:
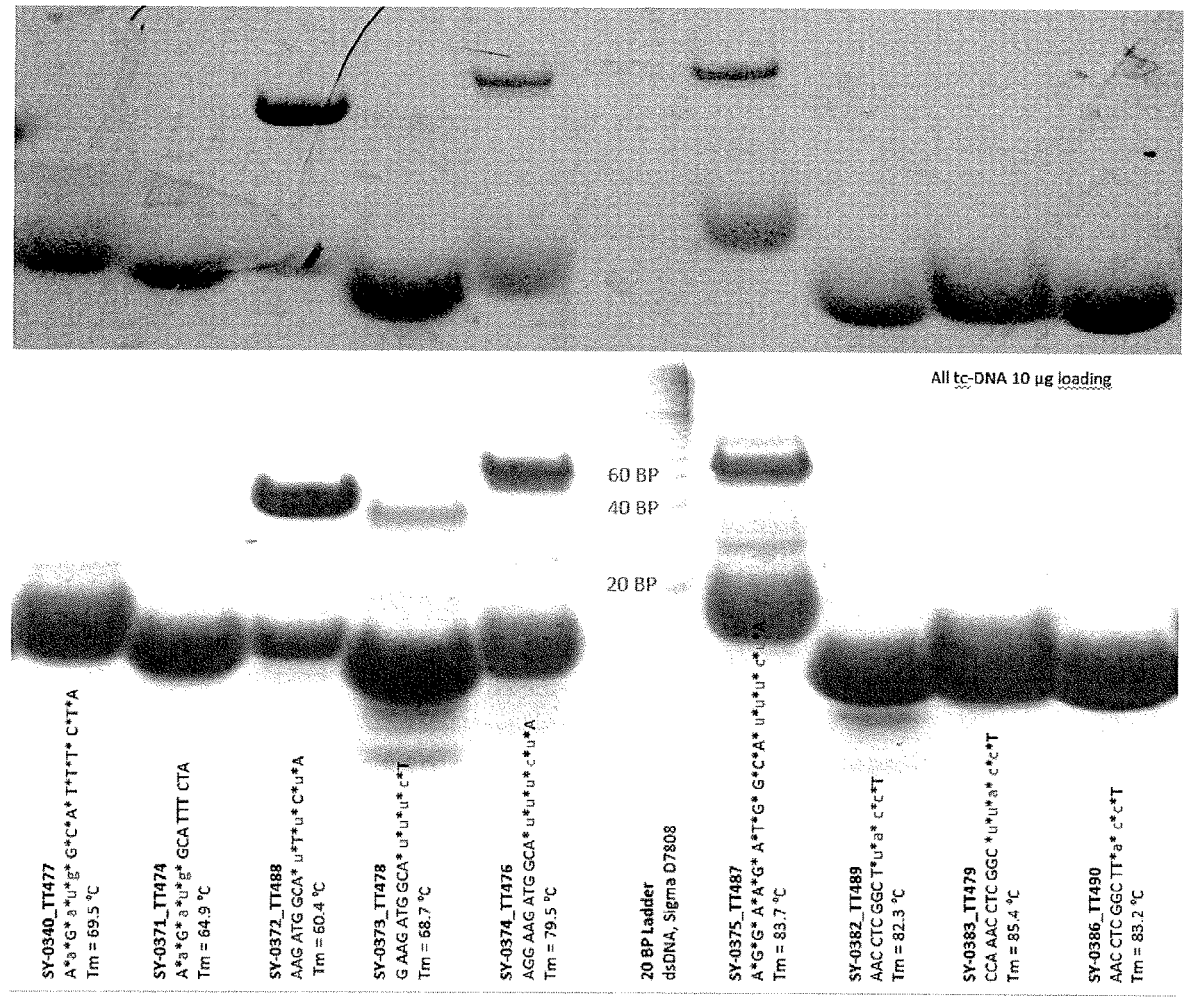
FIG. 19 illustrates the results of gel electrophoresis analysis for oligonucleotides of the present invention.

The results of complement assays using the foregoing exemplary oligonucleotides are shown in FIG. 14, FIG. 15, and FIG. 16. The results of gel electrophoresis experiments using these oligonucleotides are shown in FIG. 17, FIG. 18, and FIG. 19.

Table 5 lists additional oligonucleotides that also combine the design elements of this example.

TABLE 5

Non-limiting oligonucleotide sequences designed by the approach described in this example. A "*" represents a PS (phosphorothioate) linkage; "A", "G", "C", and "T" each represent tc-DNA; and "a", "g", "c", and "u" each represent a 2'-O-methyl RNA. All "C" are 5-methylcytosines, and all "c" are cytosines.

| Name and Identifier | Description | Sequence |
|---|---|---|
| SY-0388 SEQ ID NO: 47 | Hex51 (+67; +84) 2-OMe 18 (6Sb3) | AGG AAG ATG G*c*a* u*u*u* CTA |
| SY-0389 SEQ ID NO: 48 | Hex51 (+67; +84) 2-OMe 19 (8Sb3) | AGG AAG ATG G*c*a* u*u*u* c*u*A |
| SY-0390 SEQ ID NO: 49 | Hex51 (+64; +80) 2-OMe 20 (6Sb5) | A*a*G* a*u*g* GCA TTT CTA GTT |

TABLE 5-continued

Non-limiting oligonucleotide sequences designed by the approach described in this example. A "*" represents a PS (phosphorothioate) linkage; "A", "G", "C", and "T" each represent tc-DNA; and "a", "g", "c", and "u" each represent a 2'-O-methyl RNA. All "C" are 5-methylcytosines, and all "c" are cytosines.

| Name and Identifier | Description | Sequence |
|---|---|---|
| SY-0391 SEQ ID NO: 50 | Hex51 (+64; +80) 2-OMe 21 (6Sb5) | A*a*g* a*u*g* GCA TTT CTA GTT |
| SY-0392 SEQ ID NO: 51 | Hex51 (+64; +80) 2-OMe 22 (5Sb5) | AA*g* a*u*g* GCA TTT CTA GTT |
| SY-0393 SEQ ID NO: 52 | Hex51 (+66; +83) 2-OMe 23 (4Sbi) | AGG AAG* a*u*g* GCA TTT CTA |
| SY-0394 SEQ ID NO: 53 | Hex51 (+66; +83) 2-OMe 24 (6Sbi) | AGG A*a*g* a*u*g* GCA TTT CTA |
| SY-0395 SEQ ID NO: 54 | Hex51 (+66; +82) 2-OMe 25 (6Sbi) | GG A*a*g* a*u*g* GCA TTT CTA |
| SY-0396 SEQ ID NO: 55 | Hex51 (+67; +82) 2-OMe 26 (6Sbi) | GG A*a*g* a*u*g* GCA TTT CT |
| SY-0397 SEQ ID NO: 56 | Hex51 (+66; +83) 2-OMe 27 (6Sbi) | AGG AA*g* a*u*g* g*CA TTT CTA |
| SY-0398 SEQ ID NO: 57 | Hex51 (+66; +83) 2-OMe 28 (7Sbi) | AGG A*a*g* a*u*g* g*CA TTT CTA |

Figure 20:
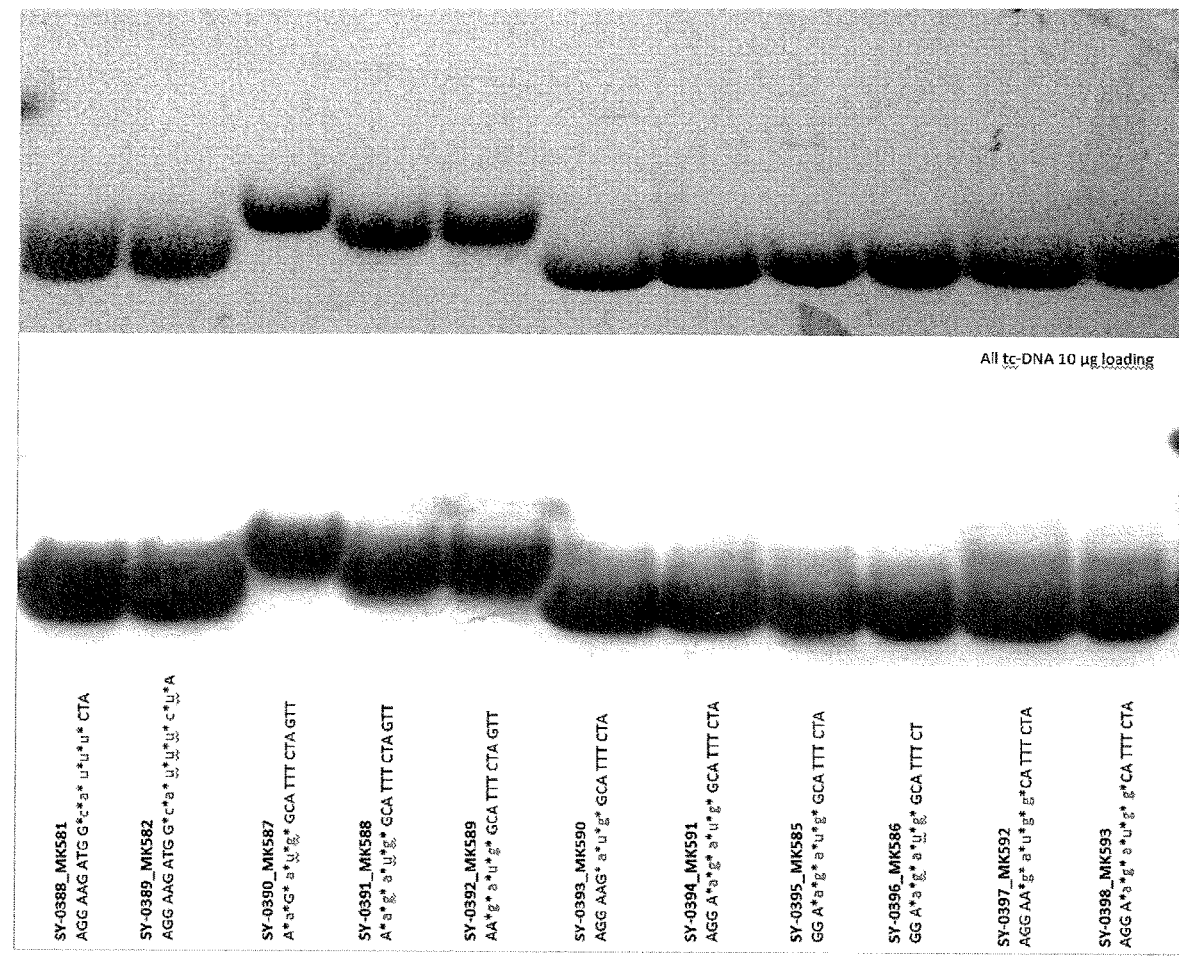
FIG. 20 illustrates the results of gel electrophoresis analysis for oligonucleotides of the present invention.

The results of gel electrophoresis experiments using these oligonucleotides are shown in FIG. 20.

Melting temperatures against complementary RNA were determined as follows. A Varian Cary UV spectrometer was used. The buffer was 75 mM NaCl, 10 mM $NaH_2PO_4$, pH 7.0. This was prepared by dissolving 2.19 g of NaCl and 780 mg of $NaH_2PO_4.2H_2O$ in about 240 mL of water. The pH is adjusted to 7.0 with 1 N sodium hydroxide solution. In a volumetric flask, the solution is diluted to 250 mL with water. Samples were tested at a concentration of 2 μM. A wavelength of 260 nm was used. The temperature gradient was 0.5 OC/minute. The temperature cycle used was 90° C.→20° C.→90° C.→20° C.→90° C.→20° C.→90° C. The complements were r⁵'(UAG AAA UGC CAU CUU)³' or r⁵'(AAC UAG AAA UGC CAU CUU CCU)³'. For determination of melting temperature for self-multimers of each sequence, the same instrument, buffer, wavelength, temperature gradient, and temperature cycle as above was used, but the sample concentration was increased to 4 μM The RNA control sequence was SY-0208 (AAG ATG GCA TTT CTA, SEQ ID NO:72). Results are reported in Table 6, along with PAGE and complement activation results (using the methods described above).

TABLE 6

Melting temperature, PAGE, and complement activation results for selected oligonucleotides.

| Name and Identifier | $T_m$ | $\Delta T_m$ against RNA | $\Delta T_m$ against RNA/mod | $\Delta T_m$ single strand | $\Delta T_m$ single strand/mod | PAGE | Complement activation in mice (mean of three replicates)[3] |
|---|---|---|---|---|---|---|---|
| SY-0208 SEQ ID NO: 72 | n/a | 0 | 0 | 0 | 0 | "dimer" | 2009 |
| SY-0329 SEQ ID NO: 31 | n/a | −3.8 | −3.8 | −12.6 | −12.6 | Weak "dimer" | 1777 (36.0%) |
| SY-0330 SEQ ID NO: 32 | n/a | −3.8 | −3.8 | −7.2[1] | −7.2[1] | Single-strand | 2774 (56.2%) |
| SY-0331 SEQ ID NO: 33 | n/a | −5.6 | −5.6 | +5.8 | +5.8 | Single-strand | 2182 (44.2%) |
| SY-0332 SEQ ID NO: 34 | n/a | −4.8 | −4.8 | +11.4 | +11.4 | Single-strand | 2247 (45.6%) |
| SY-0333 SEQ ID NO: 35 | n/a | −5.0 | −2.5 | −20.4 | −10.2 | Single-strand | 2362 (47.9%) |
| SY-0334 SEQ ID NO: 36 | n/a | −10.6 | −5.3 | −8.8[1] | −4.4[1] | Single-strand | 2364 (48.0%) |
| SY-0335 SEQ ID NO: 37 | n/a | −9.5 | −4.8 | −5.0 | −2.5 | Single-strand | 2776 (56.3%) |
| SY-0337 SEQ ID NO: 38 | n/a | −7.8 | −2.6 | −24.4 | −8.1 | Single-strand | 2433 (49.3%) |
| SY-0338 SEQ ID NO: 39 | n/a | −10.5 | −3.5 | −20.4 | −6.8 | Single-strand | 2473 (50.1%) |
| SY-0339 SEQ ID NO: 40 | n/a | −14.4 | −4.8 | −9.6[1] | −3.2[1] | Single-strand | 2643 (53.6%) |
| SY-0340 SEQ ID NO: 41 | n/a | −10.6 | −2.6 | −35.2[1] | −8.8[1] | Single-strand | 2609 (52.9%) |

TABLE 6-continued

Melting temperature, PAGE, and complement activation results for selected oligonucleotides.

| Name and Identifier | $T_m$ | $\Delta T_m$ against RNA | $\Delta T_m$ against RNA/mod | $\Delta T_m$ single strand | $\Delta T_m$ single strand/mod | PAGE | Complement activation in mice (mean of three replicates)[3] |
|---|---|---|---|---|---|---|---|
| SY-0341 SEQ ID NO: 42 | n/a | −15.8 | −3.9 | No transition | No transition | Single-strand | 2629 (53.2%) |
| SY-0371 SEQ ID NO: 43 | 64.9 | −14.7 | −3.7 | n/a | n/a | Single-strand | 60.53% |
| SY-0372 SEQ ID NO: 44 | 60.4 | −19.2 | −6.4 | n/a | n/a | Multimer | 40.50% |
| SY-0373 SEQ ID NO: 45 | 68.7 | n/a | n/a | n/a | n/a | Weak Multimer | 47.93% |
| SY-0374 SEQ ID NO: 46 | 79.5 | n/a | n/a | n/a | n/a | Multimer | 45.53% |

[1]RSD > 4.0%.
[2]Weak transition.
[3]% values are reported as a percentage of the result with the control (phosphate-buffered saline).

Additional detailed results of the melting temperature determinations are given in FIG. 21 and FIG. 22.

Additional melting temperature and SEC results are given in Table 7, along with size exclusion chromatography results using the method described in Example 2. For the SEC analysis, freshly prepared solutions with a concentration of 5 mg/mL were injected, and the area % of the peak eluting before the signal of the single strand is reported.

TABLE 7

Melting temperature and SEC results for selected oligonucleotides.

| Name (Batch) and Identifier | Sequence | $T_m$ against RNA (° C.) | PAGE | SEC (area %) |
|---|---|---|---|---|
| SY-0388 (MK581) SEQ ID NO: 47 | AGG AAG ATG G*c*a* u*u*u* CTA | 77.1 | Single-strand | 0.3 |
| SY-0389 (MK582) SEQ ID NO: 48 | AGG AAG ATG G*c*a* u*u*u* c*u*A | 76.9 | Single-strand | 1.4 |
| SY-0390 (MK587) SEQ ID NO: 49 | A*a*G* a*u*g* GCA TTT CTA GTT | 72.4 | Single-strand | 1.3 |
| SY-0391 (MK588) SEQ ID NO: 50 | A*a*g* a*u*g* GCA TTT CTA GTT | 73.1 | Single-strand | 2.5 |
| SY-0392 (MK589) SEQ ID NO: 51 | AA*g* a*u*g* GCA TTT CTA GTT | 72.8 | Single-strand | 1.6 |
| SY-0393 (MK590) SEQ ID NO: 52 | AGG AAG* a*u*g* GCA TTT CTA | 78.1 | Single-strand | 3.2 |
| SY-0394 (MK596) SEQ ID NO: 53 | AGG A*a*g* a*u*g* GCA TTT CTA | 76.1 | Single-strand | 3.1 |

TABLE 7-continued

Melting temperature and SEC results for selected oligonucleotides.

| Name (Batch) and Identifier | Sequence | $T_m$ against RNA (° C.) | PAGE | SEC (area %) |
|---|---|---|---|---|
| SY-0395 (MK585) SEQ ID NO: 54 | GG A*a*g* a*u*g* GCA TTT CTA | 75.5 | Single-strand | 1.8 |
| SY-0396 (MK586) SEQ ID NO: 55 | GG A*a*g* a*u*g* GCA TTT CT | 74.1 | Single-strand | 1.0 |
| SY-0397 (MK592) SEQ ID NO: 56 | AGG AA*g* a*u*g* g*CA TTT CTA | 77.1 | Single-strand | 3.1 |
| SY-0398 (MK593) SEQ ID NO: 57 | AGG A*a*g* a*u*g* g*CA TTT CTA | 75.7 | Single-strand | 1.2 |

Additional detailed results of the melting temperature determinations for these oligomeric compounds are given in FIG. 23.

As described above, the introduction of new chemistry (e.g., 2'-OMe-RNA) into a full tc-DNA backbone at the position of self-multimerization can break multimers, but such an alternation of tc-DNA backbone also typically lowers the affinity towards target RNA. Therefore, single incorporation of new chemistry (e.g., 2'-OMe-RNA), when correctly placed within the sequence, can lead to disruption of multimers while maintaining sufficient affinity towards target RNA. Although the prediction of multimer formation, based just on a simple analysis of its ability to form self-complementary duplexes is not reliable, once sequences forming multimers have been identified (e.g. by PAGE), the multimer formation can be efficiently suppressed via modification of a single position within putative self-complementary duplex with at least three consecutive self-complementary Watson-Crick base pairs. This has been demonstrated on the set of sequences given in Table 8.

TABLE 8

Non-limiting oligonucleotide sequences designed by the approach described in this example. "A", "G", "C", and "T" each represent tc-DNA; and "a", "g", "c", and "u" each represent a 2'-O-methyl RNA. All "C" are 5-methylcytosines, and all "c" are cytosines. All internucleosidic linkages are PS

| Name and Identifier | Description | Sequence |
|---|---|---|
| SY-0462 SEQ ID NO: 88 | Hex45 (−2; +13) | CAT CCT GGA GTT CCT |
| SY-0463 SEQ ID NO: 89 | Hex45 (−2; +13) 2-OMe 01 | CAT CCT GgA GTT CCT |
| SY-0464 SEQ ID NO: 90 | Hex45 (+1; +15) | GCC ATC CTG GAG TTC |
| SY-0465 SEQ ID NO: 91 | Hex45 (+1; +15) 2-OMe 01 | GCC ATC CTG gAG TTC |
| SY-0466 SEQ ID NO: 92 | Hex45 (+13; +27) | CCG CTG CCC AAT GCC |
| SY-0467 SEQ ID NO: 93 | Hex45 (+15; +29) | TGC CGC TGC CCA ATG |
| SY-0471 SEQ ID NO: 94 | Hex45 (−6; +9) | CTG GAG TTC CTG TAA |
| SY-0472 SEQ ID NO: 95 | Hex45 (−6; +9) 2-OMe 01 | CTG gAG TTC CTG TAA |
| SY-0473 SEQ ID NO: 96 | Hex45 (−4; +11) | TCC TGG AGT TCC TGT |
| SY-0474 SEQ ID NO: 97 | Hex45 (−4; +11) 2-OMe 01 | TCC TGg AGT TCC TGT |
| SY-0468 SEQ ID NO: 98 | Hex53 (+17; +31) | ACT TCA TCC CAC TGA |
| SY-0469 SEQ ID NO: 99 | Hex53 (+17; +31) 2-OMe 01 | ACT TcA TCC CAC TGA |
| SY-0470 SEQ ID NO: 100 | Hex53 (+59; +73) | ATT TCA TTC AAC TGT |
| SY-0475 SEQ ID NO: 101 | Hex53 (+27; +41) | GTG TTC TTG TAC TTC |
| SY-0476 SEQ ID NO: 102 | Hex53 (+27; +41) 2-OMe 01 | GTG TTC TTG TaC TTC |
| SY-0477 SEQ ID NO: 103 | Hex53 (+33; +47) | CTG AAG TGT TCT TTG |
| SY-0478 SEQ ID NO: 104 | Hex53 (+33; +47) 2-OMe 01 | CTG AaG TGT TCT TTG |
| SY-0479 SEQ ID NO: 105 | Hex53 (+41; +55) | CTC CGG TTC TGA AGG |
| SY-0480 SEQ ID NO: 106 | Hex53 (+41; +55) 2-OMe 01 | CTC CGG TTc TGA AGG |
| SY-0481 SEQ ID NO: 107 | Hex53 (+73; +87) | TTG AAT CCT TTA ACA |
| SY-0482 SEQ ID NO: 108 | Hex53 (+73; +87) 2-OMe 01 | TTG AAT CCT uTA ACA |
| SY-0221 SEQ ID NO: 109 | PS SMN 2i7 | CTT TCA TAA TGC TGG |
| SY-0483 SEQ ID NO: 110 | PS SMN 2i7 2-OMe 01 | CTT TCa TAA TGC TGG |
| SY-0484 SEQ ID NO: 111 | PS SMN 2i7 2-OMe 02 | CTT TCA TAA uGC TGG |

According to expectation the introduction of a single 2'-MeO-RNA modification into full tc-DNA backbone resulted in slight decrease in Tm towards its complementary RNA compare to parent full tc-DNA sequence. All multimer forming full tc-DNA sequences were efficiently broken into their respective monomeric forms via introduction of single 2'-MeO-RNA modification into the backbone. These results are demonstrated in Table 9.

TABLE 9

Melting temperature and PAGE results for selected oligonucleotides.

| Name (Batch) and Identifier | Sequence | Tm against RNA (° C.) | PAGE |
|---|---|---|---|
| SY-0462_TT665 SEQ ID NO: 88 | CAT CCT GGA GTT CCT | >90 | single-strand |
| SY-0463_TT677 SEQ ID NO: 89 | CAT CCT GgA GTT CCT | >90 | single-strand |
| SY-0464_TT666 SEQ ID NO: 90 | GCC ATC CTG GAG TTC | >90 | multimer |
| SY-0465_TT678 SEQ ID NO: 91 | GCC ATC CTG gAG TTC | >90 | single-strand |

TABLE 9-continued

Melting temperature and PAGE results for selected oligonucleotides.

| Name (Batch) and Identifier | Sequence | Tm against RNA (°C.) | PAGE |
|---|---|---|---|
| SY-0466_TT667 SEQ ID NO: 92 | CCG CTG CCC AAT GCC | >90 | single-strand |
| SY-0467_TT668 SEQ ID NO: 93 | TGC CGC TGC CCA ATG | >90 | multimer |
| SY-0468_TT669 SEQ ID NO: 94 | ACT TCA TCC CAC TGA | 89.6 | single-strand |
| SY-0469_TT679 SEQ ID NO: 95 | ACT TcA TCC CAC TGA | 83.6 | single-strand |
| SY-0470_TT670 SEQ ID NO: 96 | ATT TCA TTC AAC TGT | 72.0 | single-strand |
| SY-0471_TT671 SEQ ID NO: 97 | CTG GAG TTC CTG TAA | 89.4 | single-strand |
| SY-0472_TT680 SEQ ID NO: 98 | CTG gAG TTC CTG TAA | 85.0 | single-strand |
| SY-0473_TT672 SEQ ID NO: 99 | TCC TGG AGT TCC TGT | >90 | multimer |
| SY-0474_TT681 SEQ ID NO: 100 | TCC TGg AGT TCC TGT | >90 | single-strand |
| SY-0475_TT673 SEQ ID NO: 101 | GTG TTC TTG TAC TTC | 81.0 | single-strand |
| SY-0476_TT682 SEQ ID NO: 102 | GTG TTC TTG TaC TTC | 74.4 | single-strand |
| SY-0477_TT674 SEQ ID NO: 103 | CTG AAG GTG TTC TTG | 85.2 | single-strand |
| SY-0478_TT683 SEQ ID NO: 104 | CTG AaG GTG TTC TTG | 81.4 | single-strand |
| SY-0479_TT675 SEQ ID NO: 105 | CTC CGG TTC TGA AGG | >90 | weak multimer |
| SY-0480_TT684 SEQ ID NO: 106 | CTC CGG TTc TGA AGG | 89.0 | single-strand |
| SY-0481_TT676 SEQ ID NO: 107 | TTG AAT CCT TTA ACA | 72.4 | weak multimer |
| SY-0482_TT685 SEQ ID NO: 108 | TTG AAT CCT tTA ACA | 65.5 | single-strand |
| SY-0221_MK659 SEQ ID NO: 109 | CTT TCA TAA TGC TGG | n.d. | weak multimer |
| SY-0483_TT686 SEQ ID NO: 110 | CTT TCa TAA TGC TGG | n.d. | single-strand |
| SY-0484_TT687 SEQ ID NO: 111 | CTT TCA TAA tGC TGG | n.d | single-strand |

Figure 24A:
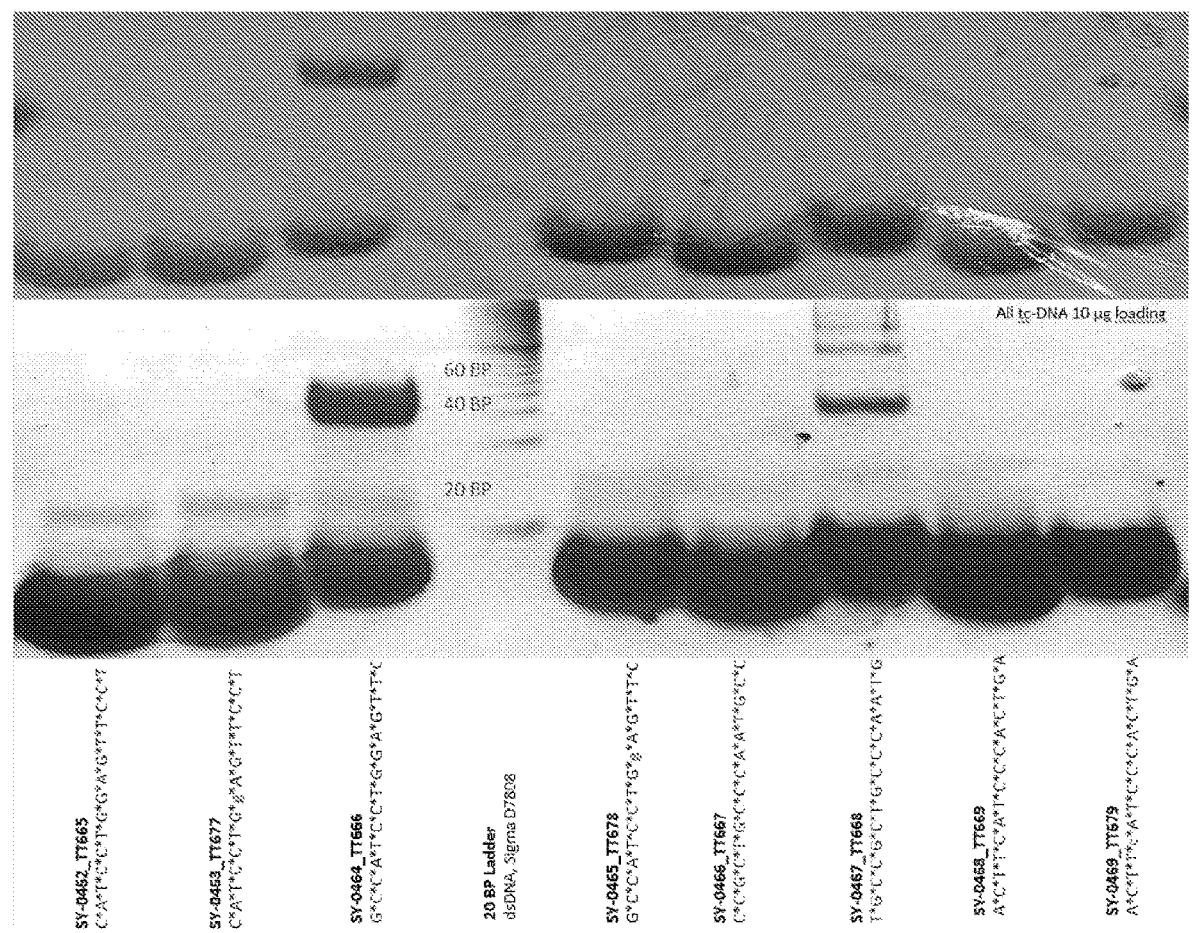
FIG. 24 illustrates the results of gel electrophoresis analysis for oligonucleotides of the present invention (visualization with UV at 258 nm and StainsAll).
Figure 24B:
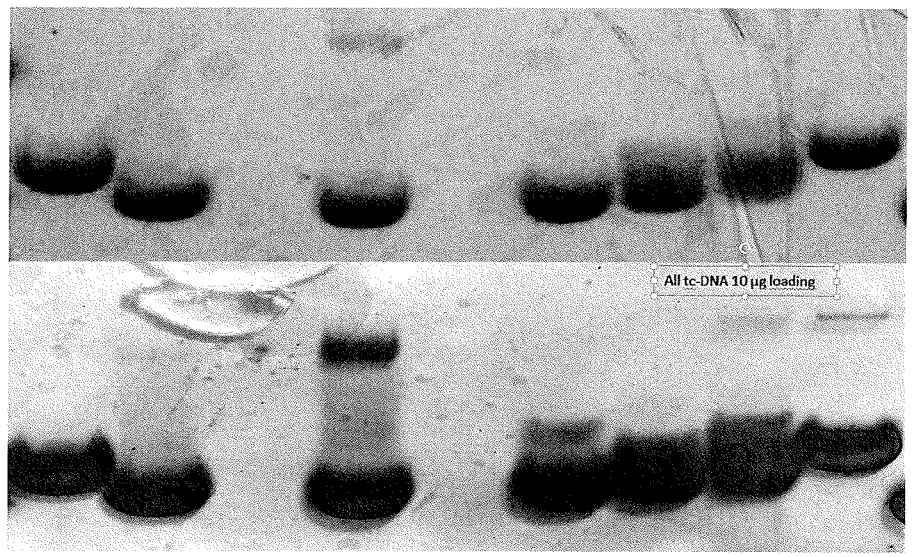
Figure 24C:
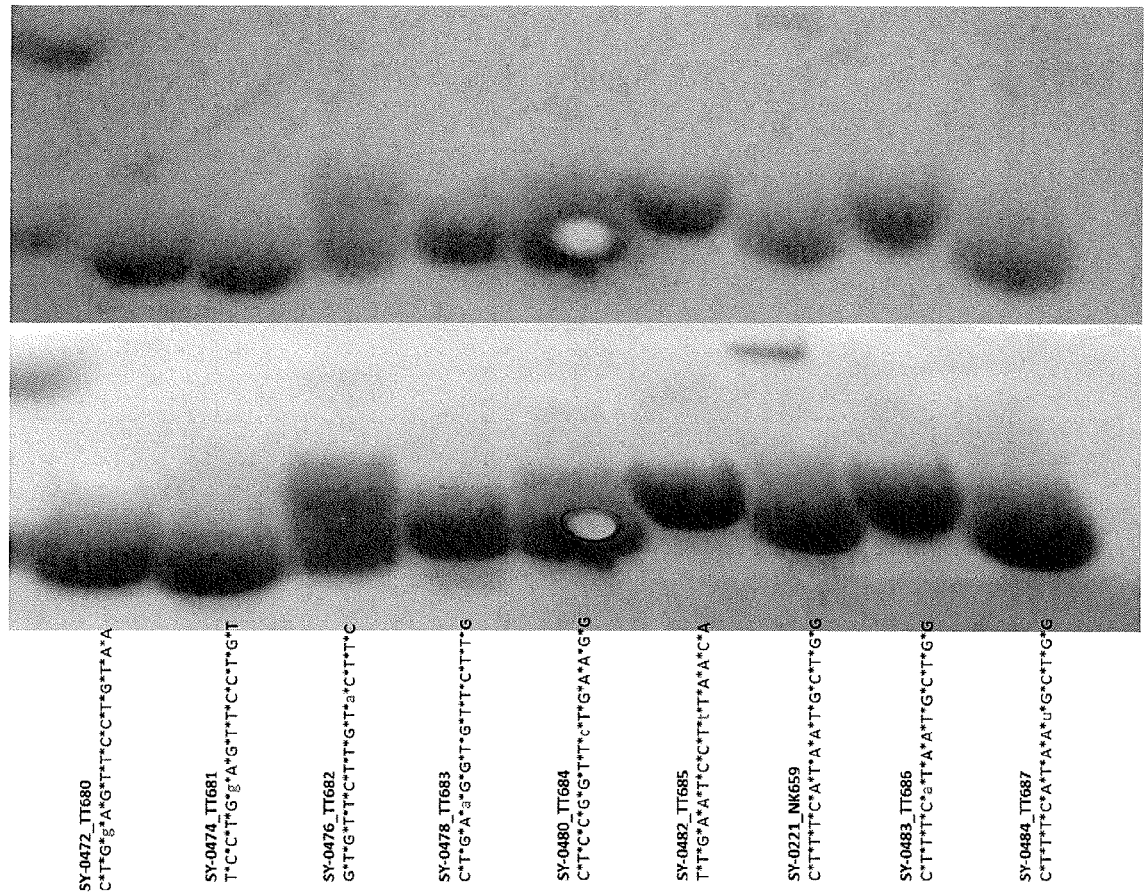

The results of gel electrophoresis experiments using these oligonucleotides are shown in FIG. 24.

---

We claim:

1. An oligomeric compound comprising:
   one or more tricyclo-deoxyribonucleic acid (tc-DNA) nucleosides and one or more 2'-modified ribonucleic acid (2'-modified-RNA) nucleosides, and optionally including one or more non-nucleosides;
   which are joined by a plurality of internucleoside linkages;
   wherein the oligomeric compound is a monomer as determined by non-denaturing gel electrophoresis.

2. The oligomeric compound of claim 1, comprising from about 10 to about 20 nucleotides.

3. The oligomeric compound of claim 1, wherein the melting temperature ($T_m$) of the oligomeric compound is at least 50° C.

4. The oligomeric compound of claim 1, wherein the one or more 2'-modified-RNA nucleosides are incorporated in positions such that self-complementary binding under physiological conditions is prevented.

5. The oligomeric compound of claim 1, wherein the one or more 2'-modified-RNA nucleosides are incorporated in at least one position that forms self-complementary Watson-Crick base pairs.

6. The oligomeric compound of claim 1, wherein the one or more 2'-modified-RNA nucleosides are incorporated in at least two adjacent positions that form self-complementary Watson-Crick base pairs.

7. The oligomeric compound of claim 1, wherein the one or more 2'-modified-RNA nucleosides are incorporated at three or more adjacent positions that form self-complementary Watson-Crick base pairs.

8. The oligomeric compound of claim 1, wherein the oligomeric compound does not contain a direct tc-DNA to tc-DNA phosphorothioate internucleoside linkage.

9. The oligomeric compound of claim 1, which is complementary to a target sequence.

10. The oligomeric compound of claim 1, wherein the one or more 2'-modified-RNA nucleosides are 2'-O-methyl-RNA nucleosides.

11. The oligomeric compound of claim 1, wherein the one or more 2'-modified-RNA nucleosides are 2'-fluoro-RNA nucleosides.

12. The oligomeric compound of claim 1, wherein the one or more 2'-modified-RNA nucleosides are locked nucleic acid RNA nucleosides.

13. The oligomeric compound of claim 1, wherein each of the plurality of internucleoside linkages is independently selected from a phosphorothioate linkage, a phosphorodithioate linkage, and a phosphorodiester linkage, a phosphotriester linkage, an aminoalkylphosphotriester linkage, a methyl phosphonate linkage, an alkyl phosphonate linkage, a 5'-alkylene phosphonate linkage, a phosphonate linkage, a phosphinate linkage, a phosphoramidate linkage, an 3'-aminophosphoramidate linkage, an aminoalkyl phosphoramidate linkage, a thionophosphoramidate linkage, a thionoalkylphosphonate linkage, a thionoalkylphosphotriester linkage, a selenophosphate linkage, or a boranophosphate linkage.

14. The oligomeric compound of claim 1, wherein the internucleoside linkages comprise a plurality of phosphorothioate linkages and a plurality of phosphorodiester linkages.

15. The oligomeric compound of claim 14, wherein no more than 50% of the plurality of internucleoside linkages are phosphorothioate linkages.

16. The oligomeric compound of claim 14, wherein no more than 33% of the plurality of internucleoside linkages are phosphorothioate linkages.

17. The oligomeric compound of claim 14, wherein no more than 25% of the plurality of internucleoside linkages are phosphorothioate linkages.

18. The oligomeric compound of claim 14, wherein at least 50% of the plurality of internucleoside linkages are phosphorodiester linkages.

19. The oligomeric compound of claim 14, wherein at least 66% of the plurality of internucleoside linkages are phosphorodiester linkages.

20. The oligomeric compound of claim 14, wherein at least 75% of the plurality of internucleoside linkages are phosphorodiester linkages.

21. The oligomeric compound of claim 1, wherein the oligomeric compound comprises a sequence selected from the group consisting of:

```
                                        (SEQ ID NO: 43)
5'-A*a*G*a*u*g*GCATTTCTA-3', (SEQ ID NO: 44)
5'-AAGATGGCA*u*T*u*C*u*A-3', (SEQ ID NO: 45)
5'-GAAGATGGCA*u*u*u*c*T-3', (SEQ ID NO: 46)
5'-AGGAAGATGGCA*u*u*u*c*u*A-3', (SEQ ID NO: 47)
5'-AGGAAGATGG*c*a*u*u*u*CTA-3', (SEQ ID NO: 48)
5'-AGGAAGATGG*c*a*u*u*u*c*u*A-3', (SEQ ID NO: 49)
5'-A*a*G*a*u*g*GCATTTCTAGTT-3', (SEQ ID NO: 50)
5'-A*a*g*a*u*g*GCATTTCTAGTT-3', (SEQ ID NO: 51)
5'-AA*g*a*u*g*GCATTTCTAGTT-3', (SEQ ID NO: 52)
5'-AGGAAG*a*u*g*GCATTTCTA-3', (SEQ ID NO: 53)
5'-AGGA*a*g*a*u*g*GCATTTCTA-3', (SEQ ID NO: 54)
5'-GGA*a*g*a*u*g*GCATTTCTA-3', (SEQ ID NO: 55)
5'-GGA*a*g*a*u*g*GCATTTCT-3', (SEQ ID NO: 56)
5'-AGGAA*g*a*u*g*g*CATTTCTA-3', (SEQ ID NO: 57)
5'-AGGA*a*g*a*u*g*g*CATTTCTA-3', (SEQ ID NO: 58)
5'-AGGAAGATGG*c*a*u*u*u*c*u-3', (SEQ ID NO: 59)
5'-a*g*a*u*g*GCATTTCTAGTT-3', (SEQ ID NO: 60)
5'-AGGAAGATGG*c*a* u*u*u*c*u-3', (SEQ ID NO: 61)
5'-s*s*AAGAuGGCATTTCTA-3', (SEQ ID NO: 62)
5'-s*s*s*s*AAGAuGGCATTTCTA-3', (SEQ ID NO: 63)
5'-s*s*s*s*s*s*AAGAuGGCATTTCTA-3', (SEQ ID NO: 64)
5'-s*s*s*s*s*s*s*s*AAGAuGGCATTTCTA-3', (SEQ ID NO: 65)
5'-s*s*s*s*s*s*s*s*s*AAGAuGGCATTTCTA-3', (SEQ ID NO: 66)
5'-A*A*G*A*T*G*G*C*A*u*T*T*C*T*A-3', (SEQ ID NO: 67)
5'-A*A*G*A*T*G*G*C*a*T*T*T*C*T*A-3', (SEQ ID NO: 89)
5'-C*A*T*C*C*T*G*g*A*G*T*T*C*C*T-3', (SEQ ID NO: 91)
5'-G*C*C*A*T*C*C*T*G*g*A*G*T*T*C-3', (SEQ ID NO: 95)
5'-C*T*G*g*A*G*T*T*C*C*T*G*T*A-3'

(SEQ ID NO: 97)
5'-T*C*C*T*G*g*A*G*T*T*C*C*T*G*T-3'

(SEQ ID NO: 99)
5'-A*C*T*T*c*A*T*C*C*C*A*C*T*G*A-3', (SEQ ID NO: 102)
5'-G*T*G*T*T*C*T*T*G*T*a*C*T*T*C-3', (SEQ ID NO: 104)
5'-C*T*G*A*a*G*G*T*G*T*T*C*T*T*G-3', (SEQ ID NO: 106)
5'-C*T*C*C*G*G*T*T*c*T*G*A*A*G*G-3', (SEQ ID NO: 108)
5'-T*T*G*A*A*T*C*C*T*u*T*A*A*C*A-3',
```

-continued (SEQ ID NO: 110)
5'-C*T*T*T*C*a*T*A*A*T*G*C*T*G*G-3',
and (SEQ ID NO: 111)
5'-C*T*T*T*C*A*T*A*A*u*G*C*T*G*G-3', wherein an * between two nucleosides indicates a phosphorothioate, the absence of an * between two nucleosides indicates a phosphorodiester, the capitalized letters A, C, G, and T indicate tc-DNA nucleosides; the lowercase letters a, u, g, and t indicate 2'-O-methyl-RNA nucleosides, the nucleobase at all C positions is 5-methylcytosine, the nucleobase at all c positions is cytosine, and s represents a —O—$CH_2$—$CH_2$—$CH_2$—O-(1,3-propanediol) non-nucleoside.

22. A pharmaceutical composition comprising an oligonucleotide molecule according to claim 1.

* * * * *